United States Patent
Aoki et al.

(10) Patent No.: US 6,800,778 B1
(45) Date of Patent: Oct. 5, 2004

(54) PROCESS FOR PRODUCING OPTICALLY ACTIVE NAPHTHALENE DERIVATIVE AND OPTICAL RESOLVER THEREFOR

(75) Inventors: Isao Aoki, Kawanishi (JP); Mari Adachi, Kobe (JP); Mitsuru Kawada, Amagasaki (JP); Toru Yamano, Itami (JP); Naohiro Taya, Takarazuka (JP)

(73) Assignee: Takeda Chemical Industries, Ltd., Osaka (JP)

( * ) Notice: Subject to any disclaimer, the term of this patent is extended or adjusted under 35 U.S.C. 154(b) by 23 days.

(21) Appl. No.: 10/111,211
(22) PCT Filed: Oct. 19, 2000
(86) PCT No.: PCT/JP00/07282

§ 371 (c)(1),
(2), (4) Date: Apr. 22, 2002

(87) PCT Pub. No.: WO01/30763

PCT Pub. Date: May 3, 2001

(30) Foreign Application Priority Data

Oct. 22, 1999 (JP) .......................................... 11-301570
Oct. 22, 1999 (JP) .......................................... 11-301576

(51) Int. Cl.[7] ................................................ C07F 9/06
(52) U.S. Cl. ...................................................... 558/85
(58) Field of Search ........................................... 558/85

(56) References Cited

FOREIGN PATENT DOCUMENTS

| EP | 0180276 | 5/1986 |
| EP | 0305089 | 3/1989 |
| EP | 0 838 448 A1 | 4/1998 |
| GB | 1360946 | 7/1974 |
| WO | WO 99 54309 A | 10/1999 |

OTHER PUBLICATIONS

Armstrong et al, "Enantiomeric impurities in chiral catalysts, auxiliaries and synthons used in enantioselective synthesis"Tetrahedron: Asymmetry 9: 2043–2064 (1998).
"Chemical Separation of Enantiomers via Diasteromers" from *Sterochemistry of Organic Compounds* (Wiley Interscience XP002217909, Section 7–3a, pp. 332–337, 1994).
ten Hoven, W. et al. "The design of resolving agents, Chiral Cyclic Phosphoric Acid " J. Org. Chem. 50: 4508–4514 (1985).
Yamano, T. et al. "Enantioselective Hydrogenation of β–Keto Esters Catalyzed by P–Chhiral Bis(dialkylphosphino)ethanes–Ru(II)" Tetrahedron Letters 40:2577–2580 (1999).
Burk, M. J. et al. "Highly Enantioselective Hydrogenation of β–Keto Esters under Mild Conditions" J. Am. Chem. Soc. 117: 4423–4424 (1995).

*Primary Examiner*—Jospeh K. McKane
*Assistant Examiner*—Kamal Saeed

(74) *Attorney, Agent, or Firm*—Elaine M. Ramesh; Mark Chao

(57) ABSTRACT

The present invention provides a method of producing an optically active form of a compound represented by the formula (I) having a steroid $C_{17,20}$-lyase inhibitory activity and is useful as an agent for the prophylaxis or treatment of prostatism, tumor such as breast cancer, and the like or a salt thereof, which method includes reacting a mixture of optically active compounds of a naphthalene derivative represented by the formula:

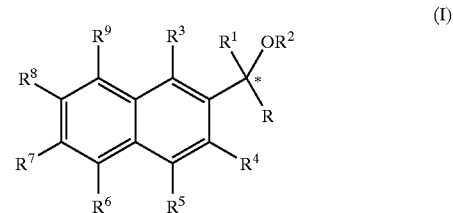

(I)

wherein R is a nitrogen-containing heterocyclic group, $R^1$ is a hydrogen atom, a hydrocarbon group or an aromatic heteromonocyclic group, $R^2$ is a hydrogen atom or a lower alkyl group, * shows the position of an asymmetric carbon, $R^3$, $R^4$, $R^5$, $R^6$, $R^7$, $R^8$ and $R^9$ are each independently a hydrogen atom, a hydrocarbon group, a hydroxy group, a thiol group, an amino group, a carbamoyl group, an acyl group or a halogen atom, and $R^7$ is bonded with $R^6$ or $R^8$ to form, together with a carbon atom on a naphthalene ring, a 5 or 6-membered ring containing an oxygen atom, with an optically active form of a compound represented by the formula:

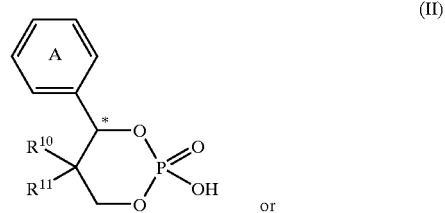

(II)

or

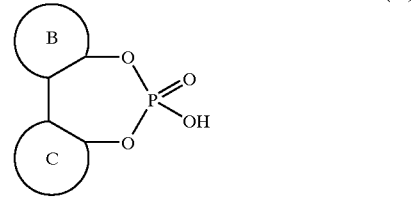

(III)

wherein ring A is a benzene ring, $R^{10}$ and $R^{11}$ are the same or different and each is a hydrogen atom, a hydrocarbon group or a halogen atom, or $R^{10}$ and $R^{11}$ in combination show an alkylene group, * shows the position of an asymmetric carbon, and ring B and ring C are each an aromatic ring, separating the resulting salt, and isolating the optically active form, and a novel reagent for optical resolution.

2 Claims, No Drawings

PROCESS FOR PRODUCING OPTICALLY ACTIVE NAPHTHALENE DERIVATIVE AND OPTICAL RESOLVER THEREFOR

This application is the National Phase filing of International Patent Application No. PCT/JP00/07282, filed Oct. 19, 2000.

TECHNICAL FIELD

The present invention relates to a production method of an optically active naphthalene derivative having a pharmacological action, particularly a steroid $C_{17,20}$-lyase inhibitory activity, a reagent for optical resolution thereof and a production method of the reagent for optical resolution. More specifically, the present invention relates to a production method of naphthalene derivatives which comprises use of an optically active cyclic phosphorus compound as a reagent for optical resolution, a salt formed during the optical resolution, a novel optically active dioxaphosphorinan useful as a reagent for optical resolution, a reagent for optical resolution containing a novel optically active dioxaphosphorinan and a production method of the reagent for optical resolution.

BACKGROUND ART

Since chemically synthesized naphthalene derivatives represented by the formula (I) have an asymmetric carbon and have two kinds of optical isomers, there is a demand for a technique to selectively and efficiently prepare an optically active form thereof. For the production of an optically active amino compound, it is a general practice to use what is called a diastereomer salt method which comprises reacting an optically active acid compound with an amino compound (racemate) and separating the resulting salt mixture based on differences in the physical properties. For use of this method, various optically active acidic compounds have been developed and utilized as reagents for optical resolution (Separation Purification Technique Handbook, The Chemical Society of Japan, Maruzen, p. 459 (1993)).

Some of the optically active compounds represented by the formula (II) can be prepared according to the method described in JP-A-61-103886 and the like and are used for the optical resolution of amino acids, such as p-hydroxyphenyl glycine and phenylalanine, and amino compounds, such as 1-phenyl-2-paramethoxyphenylethylamine and 1,2-di(4'-chlorophenyl)-1,2-diamino-ethane.

An optically active compound represented by the formula (III) can be produced according to the method described in JP-B-55-47013 and the like and is used as a reagent for the resolution of amino acids such as adrenaline, lysine, glutamic acid and the like, amphetamines, basic antibiotics such as lincomycin, tetracycline and the like, atropine, scopolamine, catecholamine, ephedrine, morphine, phenothiazines, perhexilin, prostaglandins and intermediates therefor, α-p-ethoxyphenylamino-N-n-propyl-propionamide, α,α-diphenyl-α-(2-piperidine)methanol, DOPA and many other amines.

Of the reagents for optical resolution of amino compounds, an optically active dioxaphosphorinan described in The Journal of Organic Chemistry, Vol. 50, p. 4508 (1985) and JP-A-61-103886 shows relatively high efficiency of optical resolution and can be derived easily. Therefore, it characteristically permits selection of a preferable one from various reagents for optical resolution.

As a production method of an optically active dioxaphosphorinan, a method comprising optical resolution of a racemate of dioxaphosphorinan is disclosed in the above-mentioned publications.

On the other hand, what is called an asymmetric synthetic method, wherein an optically active compound is directly produced without relying on optical resolution, is remarkably progressing in recent years. For synthesis of an optically active hydroxyester compound, for example, asymmetric hydrogenation using a ruthenium—2,2'-bis(diphenylphosphino)-1,1'-binaphthyl (abbreviated as BINAP) complex (Journal of the American Chemical Society, Vol. 109, p. 5856 (1987), asymmetric hydrogenation using 1,2-bis(tert-butylmethylphosphino)ethane (abbreviated as BisP*) (Tetrahedron Letters, Vol. 40, p. 2577 (1999)), and asymmetric hydrogenation using 1,2-bis(trans-2,5-diisopropylphosphorano)ethane (abbreviated as i-Pr-BPE) (Journal of the American Chemical Society, Vol. 117, p. 4423 (1995)) are known.

While an optically active dioxaphosphorinan shows a relatively high resolution efficiency and versatility as a reagent for optical resolution, it is frequently found to be unsuitable for optical resolution of an intermediate for a pharmaceutical product having a complicated chemical structure.

According to a method disclosed for the synthesis of optically active dioxaphosphorinan, dioxaphosphorinan as a racemate is optically resolved by a diastereomer salt method. Therefore, its theoretical yield does not exceed 50%. Moreover, this method requires an optically active amine in an equivalent amount as a reagent for optical resolution, but the optically active amine is not necessarily easily available. Thus, this method is not economically advantageous.

DISCLOSURE OF THE INVENTION

The present invention provides a method for producing (R) or (S)-(I) having a high optical purity by efficient optical resolution of a mixture of optical isomers of a naphthalene derivative represented by the formula (I), a general-purpose reagent for optical resolution, which is superior in resolution efficiency, and a method for producing the resolution reagent in a high yield and in an industrially advantageous manner.

The present inventors have found that the above-mentioned objects can be achieved by converting optical isomers of a naphthalene derivative represented by the formula (I) in a mixture to diastereomer salts with an optically active acidic compound and separating the salts, and intensively investigated further to complete the present invention.

Accordingly, the present invention relates to
(1) a production method of an optically active form of a compound represented by the formula:

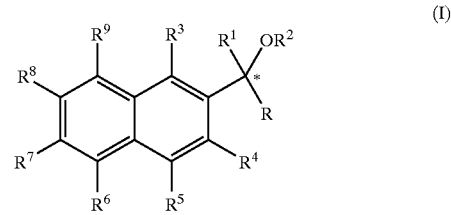

wherein R is a nitrogen-containing heterocyclic group optionally having substituents, $R^1$ is a hydrogen atom, a hydrocarbon group optionally having substituents, or a aromatic heteromonocyclic group optionally having substituents, $R^2$ is a hydrogen atom or a lower alkyl group optionally having substituents, * shows the position of an asymmetric carbon, $R^3$, $R^4$, $R^5$, $R^6$, $R^7$, $R^8$ and $R^9$ are each independently a hydrogen atom, a hydrocarbon group optionally having substituents, a hydroxy group optionally having substituents, a thiol group optionally having substituents, an amino group optionally having substituents, an acyl group or a halogen atom, and $R^7$ may be bonded with $R^6$ or $R^8$ to form, together with a carbon atom on a naphthalene ring, a 5 or 6-membered ring containing an oxygen atom, or a salt thereof, which comprises reacting a mixture of optically active compounds of the naphthalene derivative represented by the formula (I) with an optically active form of a compound represented by the formula:

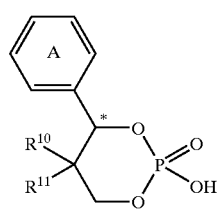

(II)

wherein ring A is a benzene ring optionally having substituents, $R^{10}$ and $R^{11}$ are the same or different and each is a hydrogen atom, a hydrocarbon group optionally having substituents or a halogen atom, or $R^{10}$ and $R^{11}$ in combination represent an alkylene group optionally having substituents, and * shows the position of an asymmetric carbon, or an optically active form of a compound represented by the formula:

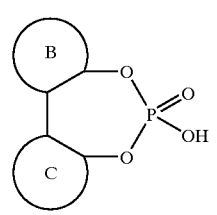

(III)

wherein ring B and ring C are each an aromatic ring optionally having substituents, separating the resulting salt and isolating an optically active form, (2) the production method according to the above-mentioned (1), wherein the nitrogen-containing heterocyclic group optionally having substituents, which is represented by R, is an imidazolyl group optionally having substituents, a thiazolyl group optionally having substituents, an oxazolyl group optionally having substituents or a pyridyl group optionally having substituents, (3) the production method according to the above-mentioned (1), wherein the nitrogen-containing heterocyclic group optionally having substituents, which is represented by R, is a 4 or 5-imidazolyl group optionally having substituents or a 3 or 4-pyridyl group optionally having substituents, (4) the production method according to the above-mentioned (1), wherein, when the nitrogen-containing heterocyclic group optionally having substituents, which is represented by R, is an oxazolyl group optionally having substituents or a thiazolyl group optionally having substituents, $R^1$ is a saturated hydrocarbon group optionally having substituents, when R is a pyridyl group and either $R^1$ or $R^2$ is a hydrogen atom, $R^7$ is a hydroxy group optionally having substituents or a lower alkyl group optionally having substituents, and when R is an oxazolyl optionally having substituents and $R^1$ is a hydrogen atom, $R^2$ is a lower alkyl group optionally having substituents, (5) the production method according to the above-mentioned (1) or (4), wherein $R^1$ is a hydrogen atom, a lower alkyl group optionally having substituents, a lower alkenyl group optionally having substituents, a cyclic alkyl group optionally having substituents or a phenyl group optionally having substituents, (6) the production method according to the above-mentioned (1) or (4), wherein $R^1$ is a lower alkyl group, (7) the production method according to the above-mentioned (1) or (4), wherein $R^2$ is a hydrogen atom or a lower alkyl group, (8) the production method according to the above-mentioned (1) or (4), wherein $R^1$ is a $C_{1-6}$ alkyl group and $R^2$ is a hydrogen atom, (9) the production method according to the above-mentioned (1) or (4), wherein $R^3$, $R^4$, $R^5$, $R^6$, $R^7$, $R^8$ and $R^9$ are each independently a hydrogen atom, a hydrocarbon group optionally having substituents, a hydroxy group optionally having substituents, an amino group optionally having substituents or an acyl group,

(10) the production method according to the above-mentioned (1) or (4), wherein 1 to 3 of $R^3$, $R^4$, $R^5$, $R^6$, $R^7$, $R^8$ and $R^9$ are each independently a hydrogen atom, a hydrocarbon group optionally having substituents, a hydroxy group optionally having substituents or an acyl group,

(11) the production method according to the above-mentioned (1) or (4), wherein $R^7$ is [1] a hydroxy group optionally having, as a substituent, a lower alkanoyl group, a lower alkanoyloxy(lower)alkyl group, a lower alkyl group, a lower alkoxy(lower)alkyl group, a lower alkyl group optionally substituted by 1 to 4 fluorine atoms, or a benzyl group, [2] a halogen atom, [3] a lower alkyl group optionally substituted by a hydroxy group, [4] a lower alkynyl group, [5] a lower alkanoyl group, [6] amino group optionally having a lower alkanoyl group, a lower alkylaminocarbonyl group or a lower alkylsulfonyl group as a substituent, [7] a lower alkylthio group or [8] a carbamoyl group optionally having substituents,

(12) the production method according to the above-mentioned (1) or (4), wherein $R^7$ is a lower alkyl group, a hydroxy group optionally having substituents, a lower alkanoylamino group, or a carbamoyl group optionally having substituents,

(13) the production method according to the above-mentioned (1) or (4), wherein $R^8$ is a hydrogen atom, a lower alkyl group or a lower alkoxy,

(14) the production method according to the above-mentioned (1) or (4), wherein $R^6$ is [1] a hydrogen atom, [2] a halogen atom, [3] a lower alkoxy group or [4] a lower alkyl group optionally substituted by a hydroxy group,

(15) the production method according to the above-mentioned (1) or (4), wherein either $R^6$, $R^7$ or $R^8$ is a lower alkyl group or a lower alkoxy group,

(16) the production method according to the above-mentioned (1) or (4), wherein $R^3$, $R^4$, $R^5$ and $R^9$ are a hydrogen atom,

(17) the production method according to the above-mentioned (1) or (4), wherein $R^7$ is a methylcarbamoyl and $R^3$, $R^4$, $R^5$, $R^6$, $R^7$, $R^8$ and $R^9$ are a hydrogen atom,

(18) the production method according to the above-mentioned (1) or (4), wherein the naphthalene derivative represented by the formula (I) is 1-(1H-imidazol-4-yl)-1-

(6-methoxynaphthalen-2-yl)-2-methyl-1-propanol, 1-(6,7-dimethoxynaphthalen-2-yl)-1-(1H-imidazol-4-yl)-2-methyl-1-propanol, 1-(6-methoxy-5-methylnaphthalen-2-yl)-1-(1H-imidazol-4-yl)-2-methyl-1-propanol, N-{6-[1-hydroxy-1-(1H-imidazol-4-yl)-2-methylpropyl]naphthalen-2-yl}acetamide, N-{6-[1-hydroxy-1-(1H-imidazol-4-yl)-2-methylpropyl]-N-methyl-2-naphthamide, N-{6-[1-hydroxy-1-(1H-imidazol-4-yl)propyl]-N-methyl-2-naphthamide or N-{6-[1-hydroxy-1-(1H-imidazol-4-yl)-3-methylbutyl]-N-methyl-2-naphthamide,

(19) the production method according to the above-mentioned (1) or (4), wherein a compound represented by the formula (I) and an optically active form of a compound represented by the formula (II) are reacted,

(20) the production method according to the above-mentioned (19) wherein the compound represented by the formula (II) is a compound represented by the formula:

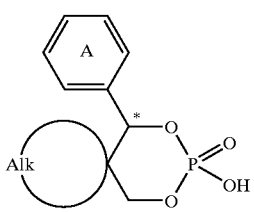

(IIa)

wherein ring A and * mean as defined above, and Alk is a $C_{2-4}$ alkylene optionally having substituents,

(21) the production method according to the above-mentioned (20) wherein the compound represented by the formula (IIa) is a compound represented by the formula:

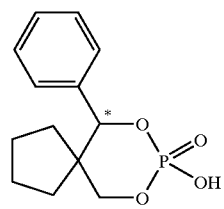

(IIb)

wherein * means as defined above,

(22) a salt of an optically active compound represented by the formula:

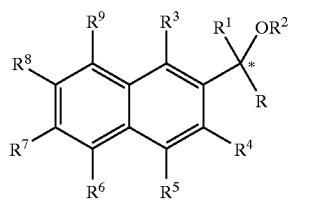

(IVa)

wherein $Q^1$ is an optically active form of a compound represented by the formula:

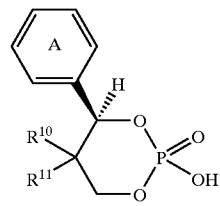

(II-1)

wherein $R^{10}$ and $R^{11}$ are the same or different and each is a hydrogen atom, a hydrocarbon group optionally having substituents or a halogen atom, or $R^{10}$ and $R^{11}$ in combination represent an alkylene group optionally having substituents and ring A is as defined above, or an optically active form of a compound represented by the formula:

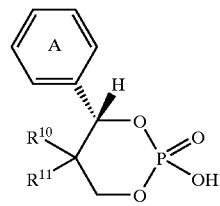

(II-2)

wherein each symbol is as defined above,

(23) a salt of an optically active compound represented by the formula:

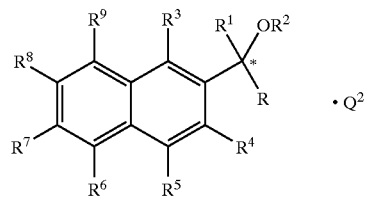

(IVb)

wherein $Q^2$ is an optically active form of a compound represented by the formula:

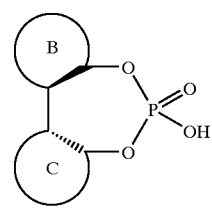

(III-1)

wherein ring B and ring C are each as defined above, or an optically active form of a compound represented by the formula:

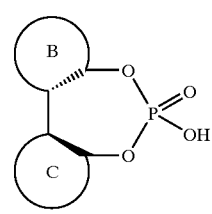

(III-2)

wherein each symbol is as defined above, and other symbols are as defined above,

(24) a salt represented by the formula:

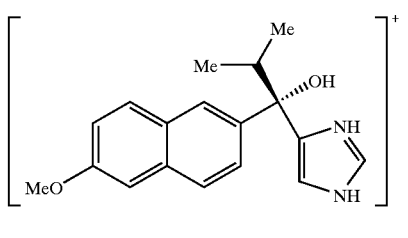

(IVa-1)

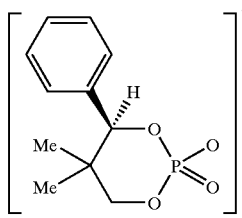

a salt represented by the formula:

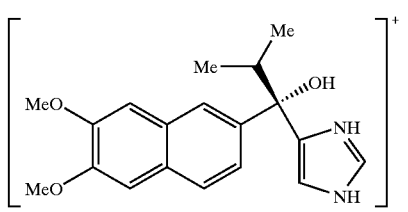

(IVa-2)

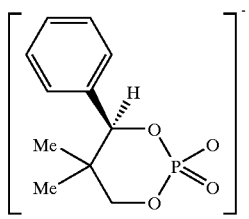

a salt represented by the formula:

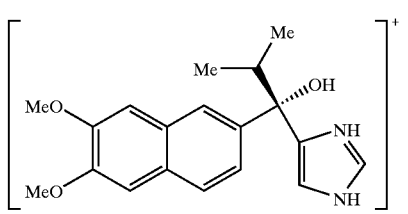

(IVa-3)

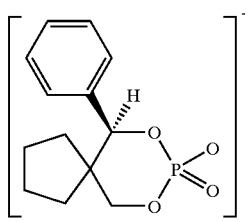

a salt represented by the formula:

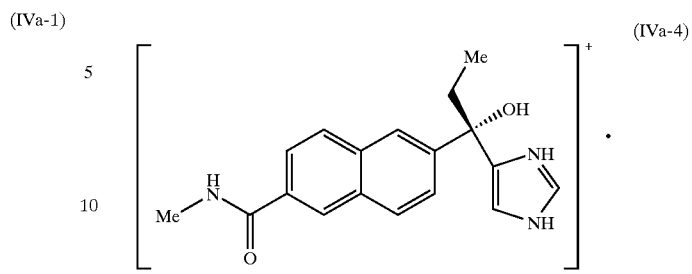

(IVa-4)

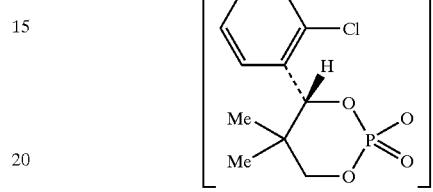

or a salt represented by the formula:

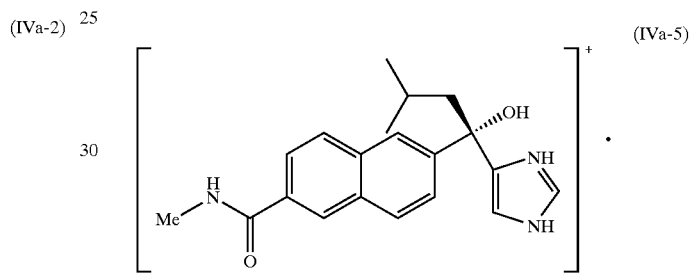

(IVa-5)

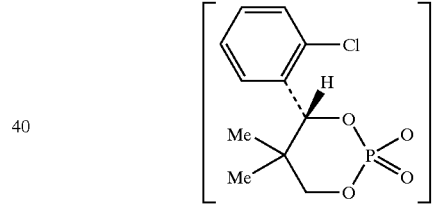

(25) a compound represented by the formula (IIa) or a salt thereof,

(26) the compound of the above-mentioned (25), which is an optically active form,

(27) a production method of an optically active form of a compound represented by the formula (II), or a salt thereof, which comprises subjecting a compound represented by the formula:

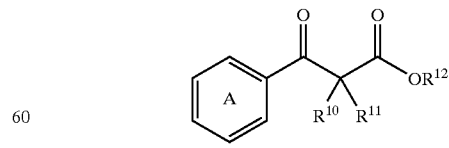

(V)

wherein $R^{12}$ is a hydrogen atom, a lower alkyl group optionally having substituents or an aryl group optionally having substituents, and other symbols are as defined above, or a salt thereof, to an asymmetric hydrogenation reaction, reducing an optically active form of the obtained compound represented by the formula;

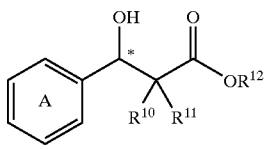
(VI)

wherein each symbol is as defined above, or a salt thereof, and subjecting an optically active form of the obtained compound represented by the formula:

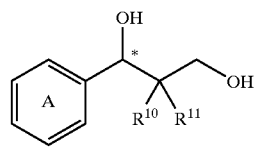
(VII)

wherein each symbol is as defined above, or a salt thereof, to phosphorylation,

(28) the production method according to the above-mentioned (27), wherein the asymmetric hydrogenation reaction is carried out in the presence of a ruthenium complex with an optically active compound represented by the formula:

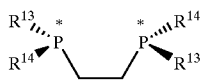
(VIII)

wherein $R^{13}$ and $R^{14}$ are different and each is a hydrocarbon group optionally having substituents or a heterocyclic ring optionally having substituents, and * means as defined above, or a salt thereof, and

(29) a reagent for optical resolution which comprises an optically active form of a compound represented by the formula (IIa) or a salt thereof.

In the above-mentioned formulas, the "nitrogen-containing heterocyclic group" of the "nitrogen-containing heterocyclic group optionally having substituents" represented by R is exemplified by a nitrogen-containing aromatic heterocyclic group or a saturated or an unsaturated nitrogen-containing non-aromatic heterocyclic group (nitrogen-containing aliphatic heterocyclic group), having, as an atom (ring atom) constituting the ring, at least one nitrogen atom, which is preferably a nitrogen-containing aromatic heterocyclic group. Examples of the nitrogen-containing aromatic heterocyclic group include 5 or 6-membered nitrogen-containing aromatic heterocyclic group such as imidazolyl, pyrrolyl, pyrazolyl, 1,2,3-triazolyl, 1,2,4-triazolyl, tetrazolyl, thiazolyl, isothiazolyl, oxazolyl, isoxazolyl, pyridyl, pyridazinyl, pyrimidinyl, pyrazinyl, 1,3,5-triazinyl and 1,2,4-triazinyl. Of these, imidazolyl, pyridyl, thiazolyl, oxazolyl and the like, particularly 4 or 5-imidazolyl group and 3 or 4-pyridyl group, are preferable.

The substituent of the "nitrogen-containing aromatic heterocyclic group optionally having substituents" represented by R may be present in the number of 1 to 3 at substitutable positions of the nitrogen-containing aromatic heterocyclic group. Examples of the substituent include lower alkyl group, lower alkoxy group, acyl group and the like, which optionally have substituents. Examples of the "lower alkyl group optionally having substituents" include non-substituted $C_{2-4}$ alkyl group such as methyl, ethyl, propyl and the like, such alkyl group substituted by $C_{1-6}$ alkanoyl (e.g., acetyl, propionyl etc.), carboxyl, $C_{1-4}$ alkoxy-carbonyl group (e.g., methoxycarbonyl, ethoxycarbonyl, butoxycarbonyl etc.) and the like. Examples of the "lower alkoxy group" include $C_{1-3}$ alkoxy group such as methoxy, ethoxy, propoxy, isopropoxy and the like.

Examples of the "acyl group" include alkanoyl group (e.g., $C_{1-6}$ alkanoyl such as formyl, acetyl, propionyl etc.), alkylsulfonyl group (e.g., $C_{1-4}$ alkylsulfonyl such as methylsulfonyl, ethylsulfonyl etc.), arylsulfonyl group (e.g., benzenesulfonyl, p-toluenesulfonyl etc.), carbamoyl group optionally having substituents (e.g., mono- or di-$C_{1-10}$ alkylcarbamoyl group such as methylcarbamoyl, ethylcarbamoyl, dimethylcarbamoyl, diethylcarbamoyl etc., mono- or di-$C_{6-14}$ arylcarbamoyl such as phenylcarbamoyl, diphenylcarbamoyl etc., mono- or di-$C_{7-16}$ aralkylcarbamoyl group such as benzylcarbamoyl, dibenzylcarbamoyl etc., and the like), sulfamoyl group optionally having substituents (e.g., mono- or di-$C_{1-10}$ alkylsulfamoyl group such as methylsulfamoyl, ethylsulfamoyl, dimethylsulfamoyl, diethylsulfamoyl etc., mono- or di-$C_{6-14}$ arylsulfamoyl group such as phenylsulfamoyl, diphenylsulfamoyl etc., mono- or di-$C_{7-16}$ aralkylsulfamoyl group such as benzylsulfamoyl, dibenzylsulfamoyl etc., and the like), lower alkoxy-carbonyl group (e.g., $C_{1-4}$ alkoxy-carbonyl group such as ethoxycarbonyl, ethoxycarbonyl, butoxycarbonyl etc., and the like), and the like.

Examples of the "hydrocarbon group" of the "hydrocarbon group optionally having substituents" represented by $R^1$ include chain hydrocarbon group, cyclic hydrocarbon group and the like.

Examples of the "chain hydrocarbon group" include linear or branched hydrocarbon groups having 1 to 10 carbon atoms, and the like, which is specifically alkyl group, alkenyl group, alkynyl group and the like. Of these, alkyl group is particularly preferable. Examples of the "alkyl group" include $C_{1-10}$ alkyl groups such as methyl, ethyl, n-propyl, isopropyl, butyl, isobutyl, sec-butyl, tert-butyl, n-pentyl, isopentyl, neopentyl, n-hexyl, isohexyl and the like, and the like, of which $C_{1-6}$ alkyl group (e.g., methyl, ethyl, n-propyl, isopropyl, n-butyl, sec-butyl, tert-butyl etc.) is preferable. Examples of the "alkenyl group" include $C_{2-10}$ alkenyl groups such as vinyl, 1-propenyl, allyl, isopropenyl, 1-butenyl, 2-butenyl, 3-butenyl, isobutenyl, sec-butenyl and the like, and the like, of which $C_{2-6}$ alkenyl group (e.g., vinyl, 1-propenyl, allyl etc.) is preferable. Examples of the "alkynyl group" include $C_{2-10}$ alkynyl groups such as ethynyl, 1-propnyl, propargyl etc., and the like, of which $C_{2-6}$ alkynyl group (e.g., ethynyl and the like) is preferable.

Examples of the "cyclic hydrocarbon group" include cyclic hydrocarbon group having 3 to 18 carbon atoms, such as alicyclic hydrocarbon group, aromatic hydrocarbon group and, the like.

Examples of the "alicyclic hydrocarbon group" include monocyclic or fused polycyclic group consisting of 3 to 10 carbon atom, which is specifically cycloalkyl group, cycloalkenyl group and 2 or 3 cyclic fused ring of these and $C_{6-14}$ aryl group (e.g., benzene etc.) and the like, and the like. Examples of the "cycloalkyl group" include $C_{3-6}$ cycloalkyl group such as cyclopropyl, cyclobutyl, cyclopentyl, cyclohexyl etc., and the like, examples of the "cycloalkenyl group" include $C_{3-6}$ cycloalkenyl group such as cyclopropenyl, cyclobutenyl, cyclopentenyl, cyclohexenyl etc., and the like.

Examples of the "aromatic hydrocarbon group" include monocyclic aromatic hydrocarbon group consisting of 6 to 18 carbon atoms, fused polycyclic aromatic hydrocarbon group and the like, which is specifically $C_{6-14}$ aryl group such as phenyl, 1-naphthyl, 2-naphthyl, 2-indenyl, 2-anthryl and the like and $C_{6-10}$ aryl group (e.g., phenyl etc.) and the like are preferable.

The substituent that the "chain hydrocarbon group" in the "hydrocarbon group optionally having substituents" may have is not particularly limited and examples thereof include halogen atom, hydroxy group, alkoxy group, acyloxy group, alkylthio group, acylamino group, carboxyl group, alkoxycarbonyl group, oxo group, alkanoyl group, cycloalkyl group, aryl group, aromatic heterocyclic group and the like. These substituents is substituted in the range chemically acceptable on the "chain hydrocarbon group" wherein the number of the substituent is 1 to 5, preferably 1 to 3. When the number of the substituents is 2 or above, they may be the same or different.

Examples of the "halogen atom" include fluorine, chlorine, bromine, iodine and the like.

Examples of the "alkoxy group" include $C_{1-10}$ alkoxy group such as methoxy, ethoxy, propoxy, isopropoxy, butoxy, isobutoxy, sec-butoxy, pentyloxy, hexyloxy etc., and the like. Examples of the "acyloxy group" include formyloxy, $C_{1-10}$ alkylcarbonyloxy group (e.g., acetoxy, propionyloxy etc.) and the like. Examples of the "alkylthio group" include $C_{1-10}$ alkylthio group such as methylthio, ethylthio, propylthio, isopropylthio etc., and the like. Examples of the "acylamino group" include formylamino, diformylamino, mono- or di-$C_{1-10}$ alkylcarbonylamino group (e.g., acetylamino, propionylamino, butyrylamino, diacetylamino etc.) and the like. Examples of the "alkoxycarbonyl group" include $C_{1-10}$ alkoxycarbonyl group such as methoxycarbonyl, ethoxycarbonyl, propoxycarbonyl, isopropoxycarbonyl, butoxycarbonyl etc., and the like. Examples of the "alkanoyl group" include $C_{1-10}$ alkylcarbonyl group such as acetyl, propionyl, butyryl, valeryl etc., and the like. Examples of the "cycloalkyl group" include $C_{3-10}$ cycloalkyl group such as cyclopropyl, cyclobutyl, cyclopentyl, cyclohexyl etc., and the like. Examples of the "aryl group" include $C_{6-14}$ aryl group such as phenyl, 1-naphthyl, 2-naphthyl etc., and the like. Examples of the "aromatic heterocyclic group" include 1 to 3 cyclic aromatic heterocyclic groups containing, besides carbon atom, preferably 1 to 4 of 1 or 2 kinds of heteroatom selected from nitrogen, oxygen and sulfur, and the like. Specific examples thereof include thienyl, pyridyl, furyl, pyrazinyl, pyrimidinyl, imidazolyl, pyrazolyl, thiazolyl, isothiazolyl, oxazolyl, isoxazolyl, pyridazinyl, tetrazolyl, quinolyl, indolyl, isoindolyl and the like.

The substituent that the "cyclic hydrocarbon group" in the "hydrocarbon group optionally having substituents" may possess is not particularly limited. Examples thereof include halogen atom, hydroxy group, alkoxy group, acyloxy group, alkylthio group, alkylsulfonyl group, mono- or di-alkylamino group, acylamino group, carboxyl group, alkoxycarbonyl group, alkanoyl group, alkynylcarbonyl group, alkyl group, cycloalkyl group, aryl group, aromatic heterocyclic group and the like. These substituents are substituted on the "cyclic hydrocarbon group" in a chemically acceptable range, wherein the number of the substituent is 1 to 5, preferably 1 to 3. When the number of substituents is 2 or above, they may be the same or different. Of these substituents, halogen atom, alkoxy group, acyloxy group, alkylthio group, acylamino group, alkoxycarbonyl group, alkanoyl group, cycloalkyl group, aryl group and aromatic heterocyclic group are similar to those defined above as the substituent on the "chain hydrocarbon group".

Examples of the "alkylsulfonyl group" include $C_{1-10}$ alkylsulfonyl groups such as methylsulfonyl, ethylsulfonyl, propylsulfonyl etc., and the like. Examples of the "alkylamino group" include mono-$C_{1-4}$ alkylamino groups such as methylamino, ethylamino, propylamino and the like, di-$C_{1-4}$ alkylamino groups such as dimethylamino, diethylamino and the like, examples of the "alkynylcarbonyl group" include $C_{3-10}$ alkynylcarbonyl groups such as ethynylcarbonyl, 1-propynylcarbonyl, 2-propynylcarbonyl etc., and the like. Example of the "alkyl group" include $C_{1-10}$ alkyl groups such as methyl, ethyl, propyl, isopropyl, butyl, sec-butyl, tert-butyl, pentyl etc., and the like.

The substituent that the aforementioned "hydrocarbon group" may have, in a chemically acceptable range, 1 to 5, preferably 1 to 3, substituents shown below. Examples of such substituent include halogen atom (e.g., fluorine, chlorine, bromine etc.), hydroxy group, $C_{1-6}$ alkoxy group (e.g., methoxy, ethoxy, propoxy, isopropoxy etc.), and the like.

Examples of the aromatic heteromonocyclic group of the "aromatic heteromonocyclic group optionally having substituents" represented by $R^1$ include 2-thienyl, 3-thienyl, 2-pyridyl, 3-pyridyl, 4-pyridyl, 2-furyl, 3-furyl, pyrazinyl, 2-pyrimidinyl, 3-pyrrolyl, 1-imidazolyl, 2-imidazolyl, 4-imidazolyl, 5-imidazolyl, 1-pyrazolyl, 2-thiazolyl, 4-thiazolyl, 5-thiazolyl, 3-isothiazolyl, 4-isothiazolyl, 2-oxazolyl, 4-oxazolyl, 5-oxazolyl, 3-isoxazolyl, 3-pyridazinyl and the like. Of these, 2-pyridyl, 3-pyridyl, 4-pyridyl, 1-imidazolyl, 4-imidazolyl and the like are preferable.

The substituent of the "aromatic heteromonocyclic group optionally having substituents" represented by $R^1$ may be substituted in the number of 1 to 3 at substitutable positions of the aromatic heteromonocyclic group. Examples of the substituent include alkyl group optionally substituted by 1 to 5 halogen atoms (e.g., fluorine, chlorine, bromine, iodine), which is exemplified by $C_{1-4}$ alkyl group such as methyl, ethyl, propyl etc. and $C_{1-4}$ alkyl group substituted by halogen such as 2,2,2-trifluoroethyl, 2,2,3,3,3-pentafluoropropyl etc., $C_{1-3}$ alkoxy group such as methoxy, ethoxy, propoxy, isopropoxy etc., halogen atom such as chlorine atom, fluorine atom etc., hydroxy group, amino group, nitro group and the like.

Of the aforementioned examples, preferable as $R^1$ are hydrogen atom, lower alkyl group (those having 1 to 4 carbon atoms) optionally having substituents, lower alkenyl group (those having 1 to 4 carbon atoms), cyclic alkyl group (those having 3 to 6 carbon atoms), phenyl group optionally having substituents and pyridyl group optionally having substituents. Of these, hydrogen atom, lower alkenyl group (those having 1 to 4 carbon atoms), cyclic alkyl group (those having 3 to 6 carbon atoms), phenyl group, pyridyl group and lower alkyl group (those having 1 to 4 carbon atoms) optionally having halogen as substituent are particularly preferable.

Examples of the lower alkyl group of $R^2$ include chain or cyclic $C_{1-6}$ alkyl group optionally having substituents (e.g., methyl, ethyl, propyl, isopropyl, cyclopropyl, butyl, isobutyl, sec-butyl, tert-butyl, pentyl, cyclopentyl, hexyl etc.). The $C_{1-6}$ alkyl group may have 1 to 5 substituents at substitutable positions and examples of the substituent include halogen (e.g., fluorine, chlorine, bromine, iodine), $C_{1-4}$ alkoxy group (e.g., methoxy, ethoxy, propoxy etc.) and the like.

Preferable examples of $R^2$ are, of the aforementioned, hydrogen atom and non-substituted lower alkyl group (those having 1 to 6 carbon atoms), particularly preferably hydrogen atom.

Examples of the "hydroxy group optionally having substituents" represented by $R^3$, $R^4$, $R^5$, $R^6$, $R^7$, $R^8$ and $R^9$ include, besides non-substituted hydroxy group, lower alkoxy group (e.g., $C_{1-4}$ alkoxy group such as methoxy, ethoxy, propoxy etc.), lower alkanoyloxy group (e.g., $C_{1-4}$ alkanoyloxy such as acetyloxy, propionyloxy etc.), carbamoyloxy group optionally having substituents (e.g., non-substituted carbamoyloxy and carbamoyloxy substituted by 1 or 2 $C_{1-4}$ alkyl groups such as, ethylcarbamoyloxy, ethylcarbamoyloxy, dimethylcarbamoyloxy, diethylcarbamoyloxy, methylethylcarbamoyloxy etc.), and the like.

Examples of the "thiol group optionally having substituents" represented by $R^3$, $R^4$, $R^5$, $R^6$, $R^7$, $R^8$ and $R^9$ include, besides non-substituted thiol group, lower alkylthio group (e.g., $C_{1-4}$ alkylthio group such as methylthio, ethylthio, propylthio etc.), lower alkanoylthio group (e.g., $C_{1-4}$ alkanoylthio such as acetylthio, propionylthio etc.), and the like.

Examples of the "amino group optionally having substituents" represented by $R^3$, $R^4$, $R^5$, $R^6$, $R^7$, $R^8$ and $R^9$ include, besides non-substituted amino group, lower alkylamino group (e.g., $C_{1-4}$ alkylamino group such as methylamino, ethylamino, propylamino etc.), di-lower alkylamino group (e.g., di-$C_{1-4}$ alkylamino such as dimethylamino, diethylamino etc.), $C_{1-4}$ alkanoylamino group (e.g., acetamide, propionamide etc.), and the like.

Examples of the acyl group represented by $R^3$, $R^4$, $R^5$, $R^6$, $R^7$, $R^8$ and $R^9$ include alkanoyl group (e.g., $C_{1-6}$ alkanoyl such as formyl, acetyl, propionyl etc.), arylsulfonyl group (e.g., benzenesulfonyl, p-toluenesulfonyl etc.), carbamoyl group optionally having substituents (besides non-substituted carbamoyl group, mono- or di-$C_{1-4}$ alkylcarbamoyl group such as methylcarbamoyl, ethylcarbamoyl, dimethylcarbamoyl, diethylcarbamoyl group etc., mono- or di-$C_{6-14}$ arylcarbamoyl group such as phenylcarbamoyl, diphenylcarbamoyl group etc., mono- or di-$C_{7-16}$ aralkylcarbamoyl group such as benzylcarbamoyl, dibenzylcarbamoyl etc.), alkylsulfonyl group (e.g., $C_{1-4}$ alkylsulfonyl such as methylsulfonyl, ethylsulfonyl etc.), sulfamoyl group optionally having substituents (e.g., mono- or di-$C_{1-10}$ alkylsulfamoyl group such as methylsulfamoyl, ethylsulfamoyl, dimethylsulfamoyl, diethylsulfamoyl etc., mono- or di-$C_{6-14}$ arylsulfamoyl group such as phenylsulfamoyl, diphenylsulfamoyl etc., mono- or di-$C_{7-16}$ aralkylsulfamoyl group such as benzylsulfamoyl, dibenzylsulfamoyl etc., and the like), lower alkoxy-carbonyl group (e.g., $C_{1-4}$ alkoxy-carbonyl group such as methoxycarbonyl, ethoxycarbonyl, butoxycarbonyl etc., and the like), and the like.

Examples of the halogen represented by $R^3$, $R^4$, $R^5$, $R^6$, $R^7$, $R^8$ and $R^9$ include fluorine, chlorine, bromine and iodine.

Examples of the "hydrocarbon group optionally having substituents" represented by $R^3$, $R^4$, $R^5$, $R^6$, $R^7$, $R^8$ and $R^9$ include those similar to the "hydrocarbon group optionally having substituents" represented by $R^1$. Of these, lower alkyl group optionally having substituents is preferable. Examples thereof include chain or cyclic $C_{1-6}$ alkyl group optionally having substituents (e.g., methyl, ethyl, propyl, isopropyl, cyclopropyl, butyl, isobutyl, sec-butyl, tert-butyl, pentyl, cyclopentyl, hexyl etc.). The $C_{1-6}$ alkyl group may have 1 to 5 substituents at substitutable positions, and examples of the substituent include halogen (e.g., fluorine, chlorine, bromine, iodine), $C_{1-4}$ alkoxy group (e.g., methoxy, ethoxy, propoxy etc.), hydroxy group, and the like. The $C_{1-4}$ alkoxy group may have 1 to 5 substituents at substitutable positions, and examples of the substituent include halogen (e.g., fluorine, chlorine, bromine, iodine), $C_{1-4}$ alkoxy group (e.g., methoxy, ethoxy, propoxy etc.), and the like.

Preferable examples of the $R^3$, $R^4$, $R^5$, $R^6$, $R^7$, $R^8$ and $R^9$ include, of the aforementioned examples, hydrogen atom, hydrocarbon group optionally having substituents, hydroxy group optionally having substituents, amino group optionally having substituents, carbamoyl group optionally having substituents, $C_{1-6}$ alkanoyl group and halogen atom.

Of $R^3$, $R^4$, $R^5$, $R^6$, $R^7$, $R^8$ and $R^9$ $R^7$ is preferably an optionally substituted hydroxy group or a lower alkyl group. It is preferably (1) hydroxy group optionally having, as a substituent, lower alkanoyl group, lower alkanoyloxy (lower)alkyl group, lower alkyl group, lower alkoxy(lower) alkyl group, lower alkyl group optionally substituted by 1 to 4 fluorine atoms or benzyl group, (2) halogen atom, (3) lower alkyl group optionally substituted by hydroxy group, (4) lower alkynyl group, (5) lower alkanoyl group, (6) amino group optionally having lower alkanoyl group, lower alkylaminocarbonyl group and lower alkylsulfonyl group as a substituent or (7) lower alkylthio group, more preferably lower alkyl group, lower alkoxy group, lower alkanoylamino group or lower alkylcarbamoyl group. $R^8$ is preferably hydrogen atom, lower alkyl group or lower alkoxy group, more preferably hydrogen atom or lower alkoxy group. $R^6$ is preferably (1) hydrogen atom, (2) halogen atom, (3) lower alkoxy group or (4) lower alkyl group optionally substituted by hydroxy group, more preferably hydrogen atom or lower alkyl group.

Examples of the combination of $R^3$, $R^4$, $R^5$, $R^6$, $R^7$, $R^8$ and $R^9$ is that wherein 1 to 3 thereof are each preferably independently lower alkyl group optionally having substituents, hydroxy group optionally having substituents, amino group optionally having substituents, carbamoyl group optionally having substituents, $C_{1-6}$ alkanoyl group or halogen atom.

It is preferable that any of $R^6$, $R^7$ and $R^8$ is lower alkyl group, lower alkoxy group, lower alkanoylamino group or lower alkylcarbamoyl group, and that all of $R^3$, $R^4$, $R^5$ and $R^9$ are hydrogen atoms.

Of the compounds (I), a compound wherein $R^1$ is $C_{1-6}$ alkyl group and $R^2$ is hydrogen atom.

When $R^7$ is bonded with $R^6$ or $R^8$ and form, together with carbon atom on the naphthalene ring, a 5 or 6-membered ring containing oxygen atom, examples of the ring include furan ring, dihydrofuran ring, pyran ring, dihydropyran ring, dioxolen ring, oxazole ring, isoxazole ring and the like.

Preferable examples of the compound represented by the formula (I) include compounds of the formulas

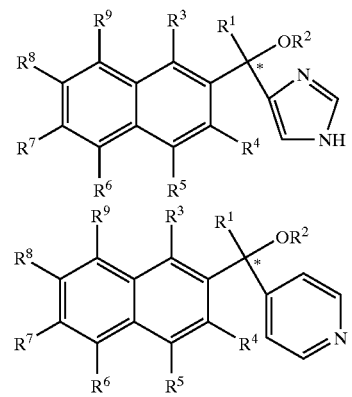

wherein each symbol is as defined above, and the like. Examples of the preferable compound include 1-(1H- imidazol-4-yl-1-(6-methoxynaphthalen-2-yl)-2-methyl-1-propanol, 1-(6,7-dimethoxynaphthalen-2-yl)-1-(1H-imidazol-4-yl)-2-methyl-1-propanol, 1-(6-methoxy-5-methylnaphthalen-2-yl)-1-(1H-imidazol-4-yl)-2-methyl-1-propanol, N-{6-[1-hydroxy-1-(1H-imidazol-4-yl)-2-methylpropyl]naphthalen-2-yl}acetamide and N-{6-[1-hydroxy-1-(1H-imidazol-4-yl)-2-methylpropyl]-N-methyl-2-naphthamide.

In the aforementioned formulas, ring A may have 1 to 5, preferably 1 or 2 substituents at optional positions. Examples of the substituent include lower alkyl group optionally having substituents, hydroxy group optionally having substituents, thiol group optionally having substituents, nitro group, amino group optionally having substituents, acyl group, halogen atom, methylenedioxy group optionally having substituents (or adjacent two substituents are bonded) and the like.

Examples of the lower alkyl group of the "optionally substituted lower alkyl group" include $C_{1-6}$ alkyl group such as methyl, ethyl, propyl, isopropyl, butyl, pentyl, hexyl and the like. Examples of the substituent include halogen atom such as fluorine, chlorine, bromine and the like, $C_{1-7}$ alkoxy group such as methoxy, ethoxy, propoxy, benzyloxy and the like, $C_{1-7}$ alkylthio group such as methylthio, ethylthio, propiothio, benzylthio and the like, hydroxy group, and substituted amino group such as acetylamino, benzoylamino, methanesulfonylamino, benzenesulfonylamino and the like.

Examples of the hydroxy group optionally having substituents include, besides non-substituted hydroxy group, lower alkoxy group (e.g., linear or branched $C_{1-6}$ alkoxy group such as methyloxy, ethyloxy, n-propyloxy, isopropyloxy, n-butyloxy, isobutyloxy, sec-butyloxy, tert-butyloxy, pentyloxy, hexyloxy etc.), lower alkanoyloxy group (e.g., $C_{1-4}$ alkanoyloxy such as acetyloxy, propionyloxy etc.), carbamoyloxy group optionally having substituents (e.g., non-substituted carbamoyloxy, carbamoyloxy substituted by 1 or 2 $C_{1-4}$ alkyl groups such as methylcarbamoyloxy, ethylcarbamoyloxy, dimethylcarbamoyloxy, diethylcarbamoyloxy, methylethylcarbamoyloxy etc.) and the like.

Examples of the thiol group optionally having substituents include, besides non-substituted thiol group, lower alkylthio group (e.g., $C_{1-4}$ alkylthio group such as methylthio, ethylthio, propylthio etc.), lower alkanoylthio group (e.g., $C_{1-4}$ alkanoylthio such as acetylthio, propionylthio etc.) and the like.

Examples of the amino group optionally having substituents include, besides non-substituted amino group, lower alkylamino group (e.g., $C_{1-4}$ alkylamino group such as methylamino, ethylamino, propylamino etc.), di-lower alkylamino group (e.g., di-$C_{1-4}$ alkylamino such as dimethylamino, diethylamino etc.), $C_{1-4}$ alkanoylamino group (e.g., acetamide, propionamide etc.) and the like.

Examples of the acyl group include alkanoyl group (e.g., $C_{1-6}$ alkanoyl such as formyl, acetyl, propionyl etc.), alkylsulfonyl group (e.g., $C_{1-4}$ alkylsulfonyl such as methylsulfonyl, ethylsulfonyl etc.), arylsulfonyl group (e.g., benzenesulfonyl, p-toluenesulfonyl etc.), carbamoyl group optionally having substituents (e.g., mono- or di-$C_{1-10}$ alkylcarbamoyl group such as methylcarbamoyl, ethylcarbamoyl, dimethylcarbamoyl, diethylcarbamoyl etc., mono- or di-$C_{6-14}$ arylcarbamoyl such as phenylcarbamoyl, diphenylcarbamoyl etc., mono- or di-$C_{7-16}$ aralkylcarbamoyl group such as benzylcarbamoyl, dibenzylcarbamoyl etc., and the like), sulfamoyl group optionally having substituents (e.g., mono- or di-$C_{1-10}$ alkylsulfamoyl group such as methylsulfamoyl, ethylsulfamoyl, dimethylsulfamoyl, diethylsulfamoyl etc., mono- or di-$C_{6-14}$ arylsulfamoyl group such as phenylsulfamoyl, diphenylsulfamoyl etc., mono- or di-$C_{7-16}$ aralkylsulfamoyl group such as benzylsulfamoyl, dibenzylsulfamoyl etc., and the like), lower alkoxy-carbonyl group (e.g., $C_{1-4}$ alkoxy-carbonyl group such as methoxycarbonyl, ethoxycarbonyl, butoxycarbonyl etc., and the like) and the like.

Examples of the halogen atom include fluorine, chlorine, bromine and iodine.

The methylenedioxy group optionally having substituents are substituted at the two adjacent carbons of the benzene ring, and examples thereof include, besides non-substituted methylenedioxy group, and said methylene group substituted by, for example, halogen (e.g., fluorine atom, chlorine atom, bromine atom, iodine), nitro group, hydroxy group, amino group and the like.

When ring A has a substituent, preferable examples thereof include halogen atom, alkyl group and alkoxy group. Particularly preferable examples of the ring A include non-substituted one and one having chlorine atom and/or methoxy group as substituent. The positions of substitution are 2-position, 4-position, and 2-, 4-positions.

As a preferable example of $R^{10}$ and $R^{11}$, a case where both and $R^{12}$ are methyl groups and a case where $R^{10}$ and $R^{11}$ are bonded to show tetramethylene group are mentioned. Examples of the hydrocarbon group optionally having substituents, which is represented by $R^{10}$ and $R^{11}$, include, besides non-substituted $C_{1-4}$ alkyl group such as methyl, ethyl, propyl and the like, these having substituents such as $C_{2-5}$ alkanoyl such as acetyl, propionyl etc., carboxyl, $C_{1-4}$ alkoxy-carbonyl group (e.g., methoxycarbonyl, ethoxycarbonyl, butoxycarbonyl etc.) and the like, at optional positions and the like.

Examples of the halogen atom represented by $R^{10}$ and $R^{11}$ include fluorine atom, chlorine atom, bromine atom, iodine atom and the like.

When $R^{10}$ and $R^{11}$ in combination show an alkylene group optionally having substituents, examples of the "alkylene group optionally having substituents" include non-substituted alkylene having 2 to 5 carbon atoms (dimethylene, trimethylene, tetramethylene, pentamethylene), these alkylene having, at optional positions, substituents such as lower alkyl group (e.g., $C_{1-4}$ alkyl such as methyl, ethyl, propyl etc.), lower alkoxy group (e.g., $C_{1-4}$ alkoxy such as methoxy, ethoxy, propoxy etc.), hydroxy group, amino group, nitro group, halogen atom (e.g., fluorine, chlorine, bromine, iodine) and the like.

Examples of the lower alkyl group optionally having substituents, which is represented by $R^{12}$, include, besides linear or branched non-substituted $C_{1-6}$ alkyl group such as methyl, ethyl, n-propyl, isopropyl, n-butyl, isobutyl, sec-butyl, tert-butyl, pentyl, hexyl etc., such alkyl group substituted by $C_{1-6}$ alkanoyl (e.g., acetyl, propionyl etc.), carboxyl, $C_{1-4}$ alkoxy-carbonyl (e.g., methoxycarbonyl, ethoxycarbonyl, butoxycarbonyl etc.), and the like, and the like.

Examples of the aryl group optionally having substituents, which is represented by $R^{12}$, include, besides aryl group having 6 to 10 carbon atoms such as non-substituted phenyl group, naphthyl group etc., such aryl group having substituents such as lower alkyl group (e.g., $C_{1-4}$ alkyl such as methyl, ethyl, propyl etc.), lower alkoxy group (e.g., $C_{1-4}$ alkoxy such as methoxy, ethoxy, propoxy etc.), hydroxy group, amino group, nitro group, halogen atom (e.g., fluorine atom, chlorine atom, bromine atom, iodine) and the like at optional positions.

As $R^{12}$, methyl and ethyl are particularly preferable.

As the $C_{2-4}$ alkylene optionally having substituents, which is represented by Alk, alkylene group optionally having substituents, which is formed by $R^{10}$ and $R^{11}$ in combination, wherein the alkylene moiety has 2 to 4 carbon atoms, is mentioned.

Ring B and ring C are each an aromatic ring optionally having substituents, which has 1 to 5, preferably 1 or 2, substituents at optional positions. Examples of the aromatic ring include benzene ring, naphthalene ring and the like and examples of the substituent include lower alkyl group, lower alkenyl group, lower alkoxy group, lower alkylthio group, halogen atom, cyano group and the like. Examples of the "lower alkyl group" include $C_{1-6}$ alkyl group such as methyl, ethyl, propyl, isopropyl, butyl, pentyl and hexyl group, examples of the "lower alkenyl group" include $C_{2-6}$ alkenyl group such as vinyl, 1-propenyl, allyl, isopropenyl, butenyl etc., examples of the "lower alkoxy group" include $C_{1-6}$ alkoxy group such as methoxy, ethoxy, propoxy, isopropoxy, butoxy and the like. Examples of the "lower alkylthio group" include $C_{1-7}$ alkylthio group such as methylthio, ethylthio, propiothio, benzylthio etc. and examples of the halogen atom include chlorine, bromine and the like. Preferable examples of the ring B and ring C include, besides non-substituted naphthalene ring, naphthalene ring having methyl group and/or methoxy group as substituents.

Examples of the hydrocarbon group of the "hydrocarbon group optionally having substituents", which is represented by $R^{13}$ and $R^{14}$, include aliphatic chain hydrocarbon group, alicyclic hydrocarbon group and the like.

Examples of the aliphatic chain hydrocarbon group include linear or branched aliphatic hydrocarbon such as alkyl group, alkenyl group, alkynyl group and the like. Examples of the alkyl group include $C_{1-10}$ alkyl groups such as methyl, ethyl, n-propyl, isopropyl, n-butyl, isobutyl, sec-butyl, tert-butyl, n-pentyl, isopentyl, neopentyl, tert-pentyl etc., and the like. It is preferably lower $C_{1-6}$ alkyl group. Examples of the alkenyl group include $C_{2-6}$ alkenyl groups such as vinyl, allyl, isopropenyl, 2-methylallyl, 1-propenyl, 2-propenyl, 2-methyl-1-propenyl, 1-butenyl, 2-butenyl, 3-butenyl, 2-ethyl-1-butenyl, 2-methyl-2-butenyl, 3-methyl-2-butenyl, 1-pentenyl, 1-hexenyl etc., and the like. Examples of the alkynyl group include $C_{2-6}$ alkynyl groups such as ethynyl, 1-propynyl, 2-propynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl etc., and the like.

Examples of the alicyclic hydrocarbon group include saturated or unsaturated alicyclic hydrocarbon groups such as cycloalkyl group, cycloalkenyl group, cycloalkanedienyl group and the like. Examples of the cycloalkyl group include $C_{3-9}$ cycloalkyl groups such as cyclopropyl, cyclobutyl, cyclohexyl, cycloheptyl, cyclooctyl, cyclononyl, 1-adamantyl group etc., and the like. Examples of the cycloalkenyl group include $C_{3-6}$ cycloalkenyl groups such as 1-cyclopenten-1-yl, 2-cyclopenten-1-yl, 3-cyclopenten-1-yl, 2-cyclohexan-1-yl, 3-cyclohexan-1-yl, 1-cyclobuten-1-yl etc., and the like. Examples of the cycloalkadienyl group include $C_{4-6}$ cycloalkadienyl groups such as 2,4-cyclopentadien-1-yl, 2,4-cyclohexadien-1-yl, 2,5-cyclohexadien-1-yl etc., and the like.

Examples of the heterocyclic group of the "heterocyclic s group optionally having substituents", which is represented by $R^{13}$ and $R^{14}$, include aromatic heterocyclic group, saturated or unsaturated non-aromatic heterocyclic group (aliphatic heterocyclic group) and the like, which contain, as an atom constituting the ring (ring atom), at least 1 (preferably 1 to 4, more preferably 1 or 2) of 1 to 3 kinds (preferably 1 or 2 kinds) of heteroatoms selected from oxygen atom, sulfur atom, nitrogen atom and the like.

Examples of the "aromatic heterocyclic group" include 5 or 6-membered aromatic heteromonocyclic group such as aromatic heteromonocyclic group (e.g., furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl etc.) and the like and 8 to 12-membered aromatic fused heterocyclic group such as aromatic fused heterocyclic group (e.g., benzofuranyl, isobenzofuranyl, benzothienyl, indolyl, isoindolyl, 1H-indazolyl, benzindazolyl, benzoxazolyl, 1,2-benzoisoxazolyl, benzothiazolyl, 1,2-benzoisothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, a-carbolinyl, acridinyl, phenoxazinyl, phenothiazinyl, phenazinyl, phenoxathiinyl, thianthrenyl, phenanthridinyl, phenanthrolinyl, indolizinyl, pyrrolo[1,2-b]pyridazinyl, pyrazolo[1,5-a]pyridyl, imidazo[1,2-b]pyridyl, imidazo[1,5-b]pyridyl, imidazo[1,2-a]pyridazinyl, imidazo[1,2-a]pyrimidinyl, 1,2,4-triazolo[4,3-a]pyridyl, 1,2,4-triazolo[4,3-b]pyridazinyl etc.) and the like, with preference given to heterocyclic ring obtained by condensation of the aforementioned 5 to 6-membered aromatic heteromonocyclic group with benzene ring or heterocyclic ring obtained by condensation of the same or different two heterocyclic rings of the aforementioned 5 or 6-membered aromatic heteromonocyclic group) and the like.

Examples of the "non-aromatic heterocyclic group" include 3 to 8-membered (preferably 5 or 6-membered) saturated or unsaturated (preferably saturated) non-aromatic heterocyclic group (aliphatic heterocyclic group) such as oxiranyl, azetidinyl, oxetanyl, thietanyl, pyrrolidinyl, tetrahydrofuryl, thiolanyl, piperidyl, tetrahydropyranyl, morpholinyl, thiomorpholinyl, piperazinyl etc. and the like. As the substituent that the "heterocyclic group optionally having substituents" as a substituent may have, lower alkyl group (e.g., $C_{1-6}$ alkyl group such as methyl, ethyl, propyl etc., and the like), acyl group (e.g., $C_{1-6}$ alkanoyl such as formyl, acetyl, propionyl, pivaloyl etc., benzoyl and the like), and the like are mentioned.

Examples of the substituent of the "hydrocarbon group optionally having substituents" and "heterocyclic group optionally having substituents", which are represented by $R^{13}$ or $R^{14}$, include aryl group optionally having substituents, cycloalkyl group optionally having substituents, cycloalkenyl group optionally having substituents, alkyl group optionally having substituents, alkenyl group optionally having substituents, alkynyl group optionally having substituents, heterocyclic group optionally having substituents, amino group optionally having substituents, imidoyl group optionally having substituents, amidino group optionally having substituents, hydroxy group optionally having substituents, thiol group optionally having substituents, optionally esterified or amidated carboxyl group, thiocarbamoyl group optionally having substituents, halogen atom (e.g., fluorine, chlorine, bromine, iodine), cyano group, nitro group, acyl group derived from sulfonic acid, acyl group derived from carboxylic acid and the like, wherein the number of these optional substituents present at substitutable positions is 1 to 5, preferably 1 to 3.

Examples of the aryl group of the "aryl group optionally having substituents" as a substituent include $C_{6-14}$ aryl group such as phenyl, naphthyl, anthryl, phenanthryl, acenaphthylenyl etc., and the like. Examples of the substituent of the aryl group here include lower alkoxy group (e.g., $C_{1-6}$ alkoxy group such as methoxy, ethoxy, propoxy etc., and the like), halogen atom (e.g., fluorine, chlorine, bromine, iodine), lower alkyl group (e.g., $C_{1-6}$ alkyl group such as methyl, ethyl, propyl etc., and the like), amino group, hydroxy group, cyano group, amidino group and the like, wherein the number of these optional substituents present at substitutable positions is 1 or 2.

Examples of the cycloalkyl group of the "cycloalkyl group optionally having substituents" as a substituent include $C_{3-7}$ cycloalkyl group such as cyclopropyl, cyclobutyl, cyclopentyl, cyclohexyl, cycloheptyl etc., and the like. Examples of the substituent of the cycloalkyl group here include those similar in number and kind to the substituents of the aforementioned "aryl group optionally having substituents".

Examples of the cycloalkenyl group of the "cycloalkenyl group optionally having substituents" as a substituent include $C_{3-6}$ cycloalkenyl group such as cyclopropenyl, cyclobutenyl, cyclopentenyl, cyclohexenyl etc., and the like. Examples of the substituent of the cycloalkenyl group optionally having substituents here include those similar in number and kind to the substituents of the aforementioned "aryl group optionally having substituents".

Examples of the alkyl group of the "alkyl group optionally having substituents" as a substituent include $C_{1-6}$ alkyl such as methyl, ethyl, n-propyl, isopropyl, n-butyl, isobutyl, sec-butyl, tert-butyl, n-pentyl, isopentyl, neopentyl, 1-methylpropyl, n-hexyl, isohexyl, 1,1-dimethylbutyl, 2,2-dimethylbutyl, 3,3-dimethylbutyl, 3,3-dimethylpropyl etc., and the like. Examples of the substituent of the alkyl group include those similar in number and kind to the substituents of the aforementioned "aryl group optionally having substituents".

Examples of the alkenyl group of the "alkenyl group optionally having substituents" as a substituent include $C_{2-6}$ alkenyl group such as vinyl, allyl, isopropenyl, 2-methylallyl, 1-propenyl, 2-methyl-1-propenyl, 1-butenyl, 2-butenyl, 3-butenyl, 2-ethyl-1-butenyl, 2-methyl-2-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, 5-hexenyl etc., and the like. Examples of the substituent of the alkenyl group here include those similar in number and kind to the substituents of the aforementioned "aryl group optionally having substituents".

Examples of the alkynyl group of the "alkynyl group optionally having substituents" as a substituent include $C_{2-6}$ alkynyl groups such as ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and the like. Examples of the substituents of the alkynyl group here include those similar in number and kind to the substituents of the aforementioned "aryl group optionally having substituents".

Examples of the "heterocyclic group optionally having substituents" as a substituent include those mentioned as the heterocyclic group of the "heterocyclic group optionally having substituents" represented by $R^{13}$ and $R^{14}$, and examples of the substituent include alkyl group optionally substituted by 1 to 5 halogen atoms (e.g., fluorine, chlorine, bromine, iodine), which is exemplified by $C_{1-4}$ alkyl group such as methyl, ethyl, propyl etc., $C_{1-4}$ alkyl group substituted by halogen, such as 2,2,2-trifluoroethyl, 2,2,3,3,3-pentafluoropropyl and the like, $C_{1-3}$ alkoxy group such as methoxy, ethoxy, propoxy, isopropoxy and the like, halogen atom such as chlorine atom, fluorine atom and the like, hydroxy group, amino group, nitro group and the like, which may be present in the number of 1 to 3 at substitutable positions of the heterocyclic group.

Examples of the substituent of the "amino group optionally having substituents", "imidoyl group optionally having substituents", "amidino group optionally having substituents", "hydroxy group optionally having substituents" and "thiol group optionally having substituents" as substituents include lower alkyl group (e.g., $C_{1-6}$ alkyl group such as methyl, ethyl, propyl, isopropyl, butyl, isobutyl, tert-butyl, pentyl, hexyl etc., and the like), acyl group ($C_{1-6}$ alkanoyl (e.g., formyl, acetyl, propionyl, pivaloyl etc.), benzoyl etc.), optionally halogenated $C_{1-6}$ alkoxy-carbonyl (e.g., trifluoromethoxycarbonyl, 2,2,2-trifluoroethoxycarbonyl, trichloromethoxycarbonyl, 2,2,2-trichloroethoxycarbonyl etc.) and the like. The "amino group" of the "amino group optionally having substituents" as a substituent may be substituted by imidoyl group optionally having substituents (e.g., $C_{1-6}$ alkylimidoyl, formylimidoyl, amidino etc.) and the like, or two substituents, in combination with nitrogen atom, may form a cyclic amino group. In this case, examples of the cyclic amino group include 3 to 8-membered (preferably 5 or 6-membered) cyclic amino such as 1-azetidinyl, 1-pyrrolidinyl, piperidino, morpholino, 1-piperazinyl and 1-piperazinyl optionally having, at the 4-position, lower alkyl group (e.g., $C_{1-6}$ alkyl group such as methyl, ethyl, propyl, isopropyl, butyl, tert-butyl, pentyl, hexyl etc., and the like), aralkyl group (e.g., $C_{7-10}$ aralkyl group such as benzyl, phenethyl etc., and the like), aryl group (e.g., $C_{6-10}$ aryl group such as phenyl, 1-naphthyl, 2-naphthyl etc., and the like) and the like, and the like.

Examples of the "optionally esterified carboxyl group" include, besides free carboxyl group, lower alkoxycarbonyl group, aryloxycarbonyl group, aralkyloxycarbonyl group and the like.

Examples of the "lower alkoxycarbonyl group" include $C_{1-6}$ alkoxy-carbonyl group such as methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, isopentyloxycarbonyl, neopentyloxycarbonyl etc., and the like. Of these, $C_{1-3}$ alkoxy-carbonyl group such as methoxycarbonyl, ethoxycarbonyl, propoxycarbonyl etc., and the like are preferable.

Preferable examples of the "aryloxycarbonyl group" include $C_{7-12}$ aryloxy-carbonyl group such as phenoxycarbonyl, 1-naphthoxycarbonyl, 2-naphthoxycarbonyl etc., and the like.

Preferable examples of the "aralkyloxycarbonyl group" include $C_{7-10}$ aralkyloxycarbonyl group such as benzyloxycarbonyl, phenethyloxycarbonyl etc., and the like (preferably $C_{6-10}$ aryl-$C_{1-4}$ alkoxycarbonyl etc.).

The "aryloxycarbonyl group" and "aralkyloxycarbonyl group" may have a substituent, and examples of the substituent include those similar in number and kind to the substituents of aryl group and aralkyl group as an example of the substituent of the N-monosubstituted carbamoyl group to be mentioned below.

The "lower alkoxycarbonyl group" here may have substituents, and examples of the substituent include those similar in number and kind to the substituents of the aforementioned "aryloxycarbonyl group" and "aralkyloxycarbonyl group".

Examples of the substituent of the "thiocarbamoyl group optionally having substituents" include those similar to the substituents of the "carbamoyl group optionally having substituents" to be mentioned below.

Examples of the "optionally amidated carboxyl group" include carbamoyl group optionally having substituents, such as, besides non-substituted carbamoyl, N-monosubstituted carbamoyl group and N,N-disubstituted carbamoyl group.

The "N-monosubstituted carbamoyl group" means a carbamoyl group having one substituent on a nitrogen atom. Examples of the substituent include lower alkyl group (e.g., $C_{1-6}$ alkyl group such as methyl, ethyl, propyl, isopropyl, butyl, isobutyl, tert-butyl, pentyl, hexyl etc., and the like), cycloalkyl group (e.g., $C_{3-6}$ cycloalkyl group such as cyclopropyl, cyclobutyl, cyclopentyl, cyclohexyl etc., and the like), aryl group (e.g., $C_{6-10}$ aryl group such as phenyl, 1-naphthyl, 2-naphthyl etc., and the like), aralkyl group (e.g., $C_{7-10}$ aralkyl group such as benzyl, phenethyl etc., preferably phenyl-$C_{1-4}$ alkyl group and the like), heterocyclic group (e.g., those similar to the aforementioned "heterocyclic group" as the substituent of the "hydrocarbon group optionally having substituents", which is represented by $R^{13}$, and the like) and the like. The lower alkyl group, cycloalkyl group, aryl group, aralkyl group and heterocyclic group may have a substituent, and examples of the substituent include hydroxy group, amino group optionally having substituents [said amino group optionally has, as a substituent, 1 or 2 from, for example, lower alkyl group (e.g., $C_{1-6}$ alkyl group such as methyl, ethyl, propyl, isopropyl, butyl, isobutyl, tert-butyl, pentyl, hexyl etc., and the like), acyl group (e.g., $C_{1-6}$ alkanoyl such as formyl, acetyl, propionyl, pivaloyl etc., benzoyl and the like) and the like], halogen atom (e.g., fluorine, chlorine, bromine, iodine), nitro group, cyano group, lower alkyl group optionally substituted by 1 to 5 halogen atoms (e.g., fluorine, chlorine, bromine, iodine), lower alkoxy group optionally substituted by 1 to 5 halogen atoms (e.g., fluorine, chlorine, bromine, iodine), and the like.

Examples of the lower alkyl group include $C_{1-6}$ alkyl group such as methyl, ethyl, n-propyl, isopropyl, n-butyl, isobutyl, sec-butyl, tert-butyl, pentyl, hexyl etc., and the like, particularly methyl, ethyl and the like are preferable. Examples of the lower alkoxy group include $C_{1-6}$ alkoxy group such as methoxy, ethoxy, n-propoxy, isopropoxy, n-butoxy, isobutoxy, sec-butoxy, tert-butoxy etc., and the like, particularly preferably methoxy, ethoxy and the like. These substituents are the same or different and preferably present in the number of 1 or 2 or 3 (preferably 1 or 2).

The "N,N-disubstituted carbamoyl group" means a carbamoyl group having 2 substituents on the nitrogen atom, wherein one of the substituents is exemplified by those similar to the substituent of the above-mentioned "N-monosubstituted carbamoyl group", and the other substituent is exemplified by lower alkyl group (e.g., $C_{1-6}$ alkyl group such as methyl, ethyl, propyl, isopropyl, butyl, tert-butyl, pentyl, hexyl etc., and the like), $C_{3-6}$ cycloalkyl group (e.g., cyclopropyl, cyclobutyl, cyclopentyl, cyclohexyl and the like), C aralkyl group (e.g., benzyl, phenethyl etc., preferably phenyl-$C_{1-4}$ alkyl group etc.) and the like. Two substituents may form a cyclic amino group together with a nitrogen atom, and examples of the cyclic aminocarbamoyl group in this case include 1-azetidinylcarbonyl, 1-pyrrolizinylcarbonyl, piperidinocarbonyl, morpholinocarbonyl, 1-piperazinylcarbonyl and 3 to 8-membered (preferably 5 or 6-membered) cyclic aminocarbonyl such as 1-piperazinylcarbonyl optionally having, at the 4-position, lower alkyl group (e.g., $C_{1-6}$ alkyl group such as methyl, ethyl, propyl, isopropyl, butyl, tert-butyl, pentyl, hexyl etc., and the like), aralkyl group (e.g., $C_{7-10}$ aralkyl group such as benzyl, phenethyl etc., and the like), aryl group (e.g., $C_{6-10}$ aryl group such as phenyl, 1-naphthyl, 2-naphthyl etc., and the like), and the like, and the like.

Examples of the "acyl group derived from sulfonic acid" as a substituent include one obtained by bonding the one substituent that the aforementioned "N-monosubstituted carbamoyl group" has on the nitrogen atom to sulfonyl, and the like. Preferably, it is an acyl such as $C_{1-6}$ alkylsulfonyl (e.g., methylsulfonyl, ethylsulfonyl etc.).

Examples of the "acyl group derived from carboxylic acid" as a substituent include one obtained by bonding hydrogen atom or the one substituent that the aforementioned "N-monosubstituted carbamoyl group" has on the nitrogen atom to the carbonyl, and the like. Preferably, it is an acyl such as $C_{1-6}$ alkanoyl (e.g., formyl, acetyl, propionyl, pivaloyl etc.), benzoyl and the like.

As $R^{13}$ and $R^{14}$, alkyl groups and cycloalkyl groups are preferable. Particularly preferably, a compound substituted by either tert-butyl or 1-adamantyl and methyl on the ring A of compound (V) is subjected to an asymmetric hydrogenation reaction. In addition, these groups may be substituted by the above-mentioned substituents. That is, a compound represented by the chemical formula:

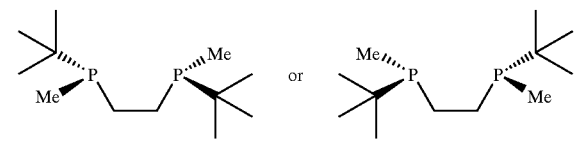

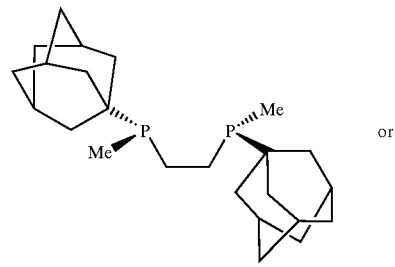

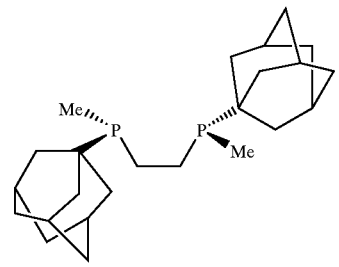

is preferable, particularly, a compound represented by

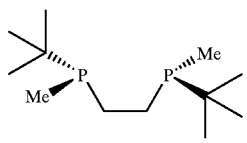

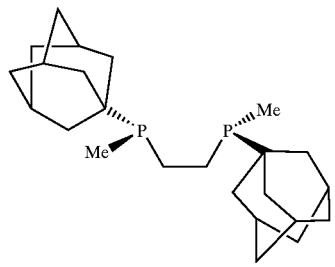

is preferable.

Of the compounds represented by the formulas (IIa), (II), (V), (VI) and (VII), a compound having an acidic group or basic group may form a salt. When a compound has an acidic group, it may form a salt with, for example, a metal (e.g., sodium, potassium, calcium etc.) or an ammonium ion. When it has a basic group, the compound may form an acid addition salt, such as an inorganic acid salt (e.g., hydrochloride, sulfate, hydrobromate, phosphate etc.), an organic acid salt (e.g., acetate, trifluoroacetate, succinate, maleate, fumarate, propionate, citrate, tartrate, lactate, oxalate, methanesulfonate, p-toluenesulfonate etc.) and the like.

Throughout the specification, of the compounds shown by the formulas (I), (IIa), (II), (V), (VI) and (VII), and salts thereof are referred to as compound (symbol of formula). For example, a compound of formula (I) and a salt thereof are sometimes simply referred to as compound (I).

According to the method of the present invention (1), compound (I) and an optically active form of compound (II) or (III) (hereinafter sometimes to be referred to as a resolution reagent) are reacted in a suitable solvent to give a diastereomer salt of compound (IVb) or (IVb). The compound (I) may be a racemate containing equivalent amounts of an (S)-compound and an (R)-compound, or a mixture containing either optical isomer in an amount exceeding the equivalent amount. The optically active form of compound (II) and (III) includes an (S)-compound and an (R)-compound.

The amount of the resolution reagent to be used is preferably 0.1–2 times, preferably 0.6–1.2 times, the mol amount relative to compound (I). In this case, mineral acid such as hydrochloric acid, sulfuric acid, phosphoric acid and the like, or organic acid such as acetic acid, propionic acid, fumaric acid, maleic acid and the like may be co-used with the resolution reagent to achieve said molar ratio. Two or more resolution reagents may be used simultaneously.

The solvent to be used is preferably one that dissolves compound (I) and resolution reagent, does not chemically change these compounds and in which one of the produced diastereomer salt is sparingly soluble. For example, water, alcohols such as methanol, ethanol, isopropanol etc., ethers such as diethyl ether, diisopropyl ether, tetrahydrofuran, tetrahydropyran etc., ketones such as acetone, 2-butanone etc., and nitriles such as acetonitrile etc., which may be used alone or in combination of two or more kinds thereof. The amount to be used is generally 1 to 100-fold amount, preferably 1 to 50-fold amount, relative to (I). The temperature is generally within the range of not less than 15° C. and not higher than the boiling point of the solvent used.

After forming a diastereomer salt, cooling or concentration allows crystallization of either salt. Depending on the conditions, standing at room temperature without cooling or concentration may result in easy precipitation of a sparingly soluble salt.

The crystallized salt can be easily separated by a general solid-liquid separation method such as filtration, centrifugal separation and the like. The crystals of the separated salt can be made to have a high purity as necessary by a method known per se such as recrystallization and the like.

The mother liquor after separation of a sparingly soluble salt may contain, as it is, an easily soluble salt alone and as it is or may be cooled after concentration to separate an easily soluble salt.

The thus-obtained salt can be decomposed by any known method. For example, a treatment with an alkali or acid in a water-soluble solution achieves the object. Examples of the alkali include hydroxide of alkali metal or alkaline earth metal such as sodium hydroxide, potassium hydroxide, calcium hydroxide, barium hydroxide and the like, alkali metal carbonate or hydrogen carbonate such as sodium carbonate, potassium carbonate, sodium hydrogen carbonate, potassium hydrogen carbonate and the like, and organic base such as ammonia, pyridine and the like. Examples of the acid include mineral acid such as hydrochloric acid, sulfuric acid, phosphoric acid and the like, and organic acids such as trifluoroacetic acid, trifluoromethanesulfonic acid and the like. Generally, the salt can be treated with a water-soluble base such as aqueous sodium hydroxide solution, aqueous potassium hydroxide solution, aqueous ammonia solution and the like and the liberated optically active naphthalene derivative is subjected to, for example, a solid-liquid separation such as filtration and centrifugal separation, or extraction step with an organic solvent and the like to give an optically active form of the objective compound (I). The treatment with a base is generally carried out at about −10 to 25° C. and the amount of the base to be used is 1 to 5-fold molar amount relative to salt. The base concentration is 1–50 wt %, preferably 5–20 wt %.

When a basic aqueous layer after extraction of a naphthalene derivative is made acidic with an acid such as hydrochloric acid, sulfuric acid and the like, an optically active form of compound (II) or an optically active form of compound (III) used as a resolution reagent may be recovered and used again.

A naphthalene derivative represented by the formula (I), which is used as a starting material in the present invention, can be produced according to the method described in the following.

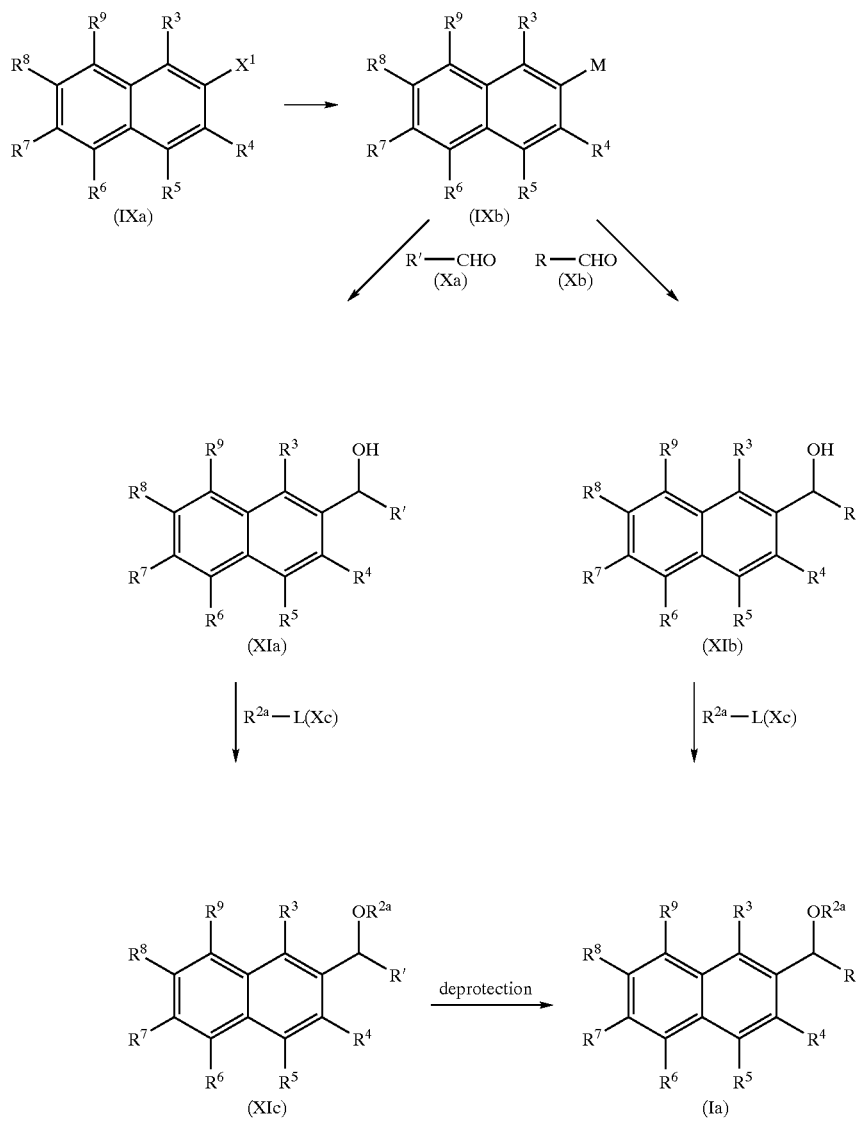

wherein $X^1$ is a halogen atom such as chlorine, bromine, iodine and the like, M is a metal atom (lithium, magnesium, metal halide such as magnesium chloride, magnesium bromide etc., and the like, L is a leaving group [$C_{1-6}$-alkylsulfonyloxy group (e.g., methylsulfonyloxy, ethylsulfonyloxy etc.), $C_{6-10}$ arylsulfonyloxy group (e.g., benzenesulfonyloxy, ortho-, meta-, or para-toluenesulfonyloxy, ortho-, meta-, or para-nitrobenzenesulfonyloxy and the like), $R^{2a}$ is a lower alkyl group optionally having substituents, R' is an optionally substituted nitrogen-containing heterocyclic group having a protecting group, and other symbols are as defined above.

The optionally substituted nitrogen-containing heterocyclic group of the "optionally substituted nitrogen-containing heterocyclic group having a protecting group" represented by R' is the same as those represented by R above, and examples of the protecting group are as mentioned below.

The compound (IXa) is reacted with alkyl lithium, metal magnesium and the like to convert the compound to an organic metal compound (IXb), and then subsequently reacted with aldehyde compound (Xb) or (Xa) to give compound (XIa) or (XIb), respectively. Examples of the alkyl lithium to be used include $C_{1-4}$ alkyl lithium such as n-butyl lithium, s-butyl lithium and the like. The amount of use thereof is 1 mol to 3-fold molar amount, preferably 1 to 1.5-fold molar amount, relative to 1 mol of the starting material compound (IXa). The reaction temperature at which alkyl lithium is reacted is from −100° C. to 0° C., preferably from −80° C. to −20° C. When metal magnesium is to be reacted, the reaction temperature is −20° C. to 100° C., preferably 10° C. to 50° C. The reaction time is from about 5 minutes to 20 hours. This reaction is generally carried out in an organic solvent inert to the reaction. Examples of the organic solvent that does not adversely affect the reaction include ethers such as diethyl ether, dioxane, tetrahydrofuran (THF) and the like, saturated hydrocarbons such as hexane, pentane and the like, halogenated hydrocarbons such as dichloromethane, chloroform and the like, aromatic hydrocarbons such as benzene, toluene and the like, and the like, which are used in admixture of one or more kinds thereof at a suitable mixing ratio. The aldehyde compound (Xb) or (Xa) is used in an amount of 0.5 equivalent amount to 10 equivalent amounts, preferably 0.5 to 1.5 equivalent amount, relative to compound (IXb).

The compound (XIa) and (XIb) are alkylated by a conventional method to give compound (XIc) and (Ia), respectively. The alkylation reagent (Xc) to be used is, for example, alkyl halide (e.g., methyl iodide, ethyl bromide, isopropyl bromide etc.), alkyl or arylsulfonic acid ester (e.g., methyl methanesulfonate, ethyl p-toluenesulfonate etc.) and the like. The amount of use thereof is 1 to 10 equivalent amount, preferably 1 to 2 equivalent amount, relative to compound (XIa) or (XIb). This reaction is generally carried out under basic conditions. Examples of the base to be used are sodium hydride, potassium carbonate, sodium methylate and the like. This reaction is generally carried out in a solvent inert to the reaction. Examples of such solvent include ethers such as dimethylformamide, tetrahydrofuran and the like, halogenated hydrocarbons such as dichloromethane and the like, and the like. While the reaction time varies depending on the activity and amount of alkylating agent, and base, it is generally from 30 minutes to 24 hours, preferably from 30 minutes to 10 hours. The reaction temperature is generally from −20° C. to 150° C.

The protecting group of $R^{1a}$ is removed from compound (XIc) by a method known per se or an analogous method to give compound (Ia). For example, when R' of compound (XIc) has a trityl group, or when a nitrogen-containing heterocyclic ring optionally having substituents is protected by a trityl group, the trityl group can be removed by a treatment under acidic conditions, or hydrogenolysis. Examples of the acid include organic acid such as formic acid, acetic acid and the like, inorganic acid such as hydrochloric acid etc., and the like. It is also possible to use a solvent inert to the reaction, such as alcohols, ethers such as THF etc., and the like. The reaction temperature is generally from 0° C. to 100° C.

tion is generally carried out using manganese dioxide, chromic acid and the like as an oxidant, in a solvent inert to the reaction, such as dichloromethane, chloroform, THF and the like. The reaction time is generally from about 30 minutes to 48 hours, preferably from 30 minutes to 10 hours. The reaction temperature is generally from 0° C. to 100° C., preferably from 20° C. to 70° C.

The compound (XIe) can be obtained by removing the protecting group from compound (XId) by a method known per se or an analogous method. The protecting group can be removed according to the method analogous to the method to obtain compound (Ia) from compound (XIc). Then, compound (XIe) is reacted with an organic metal reagent (Xd) (alkyl lithium reagent such as methyllithium etc., Grignard's reagent such as ethylmagnesium bromide, isopropyl magnesium chloride etc., and the like) to give compound (Ib). This reaction is generally carried out according to a method known per se, such as the method described in Shin Jikken Kagaku Kouza Vol. 14, p. 512 (Maruzen) or a method analogous thereto. In this reaction, the organic metal reagent (Xd) is used in an amount of 1 to 10 equivalents, preferably 1 to 3 equivalents, relative to the ketone compound (XIe). The reaction temperature is from −100° C. to 50° C., preferably from −80° C. to 20° C. The reaction time is from about 5 minutes to 20 hours. This reaction is carried out in an organic solvent generally inert to the reaction. Examples of the organic solvent that does not adversely affect the reaction include ethers such as diethyl ether, dioxane, tetrahydrofuran and the like, saturated hydrocarbons such as hexane, pentane and the like, halogenated hydrocarbons such as dichloromethane, chloroform and the like, aromatic hydrocarbons such as benzene, toluene and the like, and the like, which may be used alone or in combination of 2 or more kinds thereof.

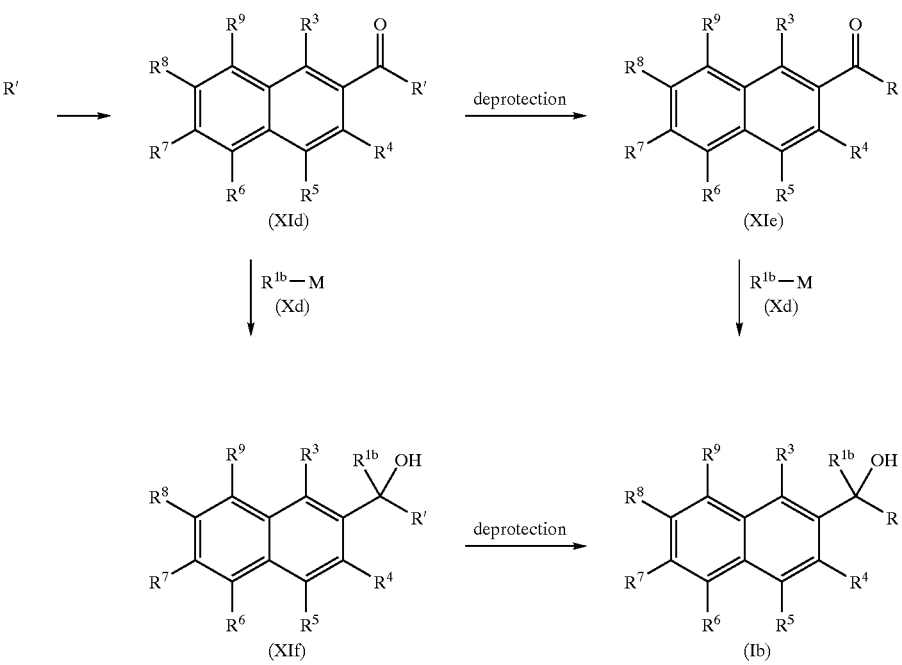

wherein $R^{1b}$ is as defined for $R^1$ except hydrogen atom, and other symbols are as defined above.

The compound (XId) can be obtained by subjecting compound (XIa) to typical oxidization reaction. This reac- The compound (Ib) can be also synthesized by reacting compound (XId) with compound (Xd) to give compound (XIf), which is followed by deprotection.

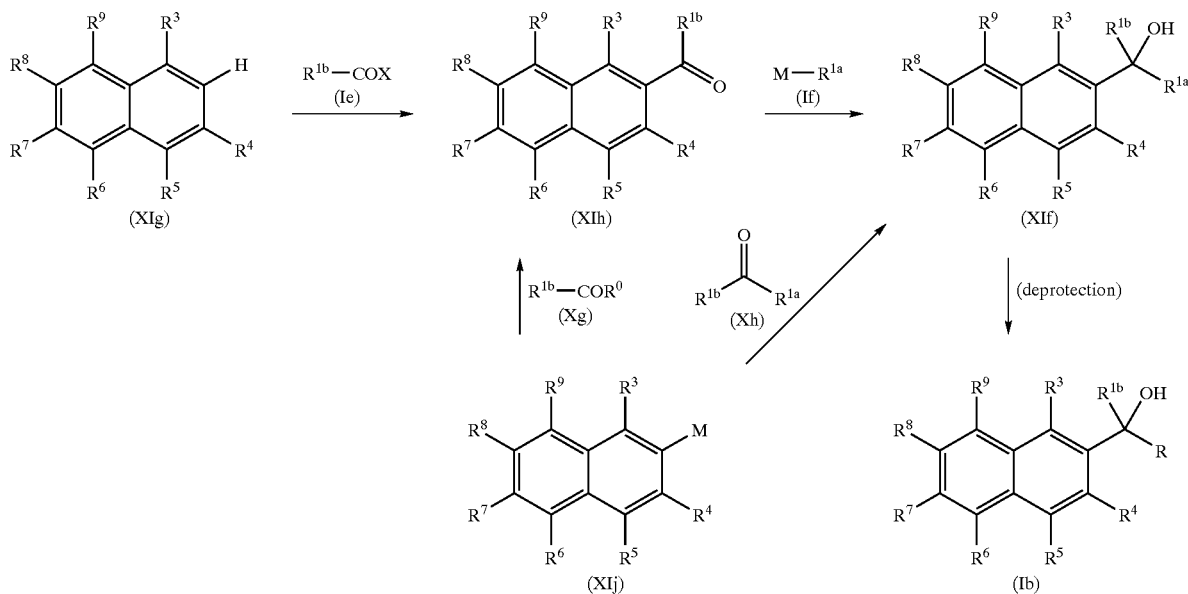

wherein $R^0$ is a group represented by OR" or NR"R'" (R" and R'" are each $C_{1-6}$ alkyl group, or $C_{1-6}$ alkyloxy group and NR"R'" includes cyclic amine residue such as morpholino group, pyrrolidino group and the like), $R^{1a}$ is a nitrogen-containing heterocyclic group optionally having substituents, which may have protecting group, and other symbols are as defined above.

Of the above-mentioned nitrogen-containing heterocyclic group optionally having substituents and protecting group, which is represented by $R^{1a}$, the group having a protecting group is the same as those mentioned with regard to the aforementioned R', and the group not having a protecting group is the same as those mentioned with regard to the aforementioned R.

The compound (XIg) and compound (Xe) are reacted according to Friedel-Crafts reaction known per se, for example, the method described in Shin Jikken Kagaku Kouza Vol. 14, p. 511 (Maruzen) or a method analogous thereto to give carbonyl compound (XIh). The compound (XIh) can be also synthesized by reacting compound (XIj) with compound (Xg). In this reaction, a solvent inert to the reaction, such as THF, dichloromethane and the like, is used and the compound (XIj) is used in an amount of 0.2–2 equivalents, preferably 0.2–1.5 equivalents, relative to compound (Xg). The reaction temperature is from −80° C. to 50° C., preferably from −80° C. to 20° C.

The compound (XIh) is alkylated using compound (Xf) to give compound (XIf). This reaction can be carried out according to the reaction to synthesize compound (Ib) from compound (XIe).

When organic metal reagent (IXb) is reacted with ketone compound (Xh) according to a method analogous to the method for synthesizing compound (Ib) from compound (XIe), compound (XIf) can be synthesized. When the nitrogen-containing heterocyclic ring of compound (XIf) is protected, the protecting group is removed according to a method analogous to the method for synthesizing compound (Ia) to give compound (Ib).

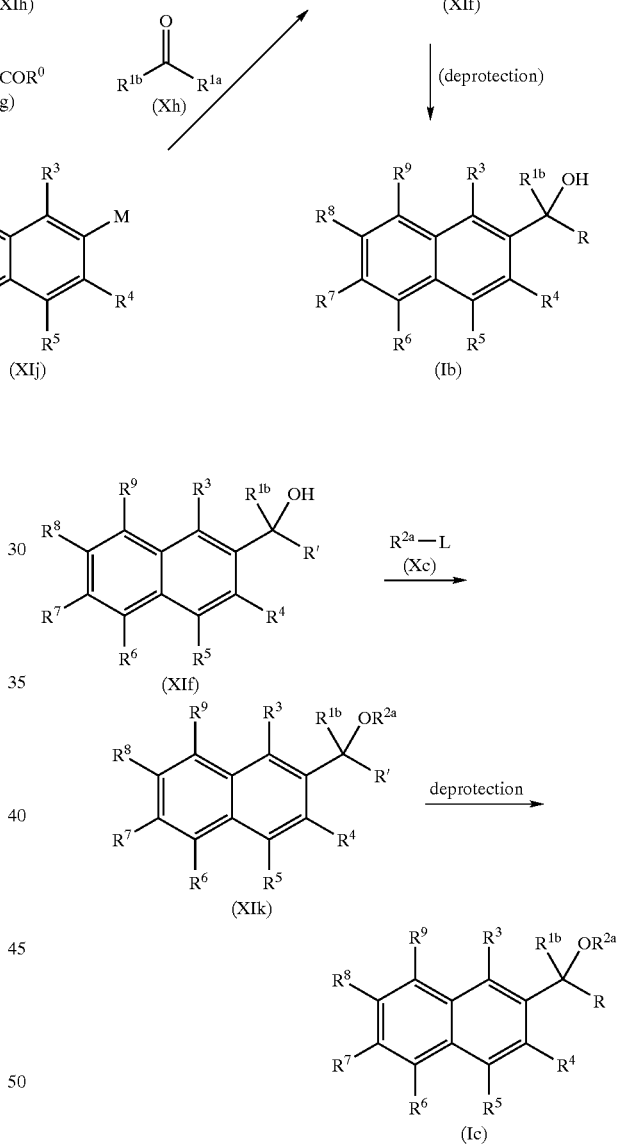

wherein each symbol in the formula is as defined above.

The compound (XIf) is alkylated with (Xc) to give compound (XIk) and the protecting group is removed to give compound (Ic). The alkylation can be carried out according to a method analogous to the method for synthesizing compound (XIc) from compound (XIb). The protecting group can be removed according to a method analogous to the method for synthesizing compound (Ia) from compound (XIc).

Both the (S)-compound and (R)-compound of the optically active compound represented by the formula (II) can be produced according to a known method, such as the method described in The Journal of Organic Chemistry, Vol. 50, pp. 4508–4541 (1985).

The optically active compound represented by the formula (III) can be prepared according to a known method, such as the method described in JP-B-55-47013.

An optically active form of the compound (I) has a superior effect as a pharmaceutical agent, and especially has a superior inhibitory activity against steroid $C_{17,20}$-lyase. The compound (I) is low toxic and causes few side effects. Therefore, compound (I) is useful as, for example, an agent for the prophylaxis or treatment of various diseases, such as (1) primary cancer of malignant tumor (e.g., prostate cancer, breast cancer, uterine cancer, ovarian cancer etc.), and metastasis or recurrence thereof, (2) various symptoms accompany these cancers (e.g., pain, cachexia etc.), (3) prostatic hypertrophy, virilism, hirsutism, male pattern alopecia, precocious puberty, endometriosis, uterus myoma, adenomyosis of uterus, mastopathy, polycystic ovary syndrome etc. in a mammal (e.g., human, bovine, horse, dog, cat, monkey, mouse, rat etc., especially human).

While an optically active form of compound (I) has a superior effect even when used solely, the effect can be further promoted by using the compound in combination with other pharmaceutical preparations and therapies. Examples of the preparation and therapy to be combined include, but are not limited to, sex hormones, alkylating agents, antimetabolites, antitumor antibiotics, plant alkaloids, immunotherapies and the like.

Examples of other therapy include operation, thermotherapy, radiotherapy and the like.

Together with the chemotherapy including administration of compound (I), therapies other than chemotherapies, such as an operation including orchidectomy, thermotherapy, radiotherapy and the like can be conducted.

Examples of the pharmaceutically acceptable carrier include various organic or inorganic carriers conventionally used as materials for pharmaceuticals, which are added in suitable amounts as excipients, lubricants, binders, disintegrators, thickeners for solid preparations; solvents, dispersants, solubilizing agents, suspending agents, isotonic agents, buffer agents, soothing agents for liquid preparations, and the like. Where necessary, additives such as preservatives, antioxidants, coloring agents, sweetening agents etc. can be used. Examples of preferable excipient include lactose, saccharose, D-mannitol, starch, crystalline cellulose, light anhydrous silicic acid and the like. Examples of preferable lubricant include magnesium stearate, calcium stearate, talc, colloidal silica, and the like. Examples of preferable binder include crystalline cellulose, saccharose, D-mannitol, dextrin, hydroxypropylcellulose, hydroxypropylmethylcellulose, polyvinyl pyrrolidone, and the like. Examples of preferable disintegrator include starch, carboxymethylcellulose, calcium carboxymethylcellulose, sodium crosscarmellose, sodium carboxymethyl starch, and the like. Examples of preferable thickener include natural rubbers, cellulose derivatives, acrylate polymers, and the like. Examples of preferable solvent include water for injection, alcohol, propylene glycol, Macrogol, sesame oil, corn oil, and the like. Examples of preferable dispersant include Tween 80, HCO 60, polyethylene glycol, carboxymethylcellulose, sodium alginate, and the like. Examples of preferable solubilizing agent include polyethylene glycol, propylene glycol, D-mannitol, benzyl benzoate, ethanol, trisaminomethane, cholesterol, triethanolamine, sodium carbonate, sodium citrate, and the like. Examples of preferable suspending agent include surfactants, such as stearyl triethanolamine, sodium laurylsulfate, laurylaminopropionic acid, lecithin, benzalkonium chloride, benzethonium chloride, glycerin monostearate etc.; hydrophilic polymer such as polyvinyl alcohol, polyvinyl pyrrolidone, sodium carboxymethyl cellulose, methylcellulose, hydroxymethylcellulose, hydroxyethylcellulose, hydroxypropylcellulose etc.; and the like. Examples of preferable isotonic agent include sodium chloride, glycerin, D-mannitol and the like.

Examples of preferable buffer agent include buffer solution such as phosphate, acetate, carbonate, citrate etc., and the like. Examples of preferable soothing agent include benzyl alcohol, and the like. Examples of preferable preservative include paraoxybenzoates, chlorobutanol, benzyl alcohol, phenethyl alcohol, dehydroacetic acid, sorbic acid, and the like. Examples of preferable antioxidant include sulfurous acid salt, ascorbic acid, and the like.

The pharmaceutical preparation of the present invention can be manufactured by a conventional method. The ratio of compound (I) contained in a pharmaceutical preparation is usually 0.1 to 100% (w/w). Specific examples are shown below.

(1) Tablets, Powder, Granules, Capsules:

These can be produced by adding, for example, excipients, disintegrators, binders, lubricants etc. to compound (I), compression forming the mixture and, where necessary, coating for masking of taste, enteric or sustained release.

(2) Injection:

This can be produced by preparing compound (I) into an aqueous injection together with, for example, dispersants, preservatives, isotonic agents etc., or into an oily injection by dissolving, suspending or emulsifying the compound in a vegetable oil such as olive oil, sesame oil, cotton seed oil, corn oil etc., or propylene glycol etc.

The content of compound (I) admixed in these preparations is usually 0.01 to 50%, though subject to change depending upon the kind of preparations.

While the amount of compound (I) to be contained in the above-mentioned pharmaceutical preparation varies depending upon the compound selected, the kind of animal to be the administration target, administration frequency and the like, the compound proves effective over a broad range. The daily dose of the pharmaceutical preparation of the present invention as an effective amount of compound (I) of the present invention, for example, for in the case of oral administration to an adult patient with a solid tumor (e.g., patient with prostate cancer) is generally about 0.001 to about 500 mg/kg body weight, preferably about 0.1 to about 40 mg/kg body weight, more preferably about 0.5 to about 20 mg/kg body weight. When the compound is parenterally administered or administered concurrently with a different anticancer agent, the dose generally becomes less than those mentioned above. The amount of the compound actually administered is determined according to the selection of compound, dosage form of each preparation, age, body weight and sex of patient, degree of disease, administration route, period and intervals of administration and the like, which can be varied according to the judgment of a doctor.

The administration route of the aforementioned pharmaceutical preparation is free of any particular limitation by various conditions. The preparation can be administered, for example, orally or parenterally. Examples of the "parenteral" used here include intravenous, intramuscular, subcutaneous, intranasal, intradermal, instillation, intracerebral, intrarectal, intravaginal and intraperitoneal administrations, and the like.

The above-mentioned administration term and administration interval vary depending upon various conditions and determined any time by judgment of a doctor. Divided administration, consecutive administration, intermittent administration, high dose short period administration, repeat administration and the like can be employed. For oral administration, for example, the dose is desirably given once a day or divided into several portions (especially two or three doses a day) and administered. Administration of a sustained release preparation or intravenous drip infusion over a long time is also possible.

The compound (IIa) can be produced according to the methods shown in the following Production method 1, Production method 2 and Production method 3. The starting material compound and synthetic intermediate can be subjected to a reaction in the form of a free compound or a salt like compound (IIa), or as a reaction mixture, or after isolation according to a known method.

Production Method 1

First, compound (V) is subjected to asymmetric hydrogenation reaction to give an optically active form, which is then reduced and the obtained compound (VII) is subjected to phosphorylation to give the objective compound.

Production of compound (VI) by asymmetric hydrogenation of compound (V) is performed by hydrogenation in the presence of a complex of an optically active ligand and ruthenium.

A preferable embodiment usable as the optically active ligand in this reaction is bidentate phosphine. As a specific example thereof, structural formulas of one of the optical isomers are shown.

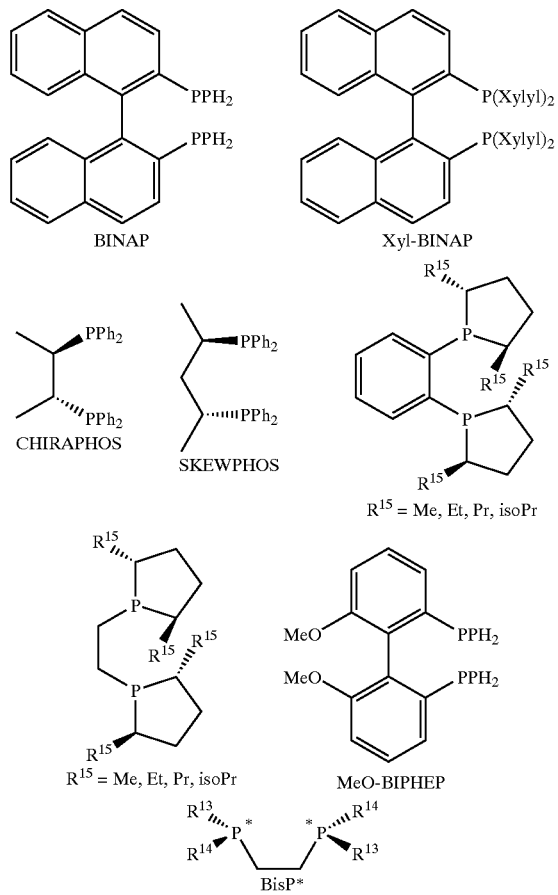

wherein each symbol is as defined above.

Preferably, it is compound (VI) abbreviated as BisP*.

The compound (VIII) exemplified in the above formulas can be produced according to the method described in Journal of the American Chemical Society, Vol. 117, p. 4423 (1995).

For example, the ruthenium complex of compound (VIII) can be obtained by heating compound (VIII) and, for example, 1,5-cyclooctadieneruthenium (2-methylallyl) and the like, in a solvent such as hexane, filtration and concentration to give a solid, which is dissolved again in acetone and the like and treated with hydrobromic acid and the like.

In this reaction, the use of a ruthenium complex of compound (VIII) is preferable. As long as an optically active hydroxy compound can be produced from a keto compound, however, a complex with a transition metal other than ruthenium can be used.

This reaction is carried out generally under pressurization with a hydrogen gas. The hydrogen pressure is generally applied at 0.1 to about 100 kg/cm$^2$, preferably about 1 to about 10 kg/cm$^2$. This reaction is preferably carried out in a solvent. The solvent may be any as long as it does not inhibit the reaction and is exemplified by hydrocarbons such as hexane, pentane and the like, amides such as N,N-dimethylformamide, N,N-dimethylacetamide and the like, aromatic hydrocarbons such as benzene, toluene and the like, aliphatic esters such as ethyl acetate, propyl acetate and the like, ethers such as diethyl ether, diisopropyl ether, tetrahydrofuran and the like, halogenated hydrocarbons such as dichloromethane, chloroform and the like, alcohols such as methanol, ethanol, 2-propanol and the like, sulfoxides such as dimethyl sulfoxide and the like, nitriles such as acetonitrile and the like, water and the like. These solvents can be used alone or as a mixed solvent. Particularly preferably, a mixed solvent of methanol and water is used. The amount of the solvent to be used is generally about 1 to about 1000-fold volume, preferably about 5 to about 100-fold volume, relative to compound (V). The reaction temperature is about 0 to about 200° C., preferably about 10 to about 100° C. The reaction time is from about 10 minutes to about 100 hours, preferably from about 1 hour to about 50 hours. The amount of the ruthenium complex of compound (Xi) to be used is generally about 1/1 to about 1/100,000-fold mol, preferably about 1/10 to about 1/10,000-fold mol, relative to compound (V). The compound (VI) thus obtained can be isolated and purified by a method known per se, such as extraction, pH adjustment, phase transfer, salting-out, crystallization, chromatography and the like. It is also possible to subject the compound as a crude product in the next step.

The compound (VI) can be converted to compound (VII) by reduction. This reaction is carried out according to a method known per se.

The reducing agent includes, for example, metal hydrides such as sodium borohydride, lithium borohydride, lithium aluminum hydride, diisopropyl aluminum hydride, triethyl lithium borohydride and the like, diborane, 9-BBN, catechol borane and the like. The solvent includes, for example, aromatic hydrocarbons such as benzene, toluene, xylene and the like, ethers such as diethyl ether, diisopropyl ether, butylmethyl ether, dioxane, tetrahydrofuran and the like, halogenated hydrocarbons such as chloroform, dichloromethane, ethylene dichloride, carbon tetrachloride and the like, and the like. Depending on the kind of reducing agent, alcohols such as methanol, ethanol, propanol, butanol and the like can be used. Of these, ethers such as diethyl ether, tetrahydrofuran and the like are particularly preferable. These reducing agents are preferably used in an amount of 0.25–10 molar equivalents relative to compound (VI). Preferably, this reaction is generally carried out from −20 to 100° C., more preferably from 0 to 100° C., for 0.5 hour to 50 hours, preferably from 0.5 hour to 24 hours. The compound (VIII) thus obtained can be isolated by separation and purification means known per se, such as concentration, solvent extraction, crystallization, phase transfer, chromatography and the like.

The compound (VII) can be advantageously converted to compound (IIa) by, for example, reaction with phosphoryl chloride, and then alkaline hydrolysis, and neutralization with an acid, as shown in the following formulas.

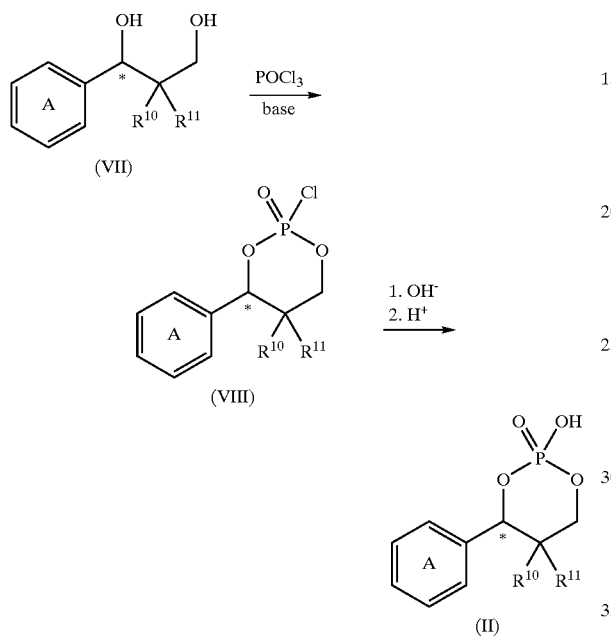

wherein each symbol is as defined above.

The amount of phosphoryl chloride to be used is 1–5 molar equivalents, preferably 1–2 molar equivalents, relative to compound (VII). The solvent includes, for example, aromatic hydrocarbons such as benzene, toluene, xylene and the like, ethers such as diethyl ether, diisopropyl ether, butylmethyl ether, dioxane, tetrahydrofuran and the like, halogenated hydrocarbons such as chloroform, dichloromethane, ethylene dichloride, carbon tetrachloride and the like, and the like. Particularly preferably, halogenated hydrocarbons such as dichloromethane and the like are used. This reaction is carried out at generally from 0 to 150° C., preferably from 20 to 100° C., for 0.5 hour to 50 hours, preferably from 0.5 hour to 10 hours. The chlorides of phosphoric acid thus obtained can be isolated by a separation and purification means known per se, such as concentration, solvent extraction, crystallization, phase transfer, chromatography and the like. It is also possible to subject the compound to the next hydrolysis step as a crude product. The hydrolysis is carried out in the presence of a base, preferably alkali metal hydroxide, sodium hydroxide, potassium hydroxide and the like. The amount of the base to be used is 1 to 20 molar equivalents, preferably 1 to 5 molar equivalents, relative to compound (VII). The solvent includes, for example, aromatic hydrocarbons such as benzene, toluene, xylene and the like, ethers such as diethyl ether, diisopropyl ether, butylmethyl ether, dioxane, tetrahydrofuran and the like, halogenated hydrocarbons such as chloroform, dichloromethane, ethylene dichloride, carbon tetrachloride and the like, alcohols such as methanol, ethanol and the like, water and the like. Particularly preferably, it is water. These may be used alone or as a mixed solvent. This reaction is carried out generally from 0° C. to 200° C., preferably from 50° C. to 150° C., for 0.1 hour to 50 hours, preferably from 0.1 hour to 2 hours.

Neutralization can be performed by adding an acid, such as hydrochloric acid, hydrobromic acid, sulfuric acid and the like. The compound (IIa) thus obtained can be isolated according to a separation and purification means known per se, such as concentration, solvent extraction, crystallization, phase transfer, chromatography and the like.

When, of the compounds (V), $R^{10}$ and $R^{11}$ in combination show an alkylene group optionally having substituents, these compounds can be produced by, as shown in the following formula, reacting compound (V') wherein both $R^{10}$ and $R^{11}$ are hydrogen atoms with compound (Xi) to cycloalkylate the alpha-position carbon of the beta-ketoester.

As shown below

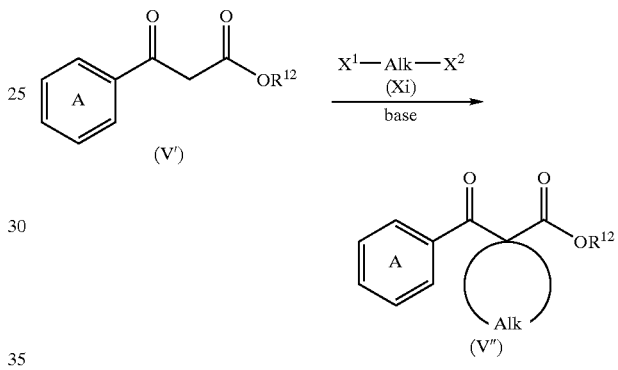

wherein $X^1$ and $X^2$ are the same or different and each is a halogen atom, $C_{1-6}$ alkylsulfonyloxy group or $C_{6-10}$ arylsulfonyloxy group, and other symbols are as defined above, the compound can be produced by cycloalkylating the alpha-position carbon of the beta-ketoester according to a method known per se.

In the above-mentioned formulas, halogen atom represented by $X^2$ is exemplified by chlorine, bromine and iodine, $C_{1-6}$ alkylsulfonyloxy group is exemplified by methylsulfonyloxy, ethylsulfonyloxy and the like, and $C_{6-10}$ arylsulfonyloxy group is exemplified by benzenesulfonyloxy, ortho-, meta-, or para-toluenesulfonyloxy, ortho-, meta-, or para-nitrobenzenesulfonyloxy group and the like.

Production Method 2

Using compound (V) as a starting material, the series of the following reactions are carried out to synthesize racemate compound (IIa), which is optically resolved to advantageously give the compound.

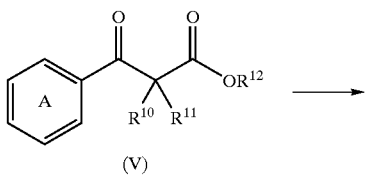

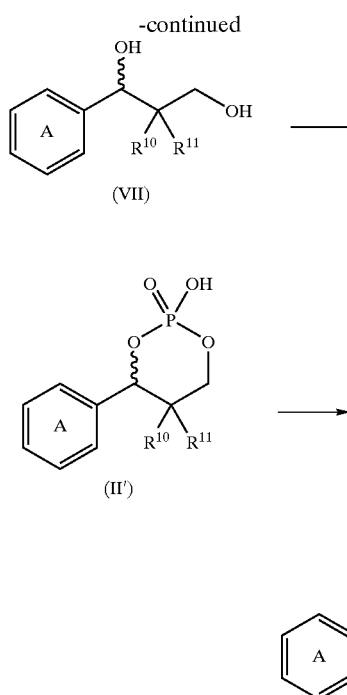

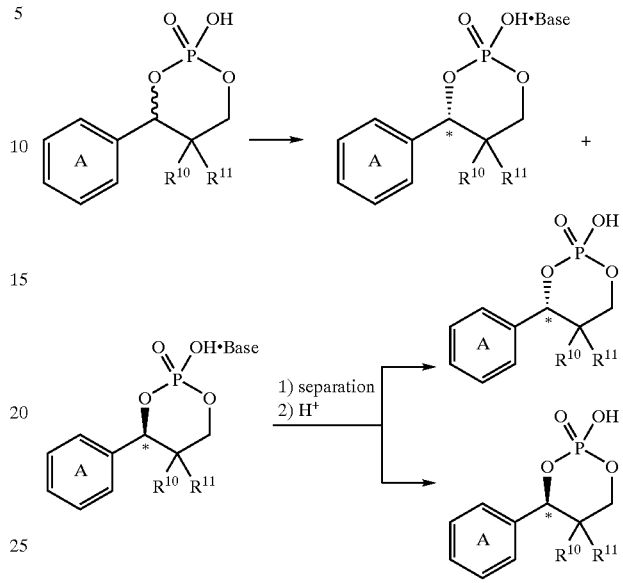

wherein each symbol is as defined above.

That is, compound (V) is reduced to give a diol compound, which is then subjected to phosphorylation to give racemate compound (II'), which is then subjected to optical resolution to give an optically active isomer.

The first step of this production method is performed according to a method known per se. The reducing agent is exemplified by metal hydrides such as sodium borohydride, lithium borohydride, lithium aluminum hydride, diisopropyl aluminum hydride, triethyl lithium borohydride and the like, and boranes such as diborane, catecholborane, 9-BBN and the like. The solvent is exemplified by aromatic hydrocarbons such as benzene, toluene, xylene and the like, ethers such as diethyl ether, diisopropyl ether, butylmethyl ether, dioxane, tetrahydrofuran and the like, and halogenated hydrocarbons such as chloroform, dichloromethane, ethylene dichloride, carbon tetrachloride and the like. Alcohols such as methanol, ethanol, propanol and the like may be used in some cases. Preferably, ethers such as diethyl ether, tetrahydrofuran and the like are used. These reducing agents are use in amount of 0.5–10 molar equivalents, preferably 0.5–2 molar equivalents, relative to compound (V). This reaction is generally carried out from −20° C. to 100° C., preferably from 0° C. to 100° C., for 0.5 hour to 100 hours, preferably from 0.1 hour to 24 hours. The diol compound thus obtained can be isolated by a separation and purification means known per se, such as concentration, solvent extraction, crystallization, phase transfer and chromatography. It is also possible to use the compound as a crude product as a starting material for the next step.

The phosphorylation step of compound (VII) can be carried out in the same manner as in phosphorylation of the aforementioned compound (VII).

The next step is optical resolution. The optical resolution of the obtained racemate cyclic phosphoric acid (dioxaphosphorinan) can be carried out by liquid chromatography using an optically active column, or by introducing into a diastereomer by the reaction with an optically active alcohol and separation by physical means, or by forming a diastereomer salt by reaction with an optically active amino compound and separation by physical means. Of these, a method for forming a diastereomer salt as shown in the following formulas is particularly preferable.

wherein each symbol is as defined above.

The optically active amino compound used to form a diastereomer salt cannot be specified because it varies depending on compound (IIa) and each compound. For example, it includes (−)-ephedrine, (+)-cinchonine, (−)-cinchonine, (+)-quinidine, (−)-quinidine, (+)-dehydroabiethylamine, (+)-2-amino-1-phenyl-1,3-propanediol, (−)-2-amino-1-phenyl-1,3-propanediol, (−)-(parahydroxyphenyl)glycine, (+)-phenylethylamine, (−)-phenylethylamine, (+)-tolylethylamine, (−)-tolylethylamine, (+)-(1-naphthyl)ethylamine, (+)-cyclohexylethylamine, (−)-cyclohexylethylamine, (+)-prolinol, and amino acid ester.

For mutual separation of diastereomer salts, crystallization and subsequent filtration are generally used, wherein each salt is obtained from crystals and mother liquor.

The salt obtained as crystals and the salt obtained by concentration of the mother liquor are each independently treated with acid to give an optically active compound (IIa). The acid to be used for this purpose includes, for example, hydrochloric acid, hydrobromic acid, sulfuric acid, phosphoric acid and the like, with preference given to hydrochloric acid. This reaction is preferably carried out in a solvent, more preferably in water.

To improve the chemical purity or optical purity of the obtained compound (IIa), recrystallization can be performed.

Production Method 3

Moreover, compound (IIa) can be advantageously produced according to, for example, the method described in Journal of Organic Chemistry, Vol. 50, p. 4508 (1985) and using aldehyde as a starting material by the following series of reactions to synthesize a racemate compound (IIa), which is then subjected to optical resolution.

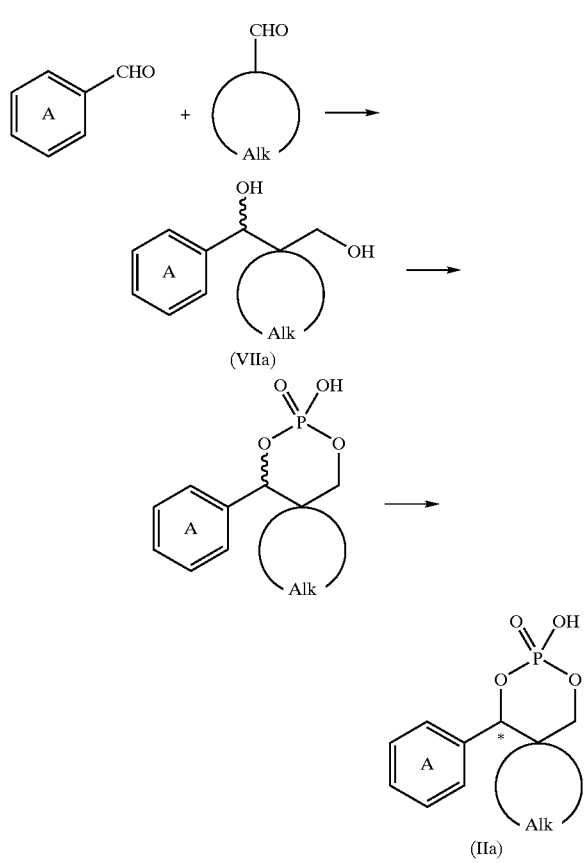

wherein each symbol is as defined above.

That is, by Aldol Canizzaro reaction of aromatic aldehyde and cycloalkylaldehyde to give a diol compound, which is then subjected to phosphorylation to give a racemate compound (IIa), followed by optical resolution thereof, an optically active isomer can be produced.

The first step in this Production method 3 is an Aldol Canizzaro reaction of aromatic aldehyde and cycloalkylaldehyde generally using 2 molar equivalents of cycloalkylaldehyde relative to aromatic aldehyde. This reaction is carried out as appropriate in a solvent in the presence of a base.

The base is exemplified by alkali metal alkoxides such as sodium methoxide, sodium ethoxide and the like, inorganic bases such as potassium carbonate, sodium carbonate and the like, alkali metal hydroxides such as sodium hydroxide, potassium hydroxide and the like, alkali metal hydrides such as sodium hydride, potassium hydride and the like, alkali metal carboxylates such as sodium acetate and the like, secondary amines such as piperidine, piperazine, pyrrolidine, morpholine, diethylamine and the like, and pyridines such as pyridine, dimethylaminopyridine and the like. Preferably, alkali metal hydroxides such as sodium hydroxide, potassium hydroxide and the like are used. The amount of these bases to be used is preferably 1 to 5 molar equivalents relative to aromatic aldehyde.

The solvent is exemplified by alcohols such as methanol, ethanol, propanol, butanol and the like, aromatic hydrocarbons such as benzene, toluene, xylene and the like, ethers such as diethyl ether, diisopropyl ether, butylmethyl ether, dioxane, tetrahydrofuran and the like, halogenated hydrocarbons such as chloroform, dichloromethane, ethylene dichloride, carbon tetrachloride and the like, N,N-dimethylformamide, dimethyl sulfoxide and the like. Preferably, alcohols such as methanol, ethanol and the like are used. The amount of the solvent to be used is 1 to 50-fold (v/w), preferably 1 to 10-fold (v/w), relative to aromatic aldehyde.

This reaction is generally carried out from 0° C. to 100° C., preferably from 0° C. to 100° C., for 0.5 hour to 50 hours, preferably for 0.5 hour to 24 hours.

The compound (VIIa) thus obtained can be isolated by a separation and purification means known per se, such as concentration, solvent extraction, crystallization, phase transfer, chromatography and the like. Alternatively, the compound can be used in the next step as a crude product.

The obtained diol compound can be converted to an optically active form (dioxaphosphorinan) or a compound represented by compound (IIa) according to the method described in the above-mentioned Production method 2.

An optically active form of compound (II) of the present invention resolves optically active isomers of various amino compounds, which are useful for the production of pharmaceutical agents, agricultural chemicals, liquid crystals and a starting material thereof and the like, and can be used as a reagent for optical resolution. For example, as described in Examples 2 and 8, the compound can be used as a reagent for optical resolution of 1-(6,7-dimethoxynaphthalen-2-yl)-1-(1H-imidazol-4-yl)-2-methyl-1-propanol, and 1-(1H-imidazol-4-yl-1-(6-methoxynaphthalen-2-yl)-2-methyl-1-propanol.

BEST MODE FOR EMBODIMENT OF THE INVENTION

The present invention is explained in detail in the following by referring to Reference Examples and Examples, which are not to be construed as limitative.

The nuclear magnetic resonance spectrum ($^1$H-NMR) was measured by JEOL. Ltd, JMTCO400/54 (400 MHz) or Hitachi, Ltd., R-90H (90 MHz) using tetramethylsilane as an internal standard. The δ values are shown in ppm. The symbols in Reference Examples mean the following.

s: singlet, d: doublet, t: triplet, m: multiplet, br: broad, J: coupling constant.

The infrared absorption spectrum (IR) was recorded using Paragon 1000 manufactured by Perkin-Elmer Corporation, according to KBr method.

enantiomer excess (% ee) and diastereomer excess (% de) were measured by high performance liquid chromatography.

high performance liquid chromatography (Condition A)
  column: SUMICHIRAL OA-3300 4.6×250 mm (SUMIKA CHEMICAL ANALYSIS SERVICE, LTD.)
  mobile phase: 0.05M ammonium acetate—ethanol solution
  flow rate: 0.3 ml/min
  detection: UV (254 nm)
  temperature: room temperature high performance liquid chromatography (Condition B)
  column: CHIRALPAK AD (DAICEL CHEMICAL INDUSTRIES, LTD.)
  mobile phase: hexane/ethanol 85:15
  flow rate: 1.0 ml/min.
  detection: UV 254 nm
  temperature: room temperature.

high performance liquid chromatography (Condition C)
  column: CHIRALCEL OD-RH (DAICEL CHEMICAL INDUSTRIES, LTD.)

mobile phase: 0.1 M aqueous potassium hexafluorophosphate
solution: acetonitrile 70:30
flow rate: 0.5 ml/min.
detection: UV 254 nm
temperature: room temperature.
high performance liquid chromatography (Condition D)
   column: CHIRALPAK AD (DAICEL CHEMICAL INDUSTRIES, LTD.)
   mobile phase: hexane/ethanol/diethylamine 85:15:0.1
   flow rate: 1.0 ml/min.
   detection: UV 254 nm
   temperature: room temperature.
high performance liquid chromatography (Condition E)
   column: SUMICHIRAL OA-4700, 2 columns (SUMIKA CHEMICAL ANALYSIS SERVICE, LTD.)
   mobile phase: 0.12 M ammonium acetate/methanol (4/1)
   flow rate: 0.5 ml/min
   detection: UV (240 nm).
   temperature: room temperature.
high performance liquid chromatography (Condition F)
   column: CHIRALCEL OD (DAICEL CHEMICAL INDUSTRIES, LTD.)
   mobile phase: hexane/2-propanol (95/5)
   flow rate: 0.5 ml/min
   detection: UV (220 nm)
   temperature: room temperature.

REFERENCE EXAMPLE 1

Production of 1-(1H-imidazol-4-yl)-1-(6-methoxynaphthalen-2-yl)-2-methylpropanol (i) Production of (6-methoxynaphthalen-2-yl)-(1-trityl-1H-imidazol-4-yl)methanol 2-Bromo-6-methoxynaphthalene (30 g) was dissolved in THF (400 ml) and cooled to −78° C. A solution (1.6 M; 99 ml) of n-butyl lithium in hexane was added dropwise, and the mixture was stirred at −78° C. for 30 min. A solution (300 ml) of 4-formyl-1-trityl-1H-imidazol (38.9 g) in THF was slowly added dropwise. After stirring at −78° C. for 30 min, the reaction mixture was poured into 3% aqueous citric acid solution (600 ml). The organic layer was separated and the aqueous layer was extracted with ethyl acetate. The organic layer was combined and the mixture was washed with saturated brine, dried and concentrated. The residue was washed with ethyl acetate to give the title compound (35.0 g) as a colorless solid.

$^1$H-NMR (CDCl$_3$) δ: 3.90 (3H, s), 5.89 (1H, s), 6.60 (1H, d, J=1.4 Hz), 7.08–7.15 (8H, m), 7.26–7.34 (9H, m), 7.42–7.47 (2H, m), 7.63–7.69 (2H, m), 7.78 (1H, s).

IR (KBr): 3166, 1603, 1478, 1451, 1260, 1171, 1128, 754, 702 cm$^{-1}$.

(ii) Production of (6-methoxynaphthalen-2-yl)-(1-trityl-1H-imidazol-4-yl)ketone (6-methoxynaphthalen-2-yl)-(1-trityl-1H-imidazol-4-yl)methanol (18.0 g) was dissolved in chloroform (300 ml) and manganese dioxide (56 g) was added. The mixture was heated under reflux for 1 h. The reaction mixture was filtrated and concentrated. To the residue was added ether and the mixture was crystallized to give the title compound (17.0 g) as a colorless solid.

$^1$H-NMR (CDCl$_3$) δ: 3.94 (3H, ), 7.15–7.23 (8H, m), 7.34–7.40 (9H, m), 7.58 (1H, d, J=1.3 Hz), 7.78 (1H, d, J=1.3 Hz), 7.78 (1H, d, J=8.6 Hz), 7.86 (1H, d, J=9.6 Hz), 8.26 (1H, dd, J=8.6, 1.6 Hz), 8.95 (1H, 9).

IR (KBr): 1620, 1520, 1493, 1480, 1445, 1265, 1196, 1179, 909, 872, 747, 733, 702 cm$^{-1}$.

(iii) Production of (1H-imidazol-4-yl)-(6-methoxynaphthalen-2-yl)ketone (6-Methoxynaphthalen-2-yl)-(1-trityl-1H-imidazol-4-yl)ketone (15.0 g) was dissolved in THF (80 ml) and 90% formic acid (20 ml) was added. The mixture was stirred at 50° C. for 2 h and the solvent was evaporated. 1N Hydrochloric acid (60 ml) was added and the precipitate was filtrated. The filtrate was washed with ether and neutralized with potassium carbonate. The resulting precipitate was collected by filtration and dried under reduced pressure to give the title compound (7.54 g) as a colorless solid.

$^1$H-NMR (CDCl$_3$+CD$_3$OD) δ: 3.97 (3H, s), 7.26–7.21 (2H, m), 7.78 (1H, s), 7.82–7.91 (3H, m), 7.99 (1H, dd, J=8.5, 1.7 Hz), 8.49 (1H, 5).

IR (KBr): 1636, 1624, 1481, 1346, 1264, 1169, 1024, 1005 cm$^{-1}$.

(iv) Production of 1-(1H-imidazol-4-yl)-1-(6-methoxynaphthalen-2-yl)-2-methylpropanol (1H-Imidazol-4-yl)-(6-methoxynaphthalen-2-yl)ketone (6.50 g) was dissolved in THF (120 ml) and the mixture was cooled to −10° C. A solution (2.0 M; 38.7 ml) of isopropyl magnesium chloride in THF was slowly added dropwise and the mixture was stirred for 30 min. To the reaction mixture was added saturated aqueous solution of ammonium chloride and the mixture was diluted with water and extracted with ethyl acetate. The extract was washed with saturated brine, and after drying, concentrated. The obtained residue was purified by silica gel column chromatography (eluate, chloroform:methanol=20:1→10:1) and recrystallized from ethyl acetate to give the title compound (5.04 g) as a colorless crystalline powder.

$^1$H-NMR (CDCl$_3$+CD$_3$OD) δ: 0.81 (3H, d, J=6.8 Hz), 1.00 (3H, d, J=6.8 Hz), 2.64–2.78 (1H, m), 3.91 (3H, s), 7.00 (1H, d, J=1.0 Hz), 7.09–7.15 (2H, m), 7.51–7.56 (2H, m), 7.65–7.75 (2H, m), 7.91 (1H, d, J=1.4 Hz).

IR (KBr): 3140, 2984, 2957, 1464, 1222, 1028, 856, 806, 652 cm$^{-1}$.

REFERENCE EXAMPLE 2

Production of 1-(1H-imidazol-4-yl)-1-(6-methoxynaphthalen-2-yl)butanol

By the reaction in the same manner as in Reference Example 1-(iv) using (1H-imidazol-4-yl)-6-methoxynaphthalen-2-ylketone (0.60 g) and a solution (1.0 mol, 2.4 ml) of n-propylmagnesium bromide in THF, the title compound (0.53 g) was obtained as a colorless solid.

$^1$H-NMR (CDCl$_3$) δ: 0.89 (3H, t, J=7.3 Hz), 1.10–1.30 (1H, m), 1.37–1.55 (1H, m), 2.20–2.30 (2H, m), 3.91 (3H, s), 6.90 (1H, s), 7.10–7.15 (2H, m), 7.45 (1H, dd, J=8.6, 1.8 Hz), 7.50 (1H, s), 7.65–7.73 (2H, m), 7.91 (1H, s).

IR (KBr): 2955, 1605, 1505, 1483, 1265, 1221, 1167, 1032, 850 cm$^{-1}$.

REFERENCE EXAMPLE 3

Production of 1-(6-ethoxynaphthalen-2-yl)-1-(1H-imidazol-4-yl)-2-methyl-1-propanol (i) Production of (6-ethoxynaphthalen-2-yl)(1-trityl-1H-imidazol-4-yl)ketone 2-Bromo-6-ethoxynaphthalene (5.3 g) was dissolved in THF (40 ml) and magnesium (0.515 g) and methyl iodide (one drop) were added and the mixture was vigorously stirred to dissolve magnesium. The reaction mixture was ice-cooled and a solution of 4-formyl-1-tritylimidazole (7 g)

in THF (80 ml) was added dropwise over 30 min. The mixture was stirred at room temperature for 1 h. To the reaction mixture were added saturated aqueous solution (40 ml) of ammonium chloride and water (40 ml) and the mixture was extracted with ethyl acetate. The extract was washed with saturated brine, dried over magnesium sulfate and concentrated. The residue was washed with ethyl acetate to give (6-ethoxynaphthalen-2-yl)-(1-trityl-1H-imidazol-4-yl)methanol (6.3 g) as a colorless powder. This product (6.3 g) was dissolved in dichloromethane (120 ml) and manganese dioxide (6 g) was added. The mixture was stirred at room temperature overnight. The reaction mixture was filtered through Celite and the filtrate was concentrated. The residue was crystallized from THF-ethyl acetate to give the title compound (5.5 g) as a colorless powder.

$^1$H-NMR (CDCl$_3$) d: 1.40 (3H, t, J=7 Hz), 4.08 (2H, q, J=7 Hz), 7.00–7.35 (17H, m), 7.47 (1H, d, J=1.4 Hz), 7.60–7.70 (3H, m), 8.15 (1H, d, J=8.8 Hz), 8.84 (1H, s).

IR (KBr): 1620, 1520, 1469, 1263, 1182 cm$^{-1}$.

(ii) Production of 1-(6-ethoxynaphthalen-2-yl)-1-(1-trityl-1H-imidazol-4-yl)-2-methyl-1-propanol (6-Ethoxynaphthalen-2-yl)-(1-trityl-1H-imidazol-4-yl) ketone (3.0 g) was dissolved in THF (45 ml) and a solution (2 M, 4 ml) of isopropyl magnesium chloride in THF was added dropwise under ice-cooling. The mixture was stirred at room temperature for 30 min and saturated aqueous solution (20 ml) of ammonium chloride and water (20 ml) were added. The mixture was extracted with ethyl acetate and the extract was washed with saturated brine, dried and concentrated. The residue was crystallized from ethyl acetate-diisopropyl ether to give the title compound (1.72 g) as a colorless powder. Crystallization mother liquor was purified by silica gel chromatography (eluate, hexane-ethyl acetate=1:2) to give the title compound (0.43 g).

$^1$H-NMR (CDCl$_3$) d: 0.75 (3H, d, J=6.8 Hz), 0.94 (3H, d, J=6.8 Hz), 1.47 (3H, t, J=7 Hz), 2.40–2.60 (1H, m), 3.64 (1H, s), 4.16 (2H, q, J=7 Hz), 6.80 (1H, s), 7.05–7.45 (18H, m), 7.50–7.75 (3H, m), 7.93 (1H, s).

IR (KBr): 2974, 1603, 1489, 1473, 1394 cm$^{-1}$.

(iii) Production of 1-(6-ethoxynaphthalen-2-yl)-1-(1H-imidazol-4-yl)-2-methyl-1-propanol 1-(6-Ethoxynaphthalen-2-yl)-1-(1-trityl-1H-imidazol-4-yl)-2-methyl-1-propanol (0.60 g) was dissolved in acetic acid (10 ml) and 10% palladium carbon (0.2 g) was added and the mixture was stirred at 50° C. for 2 h and at 60° C. for 3 h under a hydrogen atmosphere. The catalyst was filtered off and the filtrate was concentrated to dryness. Recrystallization from THF-ethyl acetate gave the title compound (0.21 g) as a colorless crystalline powder.

$^1$H-NMR (CDCl$_3$) d: 0.81 (3H, d, J=6.8 Hz), 1.00 (3H, d, J=6.8 Hz), 1.47 (3H, t, J=7 Hz), 2.60–2.80 (1H, m), 4.14 (2H, q, J=7 Hz), 6.99 (1H, s), 7.09–7.15 (2H, m), 7.49–7.55 (2H, m), 7.65 (1H, d, J=8.8 Hz), 7.71 (1h, d, J=8.8 Hz), 7.91 (1H, d, J=1.8 Hz).

IR (KBr): 2976, 1633, 1604, 1504, 1473, 1392, 1260, 1219 cm$^{-1}$.

REFERENCE EXAMPLE 4

Production of N-{6-[1-hydroxy-1-(1H-imidazol-4-yl)-2-methylpropyl]naphthalen-2-yl}acetamide (i) Production of N-{6-[1-hydroxy-2-methyl-1-(1-trityl-1H-imidazol-4-yl)propyl]naphthalen-2-yl}acetamide 1-{6-[(Diphenylmethylene)amino]naphthalen-2-yl}-2-methyl-1-(1-trityl-1H-imidazol-4-yl)-1-propanol (15.0 g) was dissolved in THF (5 ml)-methanol (5 ml) and sodium acetate (285 mg) and hydroxylamine hydrochloride (181 mg) were added. The mixture was stirred at room temperature for 20 min. 0.1N aqueous sodium hydroxide solution was added and the mixture was extracted with ethyl acetate, washed with saturated brine and dried to give a crude product of 1-(6-aminonaphthalen-2-yl)-2-methyl-1-(1-trityl-1H-imidazol-4-yl)-1-propanol as a pale-yellow oily substance. This product was dissolved in dichloromethane (100 ml), and pyridine (5.3 ml) and acetic anhydride (4.1 ml) were added. The mixture Was stirred at room temperature for 40 min. Saturated aqueous sodium hydrogen carbonate was added, and the mixture was extracted with dichloromethane and dried. The solvent was evaporated and the residue was recrystallized from ethyl acetate to give the title compound (11.6 g) as pale-red crystals.

$^1$H-NMR (CDCl$_3$+CD$_3$OD) δ: 0.75 (3H, d, J=6.7 Hz), 0.95 (3H, d, J=6.7 Hz), 2.20 (3H, s), 2.57–2.71 (1H, m), 6.87 (1H, d, J=1.4 Hz), 7.10–7.15 (6H, m), 7.32–7.54 (12H, m), 7.68–7.77 (2H, m), 7.92 (1H, s), 8.15 (1H, 9), 9.60 (1H, br s).

IR (KBr): 3058, 2969, 1686, 1611, 1547, 1493, 1445, 1298, 1011, 766, 747, 700 cm$^{-1}$.

(ii) Production of N-{6-[1-hydroxy-1-(1H-imidazol-4-yl)-2-methylpropyl]naphthalen-2-yl}acetamide N-{6-[1-Hydroxy-2-methyl-1-(1-trityl-1H-imidazol-4-yl)propyl]naphthalen-2-yl}acetamide (11.5 g) and pyridine hydrochloride (390 mg) were dissolved in methanol (8 ml) and the mixture was stirred at 60° C. for 2 h. After allowing to cool, the mixture was neutralized with saturated aqueous sodium hydrogen carbonate. The solvent was evaporated and the residue was collected by filtration and washed with ethanol. The filtrate was concentrated and the obtained residue was purified by silica gel column chromatography (eluate, dichloromethane:methanol =30:1→10:1) and recrystallized from ethyl acetate to give the title compound (5.52 g) as a pale-red powder.

$^1$H-NMR (CDCl$_3$+CD$_3$OD) δ: 0.79 (3H, d, J=6.8 Hz), 1.0 (3H, d, J=6.8 Hz), 2.17 (3H, s), 2.63–2.76 (1H, m), 6.99 (1H, s), 7.43–7.54 (3H, m), 7.65–7.74 (2H, m), 7.91 (1H, s), 8.11 (1H, s).

IR (KBr): 3248, 2971, 1669, 1609, 1586, 1557, 1495, 1391, 1296, 818 cm$^{-1}$.

REFERENCE EXAMPLE 5

Production of 1-(6,7-dimethoxynaphthalen-2-yl)-1-(1H-imidazol-4-yl)-2-methyl-1-propanol (i) Production of ethyl 2,3-dimethoxynaphthalene-6-carboxylate Lithium diisopropylamide THF solution (2 M; 65 ml) was diluted with THF (100 ml) and cooled to −78° C. A solution of ethyl 1,3-dioxan-3-propanoate (20.12 g) in THF (30 ml) was slowly added dropwise and the mixture was stirred at −78° C. for 1 h. A solution of 3,4-dimethoxybenzaldehyde (17.59 g) in THF (40 ml) was slowly added dropwise and the mixture was stirred at −78° C. for 1 h and warmed to room temperature. To the reaction mixture was added saturated aqueous solution of ammonium chloride and the mixture was extracted with ethyl acetate. The organic layer was washed with saturated brine, dried and concentrated. The residue was purified by silica gel column chromatography (eluate, hexane:ethyl acetate=2:1) to give ethyl 3-(3,4-dimethoxyphenyl)-2-(1,3-dioxan-2-ylmethyl)-3-hydroxypropionate (33.09 g) as an oil. This product was diluted with toluene (400 ml) and polyphosphoric acid (54 g) was added. The mixture was stirred at 100° C. for 15 min. After cooling, water was added to the reaction mixture and the mixture was extracted with ethyl acetate. The organic layer was washed with saturated aqueous sodium hydrogen carbonate and saturated brine and dried over anhydrous magnesium sulfate the solvent was evaporated and the residue was purified by silica gel column chromatography (eluate, hexane:ethyl acetate=4:1) and crystallized from ethyl acetate-hexane to give the title compound (16.01 g) as a colorless solid.

$^1$H-NMR (CDCl$_3$) δ: 1.44 (3H, t, J=7.2 Hz), 4.01 (3H, s), 4.02 (3H, s), 4.42 (2H, q, J=7.2 Hz), 7.14 (1H, s), 7.21 (1H, s), 7.70 (1H, d, J=8.5 Hz), 7.94 (1H, dd, J=8.5, 1.8 Hz), 8.45 (1H, m).

IR (KBr): 2978, 1713, 1489, 1238 cm$^{-1}$.

(ii) Production of (6,7-dimethoxynaphthalen-2-yl)methanol

Lithium aluminum hydride (2.77 g) was added to THF (200 ml) and the mixture was cooled to 0° C. Ethyl 2,3-dimethoxynaphthalene-6-carboxylate (14.30 g) was slowly added and the mixture was stirred at room temperature for 1 h. To the reaction mixture was added 1N hydrochloric acid and the mixture was extracted with ethyl acetate. The organic layer as dried and concentrated, and the residue was recrystallized from ethyl acetate-diisopropyl ether to give the title compound (9.73 g) as a colorless solid.

$^1$H-NMR (CDCl$_3$) δ: 3.99 (3H, s), 4.00 (3H, s), 4.80 (2H, s), 7.10 (1H, s), 7.11 (1H, s), 7.33 (1H, dd, J=8.4, 1.8 Hz), 7.60–7.72 (2H, m).

IR (KBr): 3299, 1514, 1497, 1262, 1161, 856 cm$^{-1}$.

(iii) Production of 6,7-dimethoxy-2-formyl naphthalene

By the reaction in the same manner as in Reference Example 1-(ii) using (6,7-dimethoxynaphthalen-2-yl) methanol (9.26 g), the title compound (7.40 g) was obtained as a colorless solid.

$^1$H-NMR (CDCl$_3$) δ: 4.04 (6H, s), 7.17 (1H, s), 7.26 (1H, s), 7.76 (1H, d, J=8.4 Hz), 7.83 (1H, dd, J=8.4, 1.6 Hz), 8.19 (1H, m), 10.10 (1H, s).

IR (KBr): 1688, 1487, 1211, 1157 cm$^{-1}$.

(iv) Production of (6,7-dimethoxynaphthalen-2-yl)(1H-imidazol-4-yl)ketone

4-Bromo-1H-imidazol (1.95 g) was dissolved in THF (30 ml) and the mixture was cooled to −78° C. A solution (1.7 M; 20 ml) of t-butyllithium in pentane was added. The mixture was stirred at 0° C. for 1.5 h and again cooled to −78° C. A solution (20 ml) of 6,7-dimethoxy-2-formyl naphthalene (3.32 g) in THF was added and the mixture was warmed from −78° C. to room temperature. The mixture was stirred at room temperature for 16 h and aqueous solution of ammonium chloride was added. The mixture was extracted with ethyl acetate and the organic layer was dried and concentrated. The residue was purified by silica gel column chromatography (eluate, dichloromethane:methanol=10:1) and crystallized from dichloromethane-methanol to give the title compound (1.31 g) as a colorless solid.

$^1$H-NMR (DMSO-d$_6$) δ: 3.93 (3H, s), 3.94 (3H, s), 7.39 (1H, s), 7.53 (1H, s), 7.80–8.03 (5H, m), 8.72 (1H, brs).

IR (KBr): 3088, 1636, 1508, 1489, 1260, 1159, 883 cm$^{-1}$.

(v) Production of 1-(6,7-dimethoxynaphthalen-2-yl)-1-(1H-imidazol-4-yl)-2-methyl-1-propanol By the reaction in the same manner as in Reference Example 1-(iv) using (6,7-dimethoxynaphthalen-2-yl)(1H-imidazol-4-yl)ketone (0.804 g), the title compound (0.613 g) was obtained as a colorless solid.

$^1$H-NMR (CDCl$_3$) δ: 0.81 (3H, d, J=6.6 Hz), 1.00 (3H, d, J=6.6 Hz), 2.60–2.78 (1H, m), 3.96 (3H, s), 3.97 (3H, s), 6.98 (1H, d, J=1.0 Hz), 7.07 (1H, s), 7.11 (1H, s), 7.41–7.49 (2H, m), 7.61 (1H, d, J=8.4 Hz), 7.89 (1H, d, J=1.4 Hz).

IR (KBr): 3322, 2965, 1510, 1254, 1163, 731 cm$^{-1}$.

EXAMPLE 1

Production of salt of (−)-1-(6,7-dimethoxynaphthalen-2-yl)-1-(1H-imidazol-4-yl)-2-methyl-1-propanol and (−)-8-hydroxy-7,9-dioxa-6-phenyl-8-phosphaspiro[4.5]decan-8-one A racemate (200 mg) of 1-(6,7-dimethoxynaphthalen-2-yl)-(1-H-imidazol-4-yl)-2-methyl-1-propanol and (−)-8-hydroxy-7,9-dioxa-6-phenyl-8-phosphaspiro[4.5]decan-8-one (164.4 mg) were dissolved in ethanol (4.0 ml) by heating. The mixture was stood still at room temperature overnight, and the precipitate was collected by filtration to give 153.7 mg of white crystals. As a result of the HPLC analysis (Condition B), the diastereomer excess was found to be 92% de.

To this salt (151 mg) was added ethanol (1.5 ml) and the mixture was stood as it was for 3 days. Crystals were collected by filtration to give 130.5 mg of white crystals (yield 72.2%). As a result of the HPLC analysis (Condition B), the diastereomer excess was found to be 99% de.

EXAMPLE 2

Production of (−)-1-(6,7-dimethoxynaphthalen-2-yl)-1-(1H-imidazol-4-yl)-2-methyl-1-propanol A racemate (1.0 g) of 1-(6,7-dimethoxynaphthalen-2-yl)-1-(1H-imidazol-4-yl)-2-methyl-1-propanol and (−)-8-hydroxy-7,9-dioxa-6-phenyl-8-phosphaspiro[4.5]decan-8-one (822 mg) were dissolved in ethanol (21 ml) by heating and the mixture was stirred at room temperature for 6 h. The precipitate was collected by filtration to give 670 mg of white crystals (yield 74%). As a result of the HPLC analysis (Condition B), the diastereomer excess was found to be 99% de.

This salt (665 mg) was added to 25% aqueous ammonia (150 mg), water 20 ml and ethyl acetate (20 ml) and the mixture was stirred at room temperature for 30 min, followed by partitioning. The organic layer was concentrated under reduced pressure to give 368 mg of a dry solid (yield 74%). As a result of the HPLC analysis (Condition B), the enantiomer excess was found to be 99% ee.

EXAMPLE 3

Production of salt of (−)-1-(6,7-dimethoxynaphthalen-2-yl)-1-(1H-imidazol-4-yl)-2-methyl-1-propanol and (R)-(−)-1,1'-binaphthyl-2,2'-diyl hydrogen phosphate A racemate (50 mg) of 1-(6,7-dimethoxynaphthalen-2-yl)-1-(1H-imidazol-4-yl)-2-methyl-1-propanol and (R)-(−)-1,1'-binaphthyl-2,2'-diyl hydrogen phosphate (53.4 mg) were dissolved in ethanol 0.9 ml and the mixture was concentrated to dryness. To the dry solid were added acetonitrile (0.3 ml) and water (0.3 ml) to allow crystallization. Thereto was further added tetrahydrofuran (0.3 ml) and dissolved by heating. The mixture was stirred under room temperature for 1 h and the precipitate was collected by filtration to give 24.5 mg of crystals (yield 47%). As a result of the HPLC analysis (Condition B), the diastereomer excess was found to be 75% de.

EXAMPLE 4

Production of salt of (−)-1-(6,7-dimethoxynaphthalen-2-yl)-1-(1H-imidazol-4-yl)-2-methyl-1-propanol and (−)-2-hydroxy-5,5-dimethyl-4-phenyl-1,3,2-dioxaphosphorinan-2-one A racemate (200 mg) of 1-(6,7-dimethoxynaphthalen-2-yl)-1-(1H-imidazol-4-yl)-2-methyl-1-propanol and (−)-2-hydroxy-5,5-dimethyl-4-phenyl-1,3,2-dioxaphosphorinan-2-one (148 mg) were dissolved in ethanol (5 ml) and the mixture was stood overnight at room temperature. The precipitate was collected by filtration to give 117.6 mg of white crystals (yield 68%). Therefrom 117 mg was suspended in isopropanol (1 ml) and ethanol (2 ml) and the mixture was stirred under room temperature for 3 h. The crystals were collected by filtration to give 93.0 mg of white crystals (yield 54%). As a result of the HPLC analysis (Condition B), the diastereomer excess was found to be 97% de.

EXAMPLE 5

Production of salt of (−)-1-(1H-imidazol-4-yl)-1-(6-methoxy-2-naphthyl)-1-butanol and (−)-4-(2-chlorophenyl)-2-hydroxy-5,5-dimethyl-1,3,2-dioxaphosphorinan-2-one A racemate (40 mg) of 1-(1H-imidazol-4-yl)-1-(6-methoxy-2-naphthyl)-1-butanol and (−)-4-(2-chlorophenyl)-2-hydroxy-5,5-dimethyl-1,3,2-dioxaphosphorinan-2-one (37.3 mg) were dissolved in ethanol (0.3 ml) and tetrahydrofuran (0.2 ml) and the mixture was preserved in a refrigerator overnight. The next day, the precipitate was collected by filtration to give 4.1 mg of crystals (yield 11%). As a result of the HPLC analysis (Condition B), the diastereomer excess was found to be 76% de.

EXAMPLE 6

Production of salt of (−)-1-(6-ethoxy-2-naphthyl)-1-(1H-imidazol-4-yl)-2-methyl-1-propanol and (−)-4-(2,4-dichlorophenyl)-2-hydroxy-5,5-dimethyl-1,3,2-dioxaphosphorinan-2-one A racemate (40 mg) of 1-(6-ethoxy-2-naphthyl)-1-(1H-imidazol-4-yl)-2-methyl-1-propanol and (−)-4-(2,4-dichlorophenyl)-2-hydroxy-5,5-dimethyl-1,3,2-dioxaphosphorinan-2-one (40.1 mg) were dissolved in ethanol (0.4 ml) and methanol (0.4 ml) was added. The mixture was stood at room temperature for six days. Thereto were added ethanol (0.4 ml) and isopropanol (0.4 ml), and after stirring, the precipitate was collected by filtration to give 26.3 mg of crystals (yield 66%). As a result of the HPLC analysis (Condition B), the diastereomer excess was found to be 79% de.

EXAMPLE 7

Production of salt of (+)-N-{6-[1-hydroxy-1-(1H-imidazol-4-yl)-2-methylpropyl]naphthalen-2-yl}acetamide and (+)-2-hydroxy-4-(2-methoxyphenyl)-5,5-dimethyl-1,3,2-dioxaphosphorinan-2-one A racemate (50 mg) of N-{6-[1-hydroxy-1-(1H-imidazol-4-yl)-2-methylpropyl]naphthalen-2-yl}acetamide and (+)-2-hydroxy-4-(2-methoxyphenyl)-5,5-dimethyl-1,3,2-dioxaphosphorinan-2-one (42 mg) were dissolved in ethanol (0.9 ml) with heating, and seed crystal (>99% de) was added. The mixture was stood in a refrigerator overnight. The precipitate was collected by filtration to give 21.7 mg of crystals (yield 47%). As a result of the HPLC analysis (Condition B), the diastereomer excess was found to be 99% de.

EXAMPLE 8

Production of (−)-1-(1H-imidazol-4-yl)-1-(6-methoxynaphthalen-2-yl)-2-methyl-1-propanol A racemate (24 g) of 1-(1H-imidazol-4-yl-1-(6-methoxynaphthalen-2-yl)-2-methyl-1-propanol was dissolved in tetrahydrofuran (60 ml) and ethanol (630 ml) by heating. To this solution were added (−)-4-(2,4-dichlorophenyl)-2-hydroxy-5,5-dimethyl-1,3,2-dioxaphosphorinan-2-one (25.2 g) and ethanol (20 ml). The seed crystal (>99% de) was added, and the mixture was stirred at room temperature overnight. The precipitate was collected by filtration and dried to give 23.5 g of crystals. As a result of the HPLC analysis (Condition B), the diastereomer excess was found to be B9% de.

The above-mentioned salt was suspended in ethanol (400 ml), tetrahydrofuran (40 ml) and methanol (10 ml) and the mixture was stirred for overnight. The crystals obtained by filtration and drying was 20.4 g (yield 86%). As a result of the HPLC analysis (Condition B), the diastereomer excess was found to be 98% de.

The crystals (20.4 g) were suspended in ethanol (300 ml) and tetrahydrofuran (30 ml) and the mixture was stirred at room temperature overnight. Filtration and drying gave 18.6 g of crystals (yield 91%). As a result of the HPLC analysis (Condition B), the diastereomer excess was found to be 99% de.

The purified salt was stirred in water (about 300 ml) and 1N aqueous sodium hydroxide solution (32 ml) for 5 h. After decomposition, the precipitate was collected and washed with warm water. The obtained crystals were 8.6 g (yield 96%). As a result of the HPLC analysis (Condition B), the enantiomer excess was found to be 98% ee.

Melting point: 179–181° C.

EXAMPLE 9

Production of salt of (−)-1-(1H-imidazol-4-yl)-1-(6-methoxynaphthalen-2-yl)-2-methyl-1-propanol and (−)-4-(2-chlorophenyl)-2-hydroxy-5,5-dimethyl-1,3, 2-dioxaphosphorinan-2-one A racemate (200 mg) of 1-(1H-imidazol-4-yl-1-(6-methoxynaphthalen-2-yl)-2-methyl-1-propanol was suspended in tetrahydrofuran (0.5 ml) and ethanol (3.5 ml) and dissolved by heating. (−)-4-(2-Chlorophenyl)-2-hydroxy-5, 5-dimethyl-1,3,2-dioxaphosphorinan-2-one (188 mg) and ethanol (1.5 ml) were added, and the mixture was stood at room temperature overnight. The crystals were collected by filtration and dried to give 181.9 mg (yield 94%). As a result of the HPLC analysis (Condition B), the diastereomer excess was found to be 91% de.

EXAMPLE 10

Production of salt of (−)-1-(1H-imidazol-4-yl)-1-(6-methoxynaphthalen-2-yl)-2-methyl-1-propanol and (−)-4-(4-chlorophenyl)-2-hydroxy-5,5-dimethyl-1,3, 2-dioxaphosphorinan-2-one A racemate (200 mg) of 1-(1H-imidazol-4-yl)-1-(6-methoxynaphthalen-2-yl)-2-methyl-1-propanol was dissolved in acetonitrile (0.5 ml) and ethanol (2.5 ml) by heating and (−)-4-(4-chlorophenyl)-2-hydroxy-5,5-dimethyl-1,3,2-dioxaphosphorinan-2-one (188 mg) and ethanol (0.5 ml) were added. The mixture was stood at room temperature for 2 days. The precipitate was collected by filtration and dried to give the crystals (107.4 mg, yield 55%). As a result of the HPLC analysis (Condition B), the diastereomer excess was found to be 82% de.

EXAMPLE 11

Production of salt of (−)-1-(1H-imidazol-4-yl)-1-(6-methoxynaphthalen-2-yl)-2-methyl-1-propanol and (−)-2-hydroxy-4-(2-methoxyphenyl)-5,5-dimethyl-1, 3,2-dioxaphosphorinan-2-one A racemate (200 mg) of 1-(1H-imidazol-4-yl-1-(6-methoxynaphthalen-2-yl)-2-methyl-1-propanol was suspended in acetonitrile (0.5 ml) and ethanol (2.5 ml), and dissolved with heating. (−)-2-Hydroxy-4-(2-methoxyphenyl)-5,5-dimethyl-1,3,2-dioxaphosphorinan-2-one (181 mg) and ethanol (1.0 ml) were added and the mixture was stood at room temperature overnight. Because no crystallization was observed, acetonitrile (0.3 ml) was further added, and the mixture was stood in a refrigerator overnight. The precipitate was collected by filtration and dried to give crystals (124.1 mg, yield 65%). As a result of the HPLC analysis (Condition B), the diastereomer excess was found to be 81% de.

EXAMPLE 12

Production of salt of methyl 6-[1-hydroxy-1-(1H-imidazol-4-yl)-3-methylbutyl]-2-naphthate and (R)-(+)-4-(2-chlorophenyl)-5,5-dimethyl-1,3,2-dioxaphosphorinan-2-ol 2-oxide A racemate (250 mg) of methyl 6-[1-hydroxy-1-(1H-imidazol-4-yl)-3-methylbutyl]-2-naphthate and (R)-(+)-4-(2-chlorophenyl)-5,5-dimethyl-1,3,2-dioxaphosphorinan-2-ol 2-oxide (204.5 mg) were dissolved in ethanol (2.5 ml) with heating. The solution was stood overnight at room temperature, and the precipitate was collected by filtration to give 170.0 mg of white crystals. As a result of the HPLC analysis (Condition D), the diastereomer excess was found to be 74% de.

To this salt (169 mg) was added ethanol (2.8 ml), and the mixture was stirred overnight at room temperature. The crystals were collected by filtration to give 110.4 mg of white crystals. As a result of the HPLC analysis (Condition D), the diastereomer excess was found to be 95% de.

To this salt (109 mg) was added ethanol (1.5 ml), and the mixture was stood at room temperature for 3 days. The crystals were collected by filtration to give 87 mg of white crystals (yield 39%). As a result of the HPLC analysis (Condition D), the diastereomer excess was found to be 99% de.

EXAMPLE 13

Production of salt of methyl 6-[1-hydroxy-1-(1H-imidazol-4-yl)-3-methylbutyl]-2-naphthate and (R)-(+)-4-(2,4-dichlorophenyl)-5,5-dimethyl-1,3,2-dioxaphosphorinan-2-ol 2-oxide A racemate (50 mg) of methyl 6-[1-hydroxy-1-(1H-imidazol-4-yl)-3-methylbutyl]-2-naphthate and (R)-(+)-4-(2,4-dichlorophenyl)-5,5-dimethyl-1,3,2-dioxaphosphorinan-2-ol 2-oxide (45.6 mg) were dissolved in ethanol (0.5 ml) with heating. The solution was stood still overnight at room temperature, and precipitate was collected by filtration to give 40.4 mg of white crystals (yield 85%). As a result of the HPLC analysis (Condition D), the diastereomer excess was found to be 60% de.

EXAMPLE 14

Production of salt of methyl 6-[1-hydroxy-1-(1H-imidazol-4-yl)-2-methylpropyl]-2-naphthate and (S)-(−)-4-(2-chlorophenyl)-5,5-dimethyl-1,3,2-dioxaphosphorinan-2-ol 2-oxide A racemate (67 mg) of methyl 6-[1-hydroxy-1-(1H-imidazol-4-yl)-2-methylpropyl]-2-naphthate and (S)-(−)-4-(2-chlorophenyl)-5,5-dimethyl-1,3,2-dioxaphosphorinan-2-ol 2-oxide (57.2 mg) were dissolved in ethanol (0.9 ml). The mixture was stood still overnight at room temperature and the precipitate was collected by filtration to give 46.1 mg of white crystals. As a result of the HPLC analysis (Condition C), the diastereomer excess was found to be 71% de.

Ethanol (1.3 ml) was added to this salt (43.6 mg), and after refluxing for 30 min, the mixture was stirred at room temperature overnight. The crystals were collected by filtration to give 22.5 mg of white crystals (yield 39%). As a result of the HPLC analysis (Condition C), the diastereomer excess was found to be 98% de.

EXAMPLE 15

Production of salt of 6-[1-hydroxy-1-(1H-imidazol-4-yl)-3-methylbutyl]-N-methyl-2-naphthamide and (R)-(+)-4-(2-chlorophenyl)-5,5-dimethyl-1,3,2-dioxaphosphorinan-2-ol 2-oxide A racemate (50 mg) of 6-[1-hydroxy-1-(1H-imidazol-4-yl)-3-methylbutyl]-N-methyl-2-naphthamide and (R)-(+)-4-(2-chlorophenyl)-5,5-dimethyl-1,3,2-dioxaphosphorinan-2-ol 2-oxide (41.0 mg) were dissolved in acetonitrile (0.3 ml) and ethanol (0.3 ml). The mixture was stood still overnight at room temperature and the precipitate was collected by filtration to give 34 mg of white crystals. As a result of the HPLC analysis (Condition D), the diastereomer excess was found to be 81% de. 1-Propanol (1.0 ml) was added to this salt (31 mg) and dissolved by heating. The solution was stood at room temperature overnight. The crystals were collected by filtration to give 15.6 mg of white crystals (yield 38%). As a result of the HPLC analysis (Condition D), the diastereomer excess was found to be 99% de.

EXAMPLE 16

Production of salt of 6-[1-hydroxy-1-(1H-imidazol-4-yl)-3-methylbutyl]-N-methyl-2- and (S)-(−)-4-(2,4-dichlorophenyl)-5,5-dimethyl-1,3,2-dioxaphosphorinan-2-ol 2-oxide A racemate (50 mg) of 6-[1-hydroxy-1-(1H-imidazol-4-yl)-3-methylbutyl]-N-methyl-2-naphthamide and (S)-(−)-4-(2,4-dichlorophenyl)-5,5-dimethyl-1,3,2-dioxaphosphorinan-2-ol 2-oxide (46.1 mg) were dissolved in acetonitrile (0.3 ml) and ethanol (0.3 ml). The mixture was stood still overnight at room temperature and the precipitate was collected by filtration to give 36.6 mg of white crystals (yield 76%). As a result of the HPLC analysis (Condition D), the diastereomer excess was found to be 70% de.

EXAMPLE 17

Production of salt of 6-[1-hydroxy-1-(1H-imidazol-4-yl)propyl]-N-methyl-2-naphthamide and (R)-(+)-4-(2-chlorophenyl)-5,5-dimethyl-1,3,2-dioxaphosphorinan-2-ol 2-oxide A racemate (50 mg) of 6-[1-hydroxy-1-(1H-imidazol-4-yl)propyl]-N-methyl-2-naphthamide and (R)-(+)-4-(2-chlorophenyl)-5,5-dimethyl-1,3,2-dioxaphosphorinan-2-ol 2-oxide (44.7 mg) were dissolved in dimethoxyethane (0.5 ml) and isopropyl alcohol (0.1 ml). The mixture was stood still overnight at room temperature and the precipitate was collected by filtration to give 45.7 mg of white crystals. As a result of the HPLC analysis (Condition D), the diastereomer excess was found to be 58% de.

Tetrahydrofuran (1.6 ml) and isopropanol (0.2 ml) were added to this salt (42 mg) and the mixture was stood overnight at room temperature. The crystals were collected by filtration to give 28.8 mg of white crystals (yield 67%). As a result of the HPLC analysis (Condition D), the diastereomer excess was found to be 79% de.

EXAMPLE 18

Production of salt of 6-[1-hydroxy-1-(1H-imidazol-4-yl)-propyl]-N-methyl-2-naphthamide and (R)-(+)-4-(2-chlorophenyl)-5,5-dimethyl-1,3,2-dioxaphosphorinan-2-ol 2-oxide A racemate (50 mg) of 6-[1-hydroxy-1-(1H-imidazol-4-yl)-propyl]-N-methyl-2-naphthamide and (R)-(+)-4-(2-chlorophenyl)-5,5-dimethyl-1,3,2-dioxaphosphorinan-2-ol 2-oxide (44.7 mg) were dissolved in dimethoxyethane (0.8 ml) and isopropyl alcohol (0.15 ml). The mixture was stirred at room temperature overnight, and the precipitate was collected by filtration to give 75.5 mg of white crystals. As a result of the HPLC analysis (Condition D), the diastereomer excess was found to be 10% de.

Tetrahydrofuran (1.0 ml) and isopropanol (1.0 ml) were added to this salt (74 mg) and the mixture was stirred under room temperature for 6 h. The crystals were collected by filtration to give 27.5 mg of white crystals. As a result of the HPLC analysis (Condition D), the diastereomer excess was found to be 70% de.

Tetrahydrofuran (1.0 ml) and isopropanol (0.5 ml) were added to this salt (26.5 mg) and the mixture was stirred under room temperature overnight. The crystals were collected by filtration to give 12.8 mg of white crystals (yield 28%). As a result of the HPLC analysis (Condition D), the diastereomer excess was found to be 99% de.

mp; 185–186° C.

EXAMPLE 19

Production of salt of 6-[1-hydroxy-1-(1H-imidazol-4-yl)propyl]-N-methyl-2-naphthamide and (R)-(+)-4-(2,4-dichlorophenyl)-5,5-dimethyl-1,3,2-dioxaphosphorinan-2-ol 2-oxide A racemate (50 mg) of 6-[1-hydroxy-1-(1H-imidazol-4-yl)propyl]-N-methyl-2-naphthamide and (R)-(+)-4-(2,4-dichlorophenyl)-5,5-dimethyl-1,3,2-dioxaphosphorinan-2-ol 2-oxide (50.3 mg) were dissolved in dimethoxyethane (0.5 ml) and methanol (0.1 ml). The mixture was stood still overnight at room temperature and the precipitate was collected by filtration to give 23.7 mg of white crystals (yield 47%). As a result of the HPLC analysis (Condition D), the diastereomer excess was found to be 69% de.

EXAMPLE 20

Production of salt of 6-[1-hydroxy-1-(1H-imidazol-4-yl)propyl]-N-methyl-2-naphthamide and (R)-(+)-4-(2-methoxyphenyl)-5,5-dimethyl-1,3,2-dioxaphosphorinan-2-ol 2-oxide A racemate (50 mg) of 6-[1-hydroxy-1-(1H-imidazol-4-yl)propyl]-N-methyl-2-naphthamide and (R)-(+)-4-(2-methoxyphenyl)-5,5-dimethyl-1,3,2-dioxaphosphorinan-2-ol 2-oxide (44.0 mg) were dissolved in dimethoxyethane (0.5 ml) and methanol (0.1 ml). The mixture was stood still overnight at room temperature and the precipitate was collected by filtration to give 32.1 mg of white crystals (yield 68%). As a result of the HPLC analysis (Condition D), the diastereomer excess was found to be 56% de.

EXAMPLE 21

(1) Production of ethyl 1-benzoylcyclopentanecarboxylate

Diiodobutane (17.1 g, 55 mmol), sodium carbonate (35 g, 330 mmol), ethylbenzoylacetate (10.6 g, 55 mmol) and dimethylformamide (170 ml) were mixed and the mixture was stirred at 55 to 60° C. overnight. The mixture after completion of reaction was poured into ice water and the mixture was extracted twice with ethyl acetate (100 ml). The extract was dried over sodium sulfate, and after concentration, purified by silica gel column chromatography (hexane:ethyl acetate=9:1) to give the title compound (7.9 g, 58%) as a colorless oil.

$^1$H-NMR (400 MHz, CDCl$_3$) δ: 0.97 (3H, t, J=7.1 Hz), 1.66–1.78 (4H, m), 2.28–2.40 (4H, m), 4.05 (2H, q, J=7.1 Hz), 7.86 (2H, d, J=7.3 Hz), 7.39–7.51 (3H, m).

IR (neat) ν cm$^{-1}$: 2959, 1734, 1685.

(2) Production of ethyl 1-(1-hydroxyphenylmethyl)cyclopentanecarboxylate (S)-tBuBisP*-RuBr$_2$ (5 mg) was placed in a reactor, and after deaeration and substitution with argon, a mixture of ethyl 1-benzoylcyclopentanecarboxylate (246 mg, 1 mmol) and methanol (deaeration, 5 ml) was added. Under room temperature and hydrogen pressure (6 kg/cm$^2$), the mixture was stirred overnight and the mixture after completion of reaction was concentrated to dryness. This was concentrated and purified by silica gel column chromatography (hexane:ethyl acetate=3:1) to give a colorless oil (150 mg, 61%). The enantiomer excess was measured by high performance liquid chromatography (Condition (B)) and found to be 95.0% ee.

$^1$H-NMR (400 MHz, CDCl$_3$) δ: 1.20 (3H, t, J=7.1 Hz), 1.56–2.17 (8H, m), 3.49 (1H, d, J=6.3 Hz), 4.11–4.14 (2H, m), 4.80 (1H, d, J=6.3 Hz), 7.25–7.30 (5H, m).

IR (NaCl) ν cm$^{-1}$: 3496, 2957, 1717.

(3) Production of 1-(1-hydroxy-1-phenylmethyl)-1-hydroxymethylcyclopentane

Lithium aluminum hydride (1.05 g, 27.6 mmol) was suspended in ether (80 ml) and the mixture was cooled to –20° C. to –30° C. Thereto was added dropwise a solution of ethyl 1-(1-hydroxyphenylmethyl)cyclopentanecarboxylate (14.118.4 mmol) in ether (10 ml) while maintaining the solution at not higher than –20° C. The mixture was stirred at –20° C. for 1 h and at room temperature for 3 h, cooled to –20° C. and 10% NaHSO$_4$ aqueous solution (40 ml) was added dropwise. The mixture was stirred at 0° C. for 30 min and an insoluble material was removed by decantation. This was washed twice with ether (100 ml), and the organic layer was combined, washed with water and dried over anhydrous sodium sulfate. This was concentrated to dryness to give a colorless oil (3.12 g).

$^1$H-NMR (400 MHz, CDCl$_3$) δ: 1.49–1.80 (8H, m), 2.97 (1H, brs), 3.20 (1H, brs), 3.37 (1H, dd, J=1.8 and 10.9 Hz), 3.63 (1H, d, J=10.9 Hz), 4.71 (1H, s), 7.26–7.40 (5H, m).

(4) Production of 8-chloro-7,9-dioxa-6-phenyl-8-phosphospiro[4.5]decan-8-one 1-(1-Hydroxyphenylmethyl)-1-hydroxymethylcyclopentane (3.0 g, 14.5 mmol) was diluted with dichloromethane (16 ml), and under refluxing, a solution of phosphorus oxychloride (2.38 g, 15.5 mmol) in dichloromethane (12 ml) was added dropwise over 30 min. After the dropwise addition, the mixture was refluxed for 5 h. The mixture after completion of the reaction was concentrated. Ether (dry, 5 ml) was added, and the mixture was stirred under ice-cooling for 30 min. This was filtrated to give white crystals (3.0 g). The mother liquor was concentrated to dryness, and ether (5 ml) was added. The mixture was stirred under ice-cooling for 30 min. This was filtrated to give second crystals (0.28 g), total yield 79%.

(5) Production of 8-hydroxy-7,9-dioxa-6-phenyl-8-phosphospiro[4.5]decan-8-one Sodium hydroxide (0.67 g) was dissolved in water (8 ml) and the solution was heated to 95 to 100° C., and 8-chloro-7,9-dioxa-6-phenyl-8-phosphospiro[4.5]decan-8-one (3.2 g, 11.2 mmol) was added as a powder over 30 min, and the mixture was stirred at the same temperature for 20 min. The reaction mixture was allowed to cool to 60° C. and concentrated hydrochloric acid (3 ml) was added. The mixture was cooled to 13° C. to 15° C. Precipitated white crystals were collected by filtration, washed successively with water (2 ml) and ether (2 ml) and vacuum dried to give white crystals (2.6 g, 87%). The enantiomer excess of this product was measured by high performance liquid chromatography and found to be 91% ee.

This was dissolved in ethanol with heating and recrystallized to give white crystals (1.5 g, yield 58%). The enantiomer excess of this product was measured by high performance liquid chromatography (Condition (A)) and found to be not less than 99% ee.

$^1$H-NMR (400 MHz, CDCl$_3$) δ: 0.76–1.74 (8H, m), 3.93 (1H, dd, J=1.11 and 24.4 Hz), 4.20 (1H, d, J=11.1 Hz), 5.43 (1H, s), 7.33–7.41 (5H, m).

IR (KBr) ν cm$^{-1}$: 2292, 1734, 1205.

$[α]^{24}_D$=−60.8° (c=1.0, methanol).

EXAMPLE 22

(1) Production of ethyl 1-(1-hydroxy-1-phenylmethyl)cyclopentanecarboxylate To N,N-dimethylformamide (400 ml) were added ethyl benzoylacetate (25.1 g, 0.13 mol), 1,4-diiodobutane (40.47 g) (0.13 g) and anhydrous sodium carbonate (82.7 g, 0.78 mol) and the mixture was stirred at 60° C. for 15.5 h. The reaction mixture was poured into 1 L of water and the mixture was extracted with ethyl acetate. The extract was washed with saturated brine, dehydrated over anhydrous sodium sulfate and concentrated. A red residual solution (33.5 g) was purified by silica gel column chromatography (ethyl acetate/hexane=1/4) to give the title compound (24.67 g) as a colorless oil (yield 77%).

$^1$H-NMR (90 MHz, CDCl$_3$) δ: 0.97 (3H, t, J=7.0 Hz), 1.64–1.79 (4H, m), 2.26–2.44 (4H, m), 4.05 (2H, q, J=7.0 Hz), 7.29–7.52 (3H, m), 7.80–7.91 (2H, m).

(2) Production of 1-(hydroxyphenylmethyl)-1-hydroxymethylcyclopentane

Under a nitrogen stream, lithium aluminum hydride (0.38 g, 0.01 mol) was suspended in dehydrating ether (8 ml) and ethyl 1-(1-hydroxy-1-phenylmethyl)cyclopentanecarboxylate (2.46 g, 0.01 mol) as 8 ml of a dehydrating ether solution was added dropwise over 30 min while stirring the mixture at room temperature. After the completion of dropwise addition, the mixture was stirred for 30 min while gently refluxing, then 10% aqueous sodium hydrogen carbonate (1 ml) was slowly added dropwise under ice-cooling. Then 20% aqueous sodium hydroxide (2 ml) was added dropwise and the ether layer was taken by decantation. The residue was washed twice with ether (10 ml). The ether layer was combined and the mixture was dehydrated over anhydrous magnesium sulfate and concentrated. The residual solution (2.01 g) was purified by silica gel column chromatography (ethyl acetate/hexane=2/3) to give the title compound (1.8 g) as a colorless oil (yield 87%).

$^1$H-NMR (400 MHz, CDCl$_3$) δ: 1.06–1.11 (1H, m), 1.50–1.63 (5H, m), 1.70–1.81 (2H, m), 2.95 (1H, t), 3.16 (1H, d), 3.38 (1H, dd, J=5.3 Hz, 11.0 Hz), 3.64 (1H, dd, J=3.4 and 11.0 Hz), 4.71 (1H, d, J=3.4 Hz), 7.26–7.40 (5H, m).

(3) Production of 8-chloro-7,9-dioxa-6-phenyl-8-phosphaspiro[4.5]decan-8-one 1-(Hydroxyphenylmethyl)-1-hydroxymethylcyclopentane (23.3 g, 0.113 mol) was dissolved in dichloromethane (90 ml), and the mixture was heated under reflux with stirring. Phosphorus oxychloride (18.2 g, 0.119 mol) was dissolved in dichloromethane (45 ml) and added dropwise to the mixture over 45 min. The mixture was stirred at same temperature for 3 h and concentrated under reduced pressure. Diisopropyl ether (100 ml) was added to the residue and the mixture was stirred. The precipitated crystals were collected by filtration, and washed with diisopropyl ether to give the title compound (22.78 g), melting point: 130–132° C. as white crystals (yield 70%).

$^1$H-NMR (400 MHz, CDCl$_3$); 0.98–1.04 (1H, m), 1.25–1.31 (2H, m), 1.48–1.55 (2H, m), 1.63–1.70 (1H, m), 1.85–1.94 (2H, m), 4.15 (1H, m), 4.40 (1H, d, J 11.2 Hz), 5.51 (1H, m), 7.28–7.40 (5H, m).

(4) Production of 8-hydroxy-7,9-dioxa-6-phenyl-8-phosphaspiro[4.5]decan-8-one Sodium hydroxide (9.2 g, 0.23 mol) was dissolved in water (92 ml) and the mixture was stirred at 98 to 103° C. with heating, during which 8-chloro-7,9-dioxa-6-phenyl-8-phosphaspiro[4.5]decan-8-one (21.56 g, 0.0752 mol) obtained in 3-1) was pulverized and added in small portions over 10 min, and the pale-orange solution was further stirred for 25 min. The reaction mixture was allowed to cool to 45°C. and concentrated hydrochloric acid (19.5 ml) was added to make the solution acidic. Water (40 ml) was added and the mixture was cooled to 20° C. The fine crystals were collected by filtration and washed with water and then ether. The crystals were dried under reduced pressure at 50° C. to give the title compound (16.56 g, yield 81%) as white crystals, melting point: 173 to 174° C.

$^1$H-NMR (400 MHz, CDCl$_3$+DMSO-d$_6$); 0.92–0.98 (1H, m), 1.14–1.25 (2H, m), 1.40–1.48 (2H, m), 1.50–1.61 (1H, m), 1.85–1.88 (2H, m), 3.94 (1H, dd, J=11.0 Hz and 24.4 Hz), 4.30 (1H, d, J=11.0 Hz), 5.10 (1H, br s), 5.43 (1H, s), 7.35–7.38 (5H, m).

(5) Production of (−)-8-hydroxy-7,9-dioxa-6-phenyl-8-phosphaspiro[4.5]decan-8-one (−)-8-hydroxy-7,9-dioxa-6-phenyl-8-phosphaspiro[4.5]decan-8-one A racemate (16.3 g, 0.06 mol) of 8-hydroxy-7,9-dioxa-6-phenyl-8-phosphaspiro[4.5]decan-8-one and D-(−)-p-hydroxyphenyl glycine (10.16 g, 0.06 mol) were added to ethanol (250 ml) and water (130 ml). The mixture was refluxed for 10 min, during which crystals were mostly dissolved, and the crystals were allowed to precipitate again. The mixture was stirred under room temperature for 1 h and stood in a refrigerator overnight.

The precipitated crystals of a salt of (−)-8-hydroxy-7,9-dioxa-6-phenyl-8-phosphaspiro[4.5]decan-8-one and D-(−)-p-hydroxyphenyl glycine were collected by filtration and washed with ethanol to give 11.82 g thereof.

The crystals were refluxed in ethanol (250 ml) and water (150 ml) for 10 min and stood overnight in a refrigerator. The precipitated crystals were collected by filtration to give white crystals (9.73 g, melting point: from 225° C. to 227° C. (dec.)). $[\alpha]_D^{20}$ –101.2° (c=0.5, methanol) The crystals were suspended in 60 ml of water and 36% hydrochloric acid (12 ml) was added. The mixture was stirred at room temperature for 4 h to allow double decomposition. This was filtered, washed with water and the obtained crystals (6.06 g) were recrystallized from 130 ml of ethanol to give the title compound as white crystals (5.04 g, yield 62%, m.p. 163–164° C.). As a result of the HPLC analysis (Condition C), the enantiomer excess was found to be not less than 99% ee.

$[\alpha]_D^{20}$=–60.6° (c=0.5, methanol).

Elemental analysis for $C_{13}H_{17}O_4P_1$.

Calculated C, 58.21%; H, 6.39%;

Found C, 58.14%; H, 6.25%.

(6) Production of (+)-8-hydroxy-7,9-dioxa-6-phenyl-8-phosphaspiro[4.5]decan-8-one The crystals of a salt of (–)-8-hydroxy-7,9-dioxa-6-phenyl-8-phosphaspiro[4.5]decan-8-one and D-(–)-p-hydroxyphenyl glycine were collected by filtration. The filtrate was concentrated to dryness and dissolved again in ethanol (100 ml) and water (50 ml). After standing at room temperature for one day, the precipitated crystals were collected by filtration (4.2 g). Ethanol was evaporated from the filtrate under reduced pressure, and 36% hydrochloric acid (15 ml) was added. The mixture was stirred at room temperature for 4 h to allow double decomposition. This was filtered and washed with water to give 5.79 g of crystals (yield 70.8%). $[\alpha]_D^{20}$=+49.0° (c=0.5, methanol) The crystals were recrystallized twice from ethanol to give the title compound as white crystals (3.34 g, yield 41%, m.p. 160–161° C.). $[\alpha]_D^{20}$=+59.4° (c=0.5, methanol). As a result of the HPLC analysis (Condition (C)), the enantiomer excess was found to be not less than 99% ee.

Elemental analysis for $C_{13}H_{17}O_4P_1$.

Calculated C, 58.21%; H, 6.39%;

Found C, 58.06%; H, 6.25%.

EXAMPLE 23

(3) Synthesis of ethyl 2,2-dimethyl(2-chlorobenzoyl)acetate

2-Chlorobenzoyl chloride (17.5 g, 0.1 mol) and ethyl 2-bromo-2,2-dimethylacetate (19.5 g, 0.1 mol) were diluted with ether (200 ml) and added dropwise into a 300 ml four-necked flask containing a zinc powder (13.0 g, 0.2 mol). After adding dropwise about 30 ml, the mixture was heated and the remaining solution was added dropwise over 2 h under reflux. After the completion of the dropwise addition, the mixture was refluxed for 4 h and allowed to cool, and 1N-hydrochloric acid (100 ml) was added dropwise. After partitioning, the aqueous layer was extracted with ether (100 ml), and the organic layer was combined. The mixture was dried over sodium sulfate and concentrated. The concentrated dry solid was purified by silica gel column chromatography (silica gel 1 kg, hexane:ethyl acetate=9:1) to give the title compound (13.8 g, 54%) as a colorless oil.

$^1$H-NMR (400 MHz, CDCl$_3$) (: 1.20 (3H, t, J=7.1 Hz), 1.52 (6H, s), 4.14 (2H, q, J=7.1 Hz), 7.26–7.42 (4H, m).

(2) Production of ethyl 3-(2-chlorophenyl)-3-hydroxy-2,2-dimethylpropionate tBuBisP*-RuBr$_2$ (5 mg) was placed in a pressurized hydrogenation reactor equipped with a stirrer chip, and after deaeration, substituted with argon. Thereto was poured a mixture of deaerated ethyl 2,2-dimethyl(2-chlorobenzoyl)acetate (515 mg) (2.0 mmol), methanol (4 ml) and water (0.4 ml). The mixture was stirred under a hydrogen pressure (6 atm) at 70° C. for 24 h. According to the high performance liquid chromatography analysis of the mixture after completion of the reaction, the yield was 97% and enantioselectivity was 90% ee. After the analysis, the reaction mixture was concentrated to dryness and purified by column chromatography (hexane:ethyl acetate=3:1, silica gel: 50 g) to give the title compound (420 mg, 81.8%) as a colorless oil.

$^1$H-NMR (400 MHz, CDCl$_3$) δ: 1.19 (6H, s), 1.29 (3H, t, J=7.1 Hz), 3.51 (1H, d, J=4.4 Hz), 4.21 (2H, q, J=7.1 Hz), 5.51 (1H, d, J=4.4 Hz), 7.19–7.54 (4H, m).

IR (KBr) ν cm$^{-1}$: 3494, 2983, 1714.

$[\alpha]^{24}_D$=–30.4° (c-1.0, chloroform).

(3) Production of 1-(2-chlorophenyl)-2,2-dimethyl-1,3-propanediol

Lithium aluminum hydride (0.5 g, 11.7 mmol) was suspended in ether (50 ml) and cooled to –20° C. to –30° C. Thereto was added dropwise a solution of ethyl 2,2-dimethyl-3-hydroxy(2-chlorobenzoyl)acetate (2 g, 7.8 mmol) in ether (10 ml) while maintaining at not higher than –20° C. The mixture was stirred at –20° C. for 1 h and at 0° C. for 3 h, cooled to –20° C. and 10%—NaHSO$_4$ aqueous solution (20 ml) was added dropwise. The mixture was stirred at room temperature for 30 min, and an insoluble material was removed by decantation. This was washed twice with ether (100 ml) and the organic layer was combined. The mixture was washed with water, dried over anhydrous sodium sulfate, and concentrated to dryness to give the title compound (1.3 g, 78%) as a colorless oil.

$^1$H-NMR (400 MHz, CDCl$_3$) δ: 0.92 (3H, s), 0.95 (3H, s), 2.63 (1H, brs), 3.11 (1H, brs), 3.60 (1H, dd, J=10.8 and 13.6 Hz), 3.64 (1H, dd, J=10.8 and 13.6 Hz), 5.31 (1H, s), 7.19–7.62 (4H, m).

(4) Production of 4-(2-chlorophenyl)-2-chloro-5,5-dimethyl-1,3,2-dioxaphosphorinan 2-oxide 1-(2-Chlorophenyl)-2,2-dimethyl-1,3-propanediol (1.0 g, 4.66 mmol) was diluted with dichloromethane (5 ml) and, under reflux, a solution of phosphorus oxychloride (0.65 g, mmol) in dichloromethane (3 ml) was added dropwise over 40 min. After the dropwise addition, the mixture was refluxed for 6 h. The mixture after completion of the reaction was concentrated, and after addition of ether (dry, 5 ml), concentrated again to dryness to give the title compound (1.23 g, 90%) as colorless crude crystals.

(5) Production of 4-(2-chlorophenyl)-2-hydroxy-5,5-dimethyl-1,3,2-dioxaphosphorinan 2-oxide Sodium hydroxide (0.25 g) was dissolved in water (3 ml) and the solution was heated to 95 to 100° C. 4-(2-Chlorophenyl)-2-chloro-5,5-dimethyl-1,3,2-dioxaphosphorinan 2-oxide (1.23 g, 4.18 mmol) was added as a powder over 30 min and the mixture was stirred at the same temperature for 1 h. The reaction mixture was allowed to cool to 60° C. and concentrated hydrochloric acid (1 ml) was added. The mixture was cooled to 13 to 15° C. and the precipitated white crystals were collected by filtration, washed successively with water (2 ml) and ether (2 ml), and dried in vacuo to give white crystals (1.00 g, 88.9%). The enantiomer excess of this product was measured by high performance liquid chromatography (Condition (D)) and found to be 85.6% ee. The obtained crystals (730 mg) were dissolved in 50% aqueous ethanol solution (3 ml) with heating and stood at room temperature. The precipitated crystals were collected by filtration to give the title compound (340 mg, 98.7% ee, yield: 50%) as white crystals. The mother liquor was concentrated to dryness and again recrystallized to recover the title compound from the mother liquor as white crystals (200 mg, 96.5% ee., yield: 26%).

$^1$H-NMR (400 MHz, CDCl$_3$) δ: 0.84 (3H, s), 1.11 (3H, s), 3.90 (1H, q, J=11.0 Hz), 4.40 (1H, q, J=11.0 Hz), 5.88 (1H, s), 7.25–7.53 (5H, m).

EXAMPLE 24

(1) Production of ethyl 1-benzoylcyclopropanecarboxylate

To 1370 ml of acetonitrile were added ethyl benzoylacetate (49.9 g, 0.26 mol), 1,2-dibromomethane (48.8 g, 0.26 g) and anhydrous potassium carbonate (143.6 g, 1.04 mol) and the mixture was stirred under reflux for 18 h. After cooling, the reaction mixture was filtrated and concentrated. The residual solution (56.3 g) was purified by silica gel column chromatography (ethyl acetate/hexane=1/5) to give the title compound (38.7 g) as a colorless oil (yield 68%).

$^1$H-NMR (90 MHz, CDCl$_3$) δ: 0.95 (3H, t, J=7.1 Hz), 1.51–1.56 (1H, m), 1.57–1.64 (3H, m), 4.04 (2H, q, J=7.1 Hz), 7.43–7.46 (2H, m), 7.53–7.57 (1H, m), 7.89–7.91 (2H, m).

(2) Production of 1-(1-hydroxy-1-phenylmethyl)-1-hydroxymethylcyclopropane

Under a nitrogen stream, lithium aluminum hydride (4.55 g, 0.12 mol) was suspended in dehydrated ether (120 ml) and a solution (50 ml) of ethyl 1-benzoylcyclopropanecarboxylate (21.83 g, 0.1 mol) in dehydrated ether was added dropwise over 50 min while stirring under ice-cooling. The mixture was stirred at room temperature for 1.5 h, and 10% aqueous sodium hydrogen carbonate (15 ml) was slowly added dropwise under ice-cooling. Then 20% aqueous sodium hydroxide (30 ml) was added dropwise, and the mixture was stirred for 30 min. The ether layer was separated by decantation and the residue was washed twice with 30 ml of ether. The ether layer was combined, washed with saturated brine, dehydrated over anhydrous magnesium sulfate and concentrated. The residual solution (16.9 g) was purified by silica gel column chromatography (chloroform/methanol=20/1) to give the title compound (14.51 g) as a colorless oil (yield 81%).

$^1$H-NMR (400 MHz, CDCl$_3$) δ: 0.42–0.47 (1H, m), 0.61–0.71 (3H, m), 2.78 (1H, t, J=4.9 Hz), 3.17 (1H, dd, J=4.9 Hz and 11.5 Hz), 3.59 (1H, d, J=4.6 Hz), 3.74 (1H, dd, J=4.6 Hz and 11.5 Hz), 4.46 (1H, d, J=4.4 Hz), 7.26–7.39 (5H, m).

(3) Production of 6-chloro-5,7-dioxa-4-phenyl-6-phosphaspiro[2.5]octane-6-one 1-(1-Hydroxy-1-phenylmethyl)-1-hydroxymethylcyclopropane (3.2 g, 0.018 mol) and triethylamine (4.01 g, 0.04 mol) were dissolved in dichloromethane (30 ml), and the mixture was stirred at 5 to 8° C. Phosphorus oxychloride (2.89 g, 0.019 mol) was dissolved in dichloromethane (10 ml) and the solution was added dropwise under ice-cooling over 40 min. The mixture was stirred at same temperature for 2 h, cooled and washed with water (30 ml). The aqueous layer was extracted with dichloromethane (15 ml), and the organic layer was combined and washed with saturated brine. The mixture was dehydrated over anhydrous magnesium sulfate and concentrated to give 4.48 g of an oil. This was purified by silica gel column chromatography (ethyl acetate/hexane=1/1) and washed with isopropyl ether to give the title compound as white crystals (0.47 g, yield 10%, m.p. 81–83° C.).

$^1$H-NMR (400 MHz, CDCl$_3$); 0.35–0.40 (1H, m), 0.54–0.59 (1H, m), 0.66–0.72 (2H, m), 3.71 (1H, dd, J=11.7 Hz, 29.3 Hz), 4.96 (1H, m), 5.89 (1H, m), 7.27–7.41 (5H, m).

(4) Production of 6-hydroxy-5,7-dioxa-4-phenyl-6-phosphaspiro[2.5]octane-6-one

Sodium hydroxide (0.18 g, 4.5 mmol) was dissolved in water (2 ml), and 6-chloro-5,7-dioxa-4-phenyl-6-phosphaspiro[2.5]octane-6-one (0.4 g, 1.55 mmol) was added by small portions while stirring the mixture with heating at 85–88° C. on an oil bath. The addition was completed in 5 min, and the mixture was further stirred for 20 min after raising the bath temperature to 90° C. The reaction mixture was allowed to cool and concentrated hydrochloric acid (0.6 ml) was added to make the mixture acidic. The mixture was stirred under ice-cooling for 1.5 h and the precipitated crystals were collected by filtration, and washed with water and then ether to give the title compound as white crystals (0.13 g, yield 35%, m.p. 122–123° C.).

$^1$H-NMR (400 MHz, CDCl$_3$+DMSO-d$_6$); 0.23–0.28 (1H, m), 0.41–0.46 (1H, m), 0.56–0.59 (2H, m), 3.53 (1H, dd, J=11.5 Hz and 23.0 Hz), 4.82 (1H, dd, J=11.5 Hz), 5.27 (1H, s), 7.30–7.63 (5H, m).

EXAMPLE 25

6-hydroxy-5,7-dioxa-4-phenyl-6-phosphaspiro[2.5]octane-6-one (consistent synthesis from 1-(1-hydroxy-1-phenylmethyl)-1-hydroxymethylcyclopropane)

1-(1-Hydroxy-1-phenylmethyl)-1-hydroxymethylcyclopropane (10.0 g, 0.0561 mol) was dissolved in dichloromethane (90 ml) and triethylamine (15.9 g, 0.157 mol) was added thereto. A solution of phosphorus oxychloride (8.7 g, 0.0567 mol) in dichloromethane (30 ml) was added dropwise over 65 min while stirring the mixture under ice-cooling (5 to 8° C.). The mixture was stirred under ice-cooling for 2 h, washed twice with water (50 ml), dried over anhydrous magnesium sulfate and concentrated. The crude intermediate chloride compound (15.08 g) was obtained as a dark brown oil.

Sodium hydroxide (6.8 g) was dissolved in water (70 ml), and the above-mentioned crude product (15.08 g) was added by small portions while stirring the mixture at an outer temperature of 83 to 87° C. The addition was completed in 20 min, and the mixture was heated to 90 to 93° C. and stirred for 30 min. The oil bath was removed, and the mixture was stirred for a while and diethyl ether (40 ml) was added. Then, concentrated hydrochloric acid (17 ml) was added to make the mixture acidic. The mixture was stirred under ice-cooling for 0.5 h and the crystals were collected by filtration, and washed successively with water and ether to give the title compound as colorless crystals (5.65 g, yield 41.9%, m.p. 120–122° C.).

EXAMPLE 26

Optical resolution of (±)-6-hydroxy-5,7-dioxa-4-phenyl-6-phosphaspiro[2.5]octane-6-one 6-Hydroxy-5,7-dioxa-4-phenyl-6-phosphaspiro[2.5]octane-6-one (racemate, 13.1 g, 54.5 mmol) and (+)-cis-N- benzyl-2-(hydroxymethyl)cyclohexylamine (11.96 g, 54.6 mmol) were dissolved in ethanol (100 ml) with heating. Thereto was added ethyl acetate (150 ml) under heating and the mixture was stood at room temperature overnight. The precipitated crystals were collected by filtration to give a salt (9.45 g) of the (−) compound. The crystals were recrystallized twice from ethanol to give 6.47 g of crystals (m.p. 209–211° C.). $[\alpha]_D^{20}$=−30.0° (c=0.5, MeOH).

This was suspended in water (25 ml) and 36% hydrochloric acid (7 ml) was added. The mixture was stirred at room temperature for 2 h to allow decomposition. The crystals were collected by filtration, and washed with water to give 3.32 g of colorless crystals of (−)-compound (yield 50.7%, m.p. 136–137° C.). $[\alpha]_D^{20}$=−47.6° (c=0.5, MeOH) As a result of the HPLC analysis (Condition A), the enantiomer excess was found to be >99.9% ee.

The filtrate after collecting the salt of (−)-compound was decomposed by 36% hydrochloric acid to recover 7.93 g (33.0 mmol) of crystals containing a large amount of (+)-compound.

Thereto was added (−)-cis-N-benzyl-2-(hydroxymethyl)cyclohexylamine (7.24 g, 33.0 mmol) and dissolved in ethanol (70 ml) with heating. The mixture was stirred at room temperature for 2 h, and under ice-cooling for 2 h and filtrated. This was recrystallized from ethanol (60 ml) to give crystals (7.02 g, m.p. 210–211° C.). $[\alpha]_D^{20}$=+33.0° (c=0.5, MeOH) This was suspended in water (30 ml) and 36% hydrochloric acid (7.6 ml) was added for decomposition. The crystals were collected by filtration, washed with water and recrystallized from ethanol (90 ml) to give 2.58 g of (+)-compound as colorless crystals (m.p. 131–133° C., yield 39.4%). $[\alpha]_D^{20}$=+47.8° (c=0.5, MeOH). As a result of the HPLC analysis (Condition A), the enantiomer excess was found to be >99.9% ee.

EXAMPLE 27

(1) Production of ethyl 1-(1-hydroxy(2-chlorophenyl)methyl)cyclopentanecarboxylate 'BuBisP*RuBr$_2$ (28 mg) was placed in a reactor and deaerated and substituted with argon. A mixture of deaerated methanol/water (10/1) (33 ml) and ethyl 1-(2-chlorobenzoyl)cyclopentanecarboxylate (3.2 g, 11.4 mmol) was added. Under a hydrogen pressure (6 atm), the mixture was stirred at 70° C. for 7 h and concentrated to dryness. This was dissolved in ethyl acetate, dried over anhydrous sodium sulfate and purified by silica gel column chromatography to give the title compound (2.59 g, yield; 80.9%) as a colorless oil. The enantiomer excess of this product was measured by high performance liquid chromatography (Condition F) and found to be 90% ee.

$^1$H-NMR (400 MHz, CDCl$_3$) δ: 1.25 (3H, t, J=7.1 Hz), 1.56–1.62 (4H, m), 1.73–2.20 (4H, m), 3.80 (1H, d, J=6.2 Hz), 4.20 (2H, q, J=7.1 Hz), 5.39 (1H, d, J=6.2 Hz), 7.20–7.40 (4H, m).

IR (neat) ν cm$^{-1}$: 3485, 2958, 1714.

$[\alpha]_D^{25}$=−41.9° (c=1.0, chloroform).

(2) Production of [1-(hydroxymethyl)cyclopentyl](2-chlorophenyl)methanol

Lithium aluminum hydride (0.64 g, 16.8 mmol) was mixed with ether (20 ml) and cooled to −10° C. Thereto was added dropwise a solution of ethyl 1-(1-hydroxy(2-chlorophenyl)methyl)cyclopentanecarboxylate (3.1 g, 11.2 mmol) in ether (5 ml) at the same temperature over 15 min, and the mixture was stirred at −10° C. for 1 h, and at room temperature for 3 h. The mixture was cooled to −20° C. and 10%—NaHCO$_3$ aq. (2 ml) was added dropwise, then 20%—NaOH aq. (2 ml) was added dropwise. The mixture was stirred for 30 min and sludge was removed by decantation. The organic layer was washed with water (50 ml), dried over anhydrous sodium sulfate, concentrated to dryness, and purified by silica gel column chromatography (hexane:ethyl acetate =2:1) to give the title compound 2.2 g (quant.) as a colorless oil.

$^1$H-NMR (400 MHz, CDCl$_3$) δ: 1.10–1.17 (1H, m), 1.52–1.77 (7H, m), 2.80 (2H, br), 3.48 (1H, d, J=11.0 Hz), 3.76 (1H, d, J=11.0 Hz), 5.35 (1H, s), 7.22–7.35 (3H, m), 7.69 (1H, dd, J=1.7 and 4.7 Hz).

IR (neat) ν cm$^{-1}$: 3349, 2955, 2871, 1707.

(3) Production of 8-chloro-6-(2-chlorophenyl)-7,9-dioxa-8-phosphospiro[4.5]decan-1-one

[1-(Hydroxymethyl)cyclopentyl](2-chlorophenyl)methanol (2.1 g, 8.72 mmol) was diluted with dichloromethane (15 ml), and under reflux, a solution of phosphorus oxychloride (1.4 g, 8.73 mmol) in dichloromethane (10 ml) was added dropwise over 30 min. The mixture was stirred at reflux temperature for 5 h and concentrated to give crude title compound as a colorless oil.

(4) Production of 6-(2-chlorophenyl)-8-hydroxy-7,9-dioxa-8-phosphospiro[4.5]decan-8-one Sodium hydroxide (1.1 g) was dissolved in water (10 ml) and heated to 95 to 100° C. A solution (3 ml) of 8-chloro-6-(2-chlorophenyl)-7,9-dioxa-8-phosphospiro[4.5]decan-8-one (8.72 mmol) in diethyl ether was added over 15 min. The mixture was stirred at the same temperature for 20 min, and after allowing the reaction mixture to cool to 60° C., concentrated hydrochloric acid (3 ml) was added. The mixture was cooled to 13–15° C. and the precipitated white crystals were collected by filtration, washed successively with water (5 ml) and ether (5 ml) and dried in vacuo to give the title compound (2.1 g, 79.5%) as white crystals. The enantiomer excess of the obtained white crystals was measured by high performance liquid chromatography (Condition E) and found to be 92%.

This was recrystallized from ethanol and purified to give the title compound (1.3 g, 49.7%, 99% ee) as white crystals (m.p. 205–206° C. (dec.)).

$^1$H-NMR (400 MHz, CDCl$_3$) δ: 1.25–1.34 (4H, m), 1.45–1.52 (2H, m), 1.88–1.92 (2H, m), 4.02 (1H, dd, J=11.2 and 24.8 Hz), 4.37 (1H, d, J=11.2 Hz), 6.03 (1H, d, J=1.7 Hz), 7.24–7.35 (3H, m), 7.59 (1H, dd, J=7.5 and 1.8 Hz).

$[\alpha]_D^{20}$=−52.0° (c=0.5, ethanol).

EXAMPLE 28

(1) Production of ethyl 1-[(2,4-dichlorophenyl)(hydroxy)methyl]cyclopentanecarboxylate (S)-tBuBisP*-RuBr$_2$ (16 mg) was placed in a reactor and deaerated. After substitution with argon, a mixture of ethyl 1-(2,4-dichlorobenzoyl)cyclopentanecarboxylate (2.8 g, 5.6 mmol) and methanol-water (101) (30 ml) was added. Under 70° C. and hydrogen pressure (6 kg/cm$^2$), the mixture was stirred for 30 h and concentrated. This was diluted with ethyl acetate (50 ml), washed with water and concentrated to dryness. This was purified by silica gel column chromatography (hexane:ethyl acetate=4:1) to give the title compound (0.91 g, 41.3%) as a colorless oil. The enantiomer excess of this product was measured by high performance liquid chromatography (Condition F) and found to be 92%.

$^1$H-NMR (400 MHz, CDCl$_3$) δ: 1.25 (3H, t, J=7.1 Hz), 1.56–2.18 (8H, m), 3.83 (1H, d, J=6.3 Hz), 4.19 (2H, m), 5.33 (1H, d, J=6.3 Hz), 7.22–7.42 (3H, m).

IR (neat) ν cm$^{-1}$: 3476, 2959, 1720.

$[\alpha]_D^{24}$=−34.7° (c=1.0, chloroform).

(2) Production of (2,6-dichlorophenylmethyl)[1-(hydroxymethyl)cyclopentyl]methanol Lithium aluminum hydride (0.29 g, 7.6 mmol) was suspended in ether (10 ml) and the suspension was cooled to −5° C. to 0° C. Thereto was added dropwise a solution of ethyl 1-[(2,4-dichlorophenyl)(hydroxy)methyl] cyclopentanecarboxylate (1.6 g, 5 mmol) in ether (5 ml) while maintaining at not higher than 10° C. over 30 min. The mixture was stirred at the same temperature for 1 h and at room temperature for 3 h, cooled to 0° C., and 10%—NaHCO$_3$ aqueous solution (2 ml) and 20%—NaOH aqueous solution (2 ml) were added dropwise. The mixture was stirred for 30 min, and an insoluble material was removed by decantation. This was extracted twice with ethyl acetate (100 ml). The organic layer was combined, and the mixture was washed with water, dried over anhydrous sodium sulfate and concentrated to dryness to give the title compound (1.3 g, 95.5%) as a colorless oil.

$^1$H-NMR (400 MHz, CDCl$_3$) δ: 1.53–1.72 (8H, m), 2.80 (1H, brs), 3.50 (1H, dd, J=4.0 Hz and 10.7 Hz), 3.62 (1H, d, J=3.4 Hz), 3.72 (1H, dd, J=3.4 Hz and 10.7 Hz), 5.29 (1H, d, J=4.1 Hz), 7.26–7.36 (2H, m), 7.63 (1H, d, J=8.5 Hz).

(3) Production of 8-chloro-6-(2,4-dichlorophenyl)-7,9-dioxa-8-phosphospiro[4.5]decan-8-one (2,6-Dichlorophenylmethyl)[1-(hydroxymethyl) cyclopentyl]methanol (1.3 g, 4.72 mmol) was diluted with dichloromethane (8 ml), and under reflux, a solution of phosphorus oxychloride (0.72 g, 4.72 mmol) in dichloromethane (5 ml) was added dropwise over 30 min. The mixture was stirred at reflux temperature for 5 h and concentrated to give a crude title compound as a colorless oil.

(4) Production of 6-(2,4-dichlorophenyl)-8-hydroxy-7,9-dioxa-8-phosphospiro[4.5]decan-8-one Sodium hydroxide (0.57 g) was dissolved in water (6 ml) and the mixture was heated to 95 to 100° C. A solution (2 ml) of 8-chloro-6-(2,4-dichlorophenyl)-7,9-dioxa-8-phosphospiro[4.5]decan-8-one (4.42 mmol) in diethyl ether was added over 15 min and the mixture was stirred at the same temperature for 20 min. The reaction mixture was allowed to cool to 60° C. and concentrated hydrochloric acid (3 ml) was added. The mixture was cooled to 13 to 15° C. and the precipitated white crystals were collected by filtration, washed successively with water (2 ml) and ether (2 ml), and dried in vacuo to give the title compound (0.81 g, 50.7%) as white crystals. The crystals were recrystallized for purification from ethanol to give the title compound as white crystals (500 mg, 37%, m.p. 208–209° C.). The enantiomer excess of this product was measured by high performance liquid chromatography (Condition E) and found to be 99.5%.

$^1$H-NMR (400 MHz, CDCl$_3$) δ: 1.28–1.93 (5H, m), 4.01 (1H, dd, J=11.2 and 24.7 Hz), 4.35 (1H, d, J=11.2 Hz), 5.96 (1H, s), 7.26–7.40 (3H, m).

$[\alpha]_D^{27}$=−49.2° (c=0.5, MeOH).

EXAMPLE 29

(1) Production of ethyl 1-[hydroxy(phenyl)methyl]cyclopropanecarboxylate (S)-$^t$BuBisP*-RuBr$_2$ (25 mg) was placed in a reaction vessel and deaerated. After substitution with argon, a mixture of ethyl 1-benzoylcyclopropanecarboxylate (3.3 g, 1.0 mmol) and methanol-water (10/1) (33 ml) was added. The mixture was stirred at 70° C. and hydrogen pressure (6 kg/cm$^2$) for 24 h, after which the reaction mixture was concentrated. This was concentrated to dryness, diluted with ethyl acetate, washed with water and purified by silica gel column chromatography (hexane:ethyl acetate=4:1) to give the title compound (1.53 g, 46.3%) as a colorless oil. The enantiomer excess of this product was measured by high performance liquid chromatography (Condition F) and found to be 85%.

$^1$H-NMR (400 MHz, CDCl$_3$) δ: 0.80–0.84 (1H, m), 0.94–0.99 (1H, m), 1.17 (3H, t, J=7.1 Hz), 1.17–1.38 (2H, m), 3.47 (1H, d, J=6.7 Hz), 4.11 (2H, q, J=7.1 Hz), 4.85 (1H, d, J=6.7 Hz), 7.26–7.41 (5H, m).

(2) Production of [1-(hydroxymethyl)cyclopropyl](phenyl)methanol

Lithium aluminum hydride (0.39 g, 10.2 mmol) was mixed with ether (12 ml) and the mixture was cooled to −10° C. Thereto was added dropwise a solution of ethyl 1-[hydroxy(phenyl)methyl]cyclopropanecarboxylate (1.5 g, 6.8 mmol) in ether (3 ml) at the same temperature over 15 min, and the mixture was stirred at −10° C. for 1 h and at room temperature for 2 h. Thereafter, the mixture was cooled to −20° C., and 10% NaHCO$_3$ aq. (2 ml) was added dropwise. Then, 20% NaOH aq. (2 ml) was added dropwise, and the mixture was stirred for 30 min. Sludge was removed by decantation and the organic layer was washed with water (50 ml), dried over anhydrous sodium sulfate, concentrated to dryness, and purified by silica gel column chromatography (hexane:ethyl acetate=3:1) to give the title compound (1.2 g, 98.9%) as a colorless oil.

$^1$H-NMR (400 MHz, CDCl$_3$) δ: 0.40–0.73 (4H, m), 2.70 (2H, brs), 3.20 (1H, d, J=11.3 Hz), 3.76 (1H, d, J=11.3 Hz), 4.82 (1H, s), 7.26–7.41 (5H, m).

$[\alpha]_D^{24}$=17.2° (c 0.5, chloroform).

(3) Production of 6-chloro-4-phenyl-5,7-dioxa-6-phosphospiro[2.5]octane-6-one

[1-(Hydroxymethyl)cyclopropyl](phenyl)methanol (1.0 g, 5.61 mmol) was diluted with dichloromethane (9 ml), and triethylamine (1.6 g, 15.8 mmol) was added. The mixture was cooled to 0 to 5° C., and a solution of phosphorus oxychloride (0.87 g, 5.61 mmol) in dichloromethane (3 ml) was added dropwise over 15 min at the same temperature. After the dropwise addition, the mixture was stirred for 2 h. Then, water (5 ml) was added dropwise and the mixture was partitioned. The organic layer was dried over anhydrous magnesium sulfate and concentrated. Dry ether (5 ml) was added to give a suspension and the suspension was filtrated to give the title compound (510 mg) as pale-red crystals. In the same manner as above, the title compound was obtained from the mother liquor as pale-red crystals (100 mg), (total yield: 42.0%).

$^1$H-NMR (400 MHz, CDCl$_3$) δ: 0.34–0.40 (1H, m), 0.53–0.59 (1H, m), 0.67–0.71 (2H, m), 3.72 (1H, dd, J=11.7 and 29.3 Hz), 4.96 (1H, dt, J=2.1 and 11.7 Hz), 5.89 (1H, d, J=2.2 Hz), 7.27–7.29 (2H, m), 7.36–7.40 (3H, m).

(4) Production of 6-hydroxy-4-phenyl-5,7-dioxa-6-phosphospiro[2.5]octane-6-one Sodium hydroxide (320 mg) was dissolved in water (3.2 ml) and the mixture was heated to 95–100° C. 6-Chloro-4-phenyl-5,7-dioxa-6-phosphospiro[2.5]octane-6-one (600 mg, 2.64 mmol) was added over 15 min, and the mixture was stirred at the same temperature for 10 min. The mixture was allowed to cool to 60° C. and concentrated hydrochloric acid (1 ml) was added. The mixture was cooled to 13 to 15° C. and ether (1 ml) was added. The mixture was stirred and the precipitated white crystals were collected by filtration, washed successively with water (2 ml) and ether (2 ml) and dried in vacuo. The obtained pale-brown crystals were recrystallized from ethanol for purification to give the title compound (380 mg, 83%) as white crystals. The enantiomer excess of this product was measured by high performance liquid chromatography (Condition E) and found to be not less than 97%.

$^1$H-NMR (400 MHz, CDCl$_3$) δ: 0.23–0.27 (1H, m), 0.43–0.48 (1H, m), 0.54–0.58 (2H, m), 3.50 (1H, dd, J=11.3 Hz, 22.7 Hz), 4.81 (1H, d, J=11.2 Hz), 5.77 (1H, s), 7.30–7.52 (5H, m).

$[\alpha]_D^{24}$=−46.1° (c=0.5, methanol).

COMPARATIVE EXAMPLE 1

Production of salt of 1-(6,7-dimethoxynaphthalen-2-yl)-1-(1H-imidazol-4-yl)-2-methyl-1-propanol and (1S,2R)-cis-2-benzamidecyclohexanecarboxylic acid A racemate (50 mg) of 1-(6,7-dimethoxynaphthalen-2-yl)-1-(1H-imidazol-4-yl)-2-methyl-1-propanol and (1S,2R)-cis-2-benzamidecyclohexanecarboxylic acid (37.9 mg) were dissolved in isopropyl alcohol (0.6 ml). The solution was stood still overnight in a refrigerator, and the precipitate was collected by filtration to give crystals (8.4 mg, yield 19%). As a result of the HPLC analysis (Condition B), the diastereomer excess was found to be 3% de.

COMPARATIVE EXAMPLE 2

Production of salt of 1-(6,7-dimethoxynaphthalen-2-yl)-1-(1H-imidazol-4-yl)-2-methyl-1-propanol and (S)-1-phenylethylsulfamic acid A racemate (25 mg) of 1-(6,7-dimethoxynaphthalen-2-yl)-1-(1H-imidazol-4-yl)-2-methyl-1-propanol and (S)-1-phenylethylsulfamic acid (15.4 mg) were dissolved in ethanol (0.5 ml). The solution was stood still overnight in a refrigerator, and the precipitate was collected by filtration to give crystals (10 mg, yield 50%). As a result of the HPLC analysis (Condition B), the diastereomer excess was found to be 2% de.

COMPARATIVE EXAMPLE 3

Production of salt of 1-(6,7-dimethoxynaphthalen-2-yl)-1-(1H-imidazol-4-yl)-2-methyl-1-propanol and (S)-mandelic acid A racemate (50 mg) of 1-(6,7-dimethoxynaphthalen-2-yl)-1-(1H-imidazol-4-yl)-2-methyl-1-propanol and (S)-(+)-mandelic acid (23.3 mg) were dissolved in ethanol (1.0 ml). The solution was stood still overnight in a refrigerator but precipitate was not observed.

INDUSTRIAL APPLICABILITY

According to the production method of an optically active form of compound (I) of the present invention, a novel diastereomer salt of an optically active naphthalene derivative, useful as a pharmaceutical agent, can be obtained extremely easily. By separation and subsequent decomposition of the diastereomer salt, an optically active naphthalene derivative having a high optical purity can be obtained efficiently. Since a reagent for optical resolution can be recovered and reused, the method is superior as an industrial production method. The optically active compound (IIa) of the present invention can be utilized as a reagent for resolution of a racemate of an optically active amine, or optically active intermediates, such as pharmaceutical agents, agricultural chemicals, liquid crystals and the like. According to the production method of the optically active compound (IIa) of the present invention, an optically pure and optically active form can be produced efficiently in a high yield by a convenient method.

What is claimed is:

1. A compound represented by the formula (IIa):

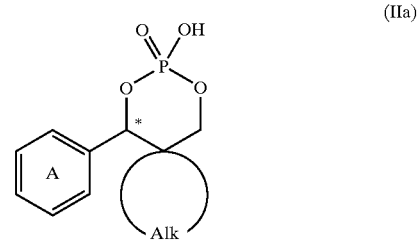

(IIa)

wherein ring A is a benzene ring optionally having 1 to 5 substituents selected from the group consisting of
   (1) $C_{1-6}$ alkyl group which may have a substituent selected from the group consisting of
      (i) halogen atom,
      (ii) $C_{1-7}$ alkoxy group,
      (iii) $C_{1-7}$ alkylthio group,
      (iv) hydroxy group,
      (v) acetylamino,
      (vi) benzoylamino,
      (vii) methanesulfonylamino and
      (viii) benzenesulfonylamino,
   (2) hydroxy group,
   (3) linear or branched $C_{1-6}$ alkoxy group,
   (4) $C_{1-4}$ alkanoyloxy group,
   (5) carbamoyloxy group which may have 1 or 2 $C_{1-4}$ alkyl groups,
   (6) thiol group,
   (7) $C_{1-4}$ alkylthio group,
   (8) $C_{1-4}$ alkanoylthio group,
   (9) nitro group,
   (10) $C_{1-6}$ alkanoyl group,
   (11) $C_{1-4}$ alkylsulfonyl group,
   (12) benzenesulfonyl,
   (13) p-toluenesulfonyl,
   (14) carbamoyl group,
   (15) mono- or di-$C_{1-10}$ alkylcarbamoyl group,
   (16) mono- or di-$C_{6-14}$ arylcarbamoyl group,
   (17) mono- or di-$C_{7-16}$ aralkylcarbamoyl group,
   (18) sulfamoyl group,
   (19) mono- or di-$C_{1-10}$ alkylsulfamoyl group,
   (20) mono- or di-$C_{6-14}$ arylsulfamoyl group,
   (21) mono- or di-$C_{7-16}$ aralkylsulfamoyl group,

(22) $C_{1-4}$ alkoxy-carbonyl group,
(23) halogen atom and
(24) methylenedioxy group which may have a substituent selected from the group consisting of
  (i) halogen,
  (ii) nitro group,
  (iii) hydroxy group and
  (iv) amino group;

Alk is a $C_{2-4}$ alkylene optionally having substituents selected from the group consisting of
  (1) $C_{1-4}$ alkyl group,
  (2) $C_{1-4}$ alkoxy group,
  (3) hydroxy group,
  (4) amino group,
  (5) nitro group and
  (6) halogen group;

and * shows the position of an asymmetric carbon,
or a salt thereof.

2. The compound of claim 1, which is an optically active form.

* * * * *